US011578321B2

(12) United States Patent
Chou et al.

(10) Patent No.: US 11,578,321 B2
(45) Date of Patent: Feb. 14, 2023

(54) RECOMBINANT HBV REPORTER SYSTEM

(71) Applicants: Helmholtz Zentrum München Deutsches Forschungszentrum für Gesundheit und Umwelt (GmbH), Neuherberg (DE); Technische Universität München, Munich (DE)

(72) Inventors: Wen-Min Chou, Miaoli County (TW); Ulrike Protzer-Knolle, Munich (DE); Martin Mueck-Haeusl, Grasbrunn (DE); Chunkyu Ko, Munich (DE); Jochen Wettengel, Wertheim (DE)

(73) Assignees: Helmholtz Zentrum München Deutsches Forschungszentrum für Gesundheit und Umwelt (GmbH), Neuherberg (DE); Technische Universität München, Munich (DE)

( * ) Notice: Subject to any disclaimer, the term of this patent is extended or adjusted under 35 U.S.C. 154(b) by 566 days.

(21) Appl. No.: 16/542,099

(22) Filed: Aug. 15, 2019

(65) Prior Publication Data

US 2020/0056171 A1 Feb. 20, 2020

Related U.S. Application Data

(60) Provisional application No. 62/719,393, filed on Aug. 17, 2018.

(51) Int. Cl.
| | |
|---|---|
| *C12N 15/63* | (2006.01) |
| *C12N 15/74* | (2006.01) |
| *C07H 21/04* | (2006.01) |
| *A61K 48/00* | (2006.01) |
| *C12N 15/10* | (2006.01) |
| *C12N 15/86* | (2006.01) |
| *C07K 14/47* | (2006.01) |
| *G01N 33/50* | (2006.01) |
| *C12N 15/85* | (2006.01) |

(52) U.S. Cl.
CPC ...... *C12N 15/1086* (2013.01); *C07K 14/4731* (2013.01); *C12N 15/86* (2013.01); *C12Y 207/07* (2013.01); *G01N 33/5067* (2013.01); *C07H 21/04* (2013.01); *C12N 15/63* (2013.01); *C12N 2015/859* (2013.01); *C12N 2800/40* (2013.01)

(58) Field of Classification Search
CPC .... C12N 15/63; C12N 15/86; C12N 2800/40; C12N 2510/00; C07H 21/04
See application file for complete search history.

(56) References Cited

PUBLICATIONS

Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Bai, W., et al. (2016) "Engineering Hepadnaviruses as Reporter-Expressing Vectors: Recent Progress and Future Perspectives", Viruses, 8:1-16.
Dassa, B., et al. (2009) "Fractured genes: a novel genomic arrangement involving new spilt inteins and a new homing endonuclease family", Nucleic Acids Research, 37:2560-2573.
Traunecker, A., et al. (1991) "Bispecific single chain molecules (Janusins) target cytotoxic lymphocytes on HIV infected cells," The EMBO Journal, 10:3655-3659.
Glasgow, A.C., et al. (1989) "DNA-binding Properties of the Hin Recombinase", The Journal of Biological Chemistry, 264:10072-10082.
Hermann, M., et al. (2014) "Binary recombinase systems for high-resolution conditional mutagenesis", Nucleic Acids Research, 42:3894-3907.
Hickman, A.B., et al. (2015) "Mechanisms of DNA Transposition", Author Manuscript, Published in final edited form as: Microbiol Spectr., 3:MDNA3-0034-2014, 34 pages.
Ladner, S.K., (1997) "Inducible Expression of Human Hepatitis B Virus (HBV) in Stably Transfected Hepatoblastoma Cells: a Novel System for Screening Potential Inhibitors of HBV Replication", Antimicrobial Agents and Chemotherapy, 41:1715-1720.
Matsuda, T., et al. (2007) "Controlled expression of transgenes introduced by in vivo electroporation", PNAS, 104:1027-1032.
Silverman, J., et al. (2005) "Multivalent avimer proteins evolved by exon shuffling of a family of human receptor domains", Nature Biotechnology, 23:1556-1561.
Nakabayashi, H., et al. (1982) "Growth of Human Hepatoma Cell Lines with Differentiated Functions in Chemically Defined Medium", Cancer Research, 42:3858-3863.
Nassal, M., et al. (1990) "Translational Inactivation of RNA Function: Discrimination against a Subset of Genomic Transcripts during HBV Nucleocapsid Assembly", Cell, 63:1357-1363.

(Continued)

*Primary Examiner* — Shin Lin Chen
(74) *Attorney, Agent, or Firm* — Kagan Binder, PLLC

(57) ABSTRACT

The present invention discloses a method for assessing the capacity of a substance to treat or prevent hepadnavirus infection. A reporter virus carrying genetic information for a first fragment of a recombinase and a reporter cell expressing a second fragment of the recombinase are used. When the reporter virus infects the reporter cell, the two fragments of the recombinase associate and excise a stop cassette that is flanked by two recombination sites and blocks the expression of a reporter gene. Accordingly, the present invention relates to a method of assessing the capacity of a substance to treat or prevent hepadnavirus infection, a hepadnavirus comprising a nucleic acid encoding a first fragment of a recombinase and a mammalian hepatocyte or hepatoma cell comprising a nucleic acid encoding a second fragment of a recombinase and a nucleic acid comprising a stop cassette flanked by two recombination sites fused to a reporter gene.

9 Claims, 21 Drawing Sheets
(6 of 21 Drawing Sheet(s) Filed in Color)

Specification includes a Sequence Listing.

(56) References Cited

PUBLICATIONS

Martin, F., et al. (1994) "The affinity-selection of a minibody polypeptide inhibitor of human interleukin-6", The EMBO Journal, 13:5303-5309.
Skerra, A. (2001) "Anticalins': a new class of engineered ligand-binding proteins with antibody-like properties", Molecular Biotechnology, 74:257-275.
Seitz, S., et al. (2016) "A Slow Maturation Process Renders Hepatitis B Virus Infectious," Cell Host & Microbe, 20:25-35.
Holt, L., et al. (2003) "Domain antibodies: proteins for therapy", Trends in Biotechnology, 21:484-490.
Van Duyne, G.D. (2014) "Cre Recombinase", Microbiology Spectrum, 3:1-19.
Shaffer, J., et al. (2022) "Floxed exon (Flexon): A flexibly positioned stop cassette for recombinase-mediated conditional gene expression", PNAS, 119(3):1-9.

\* cited by examiner

SEQUENCE LISTING

<160> NUMBER OF SEQ ID NOS: 30

<210> SEQ ID NO 1
<211> LENGTH: 325
<212> TYPE: PRT
<213> ORGANISM: Escherichia phage P1 (Bacteriophage P1)

<400> SEQUENCE: 1

```
Thr Ser Asp Glu Val Arg Lys Asn Leu Met Asp Met Phe Arg Asp Arg
1               5                   10                  15

Gln Ala Phe Ser Glu His Thr Trp Lys Met Leu Leu Ser Val Cys Arg
            20                  25                  30

Ser Trp Ala Ala Trp Cys Lys Leu Asn Asn Arg Lys Trp Phe Pro Ala
        35                  40                  45

Glu Pro Glu Asp Val Arg Asp Tyr Leu Leu Tyr Leu Gln Ala Arg Gly
    50                  55                  60

Leu Ala Val Lys Thr Ile Gln Gln His Leu Gly Gln Leu Asn Met Leu
65                  70                  75                  80
```

```
His Arg Arg Ser Gly Leu Pro Arg Pro Ser Asp Ser Asn Ala Val Ser
                85                  90                  95

Leu Val Met Arg Arg Ile Arg Lys Glu Asn Val Asp Ala Gly Glu Arg
            100                 105                 110

Ala Lys Gln Ala Leu Ala Phe Glu Arg Thr Asp Phe Asp Gln Val Arg
        115                 120                 125

Ser Leu Met Glu Asn Ser Asp Arg Cys Gln Asp Ile Arg Asn Leu Ala
    130                 135                 140

Phe Leu Gly Ile Ala Tyr Asn Thr Leu Leu Arg Ile Ala Glu Ile Ala
145                 150                 155                 160

Arg Ile Arg Val Lys Asp Ile Ser Arg Thr Asp Gly Arg Met Leu
                165                 170                 175

Ile His Ile Gly Arg Thr Lys Thr Leu Val Ser Thr Ala Gly Val Glu
                180                 185                 190

Lys Ala Leu Ser Leu Gly Val Thr Lys Leu Val Glu Arg Trp Ile Ser
            195                 200                 205

Val Ser Gly Val Ala Asp Asp Pro Asn Asn Tyr Leu Phe Cys Arg Val
        210                 215                 220

Arg Lys Asn Gly Val Ala Ala Pro Ser Ala Thr Ser Gln Leu Ser Thr
225                 230                 235                 240

Arg Ala Leu Glu Gly Ile Ala Arg Ala Gly Val Ser Ile Pro Glu Ile
                245                 250                 255

Met Gln Ala Gly Gly Trp Thr Asn Val Asn Ile Val Met Asn Tyr Ile
                260                 265                 270

Arg Asn Leu Asp Ser Glu Thr Gly Ala Met Val Arg Leu Leu Glu Asp
            275                 280                 285

Gly Asp Phe Glu Ala Thr His Arg Leu Ile Tyr Gly Ala Lys Asp Asp
        290                 295                 300

Ser Gly Gln Arg Tyr Leu Ala Trp Ser Gly His Ser Ala Arg Val Gly
305                 310                 315                 320

Ala Ala Arg Asp Met
            325

<210> SEQ ID NO 2
<211> LENGTH: 41
<212> TYPE: PRT
<213> ORGANISM: Artificial
<220> FEATURE:
<223> OTHER INFORMATION: CreN

<400> SEQUENCE: 2

Thr Ser Asp Glu Val Arg Lys Asn Leu Met Asp Met Phe Arg Asp Arg
1               5                   10                  15

Gln Ala Phe Ser Glu His Thr Trp Lys Met Leu Leu Ser Val Cys Arg
                20                  25                  30

Ser Trp Ala Ala Trp Cys Lys Leu Asn
        35                  40

<210> SEQ ID NO 3
<211> LENGTH: 354
<212> TYPE: DNA
<213> ORGANISM: Artificial
<220> FEATURE:
<223> OTHER INFORMATION: TTR Promoter
```

<400> SEQUENCE: 3

```
caggtcgagg gcactgggag gatgttgagt aagatggaaa actactgatg acccttgcag    60
agacagagta ttaggacatg tttgaacagg ggccgggcga tcagcaggta gctctagagg   120
atccccgtct gtctgcacat ttcgtagagc gagtgttccg atactctaat ctccctaggc   180
aaggttcata tttgttaagc cgtcacacag atccacaagc tcctgacagg cagcaggttt   240
ggagtcagct tggcagggat cagcagcctg ggttggaagg aggggtata aaagcccctt    300
caccaggagg taggttactt attctccttt tgttgactaa gtcaataatc agaa         354
```

<210> SEQ ID NO 4
<211> LENGTH: 7
<212> TYPE: PRT
<213> ORGANISM: Artificial
<220> FEATURE:
<223> OTHER INFORMATION: Nuclear localization sequence

<400> SEQUENCE: 4

```
Pro Lys Lys Lys Arg Lys Val
1               5
```

<210> SEQ ID NO 5
<211> LENGTH: 88
<212> TYPE: PRT
<213> ORGANISM: Artificial
<220> FEATURE:
<223> OTHER INFORMATION: N-gp40

<400> SEQUENCE: 5

```
Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Thr Gly Glu Met Asn Ile Ser Gly Gly Leu Lys Glu
65                  70                  75                  80

Gly Met Cys Leu Tyr Val Lys Glu
                85
```

<210> SEQ ID NO 6
<211> LENGTH: 5914
<212> TYPE: DNA
<213> ORGANISM: Artificial
<220> FEATURE:
<223> OTHER INFORMATION: Expression plasmid for reporter virus genome

<400> SEQUENCE: 6

```
atggacatcg acccttataa agaatttgga gctactgtgg agttactctc gttttttgcct    60
tctgacttct ttccttcagt acgagatctt ctagataccg cctcagctct gtatcgggaa   120
gccttagagt ctcctgagca ttgttcacct caccatactg cactcaggca agcaattctt   180
tgctgggggg aactaatgac tctagctacc tgggtgggtg ttaatttgga agatccagcg   240
tctagagacc tagtagtcag ttatgtcaac actaatatgg cctaaagtt caggcaactc    300
ttgtggtttc acattcttg tctcactttt ggaagagaaa cagttataga gtatttggtg    360
tctttcggag tgtggattcg cactcctcca gcttatagac caccaaatgc ccctatccta   420
```

```
tcaacacttc cggagactac tgttgttaga cgacgaggca ggtcccctag aagaagaact    480
ccctcgcctc gcagacgaag gtctcaatcg ccgcgtcgca aagatctca atctcgggaa    540 tctcaatgtt agtattcctt ggactcataa ggtggggaac tttactgggc tttattcttc    600
tactgtacct gtctttaatc ctcattggaa acaccatct tttcctaata tacatttaca    660
ccaagacatt atcaaaaaat gtgaacagtt tgtaggccca ctcacagtta atgagaaaag    720
aagattgcaa ttgattatgc ctgccaggtt ttatccaaag gttaccaaat atttaccatt    780
ggataagggt attaaacctt attatccaga acatctagtt aatcattact tccaaactag    840
acactattta cacactctat ggaaggcggg tatattatat aagagagaaa caacacatag    900
cgcctcattt tgtgggtcac catattcttg gaacaagat ctacagcatg ggcagaatc     960 tttccaccag caatcctctg ggattctttc ccgaccacca gtaggatcca gccttcagag   1020
caaacaccgc aaatccagat gggacttca atcccaacaa ggacacctgg ccagacgcca    1080
acaaggtagg agctggagca ttcgggctgc aggtcgaggg cactgggagg atgttgagta   1140
agatggaaaa ctactgatga cccttgcaga gacagagtat taggacatgt ttgaacaggg   1200
gccgggcgat cagcaggtag ctctagagga tccccgtctg tctgcacatt tcgtagagcg   1260
agtgttccga tactctaatc tccctaggca aggttcatat ttgtgtaggt tacttattct   1320
ccttttgttg actaagtcaa taatcagaat cagcaggttt ggagtcagct tggcagggat   1380
cagcagcctg ggttggaagg aggggggtata aaagccccctt caccaggaga agccgtcaca   1440
cagatccaca agctcctgac aggctcgagg attggggacc ctgcgctgaa catggagaac   1500
ggtaccatgc ccaagaagaa gaggaaggtg acctctgatg aagtcaggaa gaacctgatg   1560
gacatgttca gggacaggca ggccttctct gaacacacct ggaagatgct cctgtctgtg   1620
tgcagatcct gggctgcctg gtgcaagctg aactgcctgg acctgaagac ccaggtgcag   1680 accctcagg gcatgaagga gatcagcaac atccaggtgg cgacctggt gctgagcaac    1740 accggctaca acgaggtgct gaacgtgttc cccaagagca agaagaagag ctacaagatc   1800
accctggagg acggcaagga gatcatctgc agcgaggagc acctgttccc cacccagacc   1860
ggcgagatga acatcagcgg cggcctgaag gagggcatgt gcctgtacgt gaaggagtga   1920
aagcttgcat gtattcaatc taagcaggct ttcactttct cgccaactta caaggccttt   1980
ctgtgtaaac aatacctgaa cctttacccc gttgcccggc aacggccagg tctgtgccaa   2040
gtgtttgctg acgcaacccc cactggctgg ggcttggtca tgggccatca gcgcatgcgt   2100
ggaacctttt cggctcctct gccgatccat actgcggaac tcctagccgc ttgtttttgct   2160 cgcagcaggt ctggagcaaa cattatcggg actgataact ctgttgtcct atcccgcaaa   2220
tatacatcgt ttccatggct gctaggctgt gctgccaact ggatcctgcg cgggacgtcc   2280
tttgtttacg tcccgtcggc gctgaatcct gcggacgacc cttctcgggg tcgcttggga   2340
ctctctcgtc cccttctccg tctgccgttc cgaccgacca cggggcgcac ctctctttac   2400
gcggactccc cgtctgtgcc ttctcatctg ccggaccgtg tgcacttcgc ttcacctctg   2460
cacgtcgcat ggagaccacc gtgaacgccc accaaatatt gcccaaggtc ttacataaga   2520
ggactcttgg actctcagca atgtcaacga ccgaccttga ggcatacttc aaagactgtt   2580
tgtttaaaga ctgggaggag ttgggggagg agattaggtt aaaggtcttt gtactaggag   2640
gctgtaggca taaattggtc tgcgcaccag caccatgcaa ctttttcacc tctgcctaat   2700
catctcttgt tcatgtccta ctgttcaagc ctccaagctg tgccttgggt ggctttgggg   2760
```

```
catggacatc gacccttata aagaatttgg agctactgtg gagttactct cgttttgcc    2820
ttctgacttc tttccttcag tacgagatcc ccgggcgagc tcgctagccc tatagtgagt   2880
cgtattaata gctcgaattg atctgatcaa attccgtgta ttctatagtg tcacctaaat   2940
cgtatgtgta tgatacataa ggttatgtat taattgtagc cgcgttctaa cgacaatatg   3000
tggcctcgtg atacgcctat ttttataggt taatgtcatg ataataatgg tttcttagca   3060
ggtggcactt tcggggaaa tgtgcgcgga acccctattt gtttattttt ctaaatacat    3120
tcaaatatgt atccgctcat gagacaataa ccctgataaa tgcttcaata atattgaaaa   3180
aggaagagta tgagtattca acatttccgt gtcgccctta ttccctttt tgcggcattt    3240
tgccttcctg ttttgctca cccagaaacg ctggtgaaag taaagatgc tgaagatcag    3300
ttgggtgcac gagtgggtta catcgaactg gatctcaaca gcggtaagat ccttgagagt   3360
tttcgccccg aagaacgttt tccaatgatg agcactttta aagttctgct atgtggcgcg   3420
gtattatccc gtattgacgc cgggcaagag caactcggtc gccgcataca ctattctcag   3480
aatgacttgg ttgagtactc accagtcaca gaaaagcatc ttacgatgg catgacagta    3540
agagaattat gcagtgctgc cataaccatg agtgataaca ctgcggccaa cttacttctg   3600
acaacgatcg gaggaccgaa ggagctaacc gcttttttgc acaacatggg gatcatgta   3660
actcgccttg atcgttggga accggagctg aatgaagcca taccaaacga cgagcgtgac   3720
accacgatgc ctgtagcaat ggcaacaacg ttgcgcaaac tattaactgg cgaactactt   3780
actctagctt cccggcaaca attaatagac tggatggagg cggataaagt tgcaggacca   3840
cttctgcgct cggcccttcc ggctggctgg tttattgctg ataaatctgg agccggtgag   3900
cgtgggtctc gcggtatcat tgcagcactg gggccagatg gtaagccctc ccgtatcgta   3960
gttatctaca cgacggggag tcaggcaact atggatgaac gaaatagaca gatcgctgag   4020
ataggtgcct cactgattaa gcattggtaa ctgtcagacc aagtttactc atatatactt   4080
tagattgatt taaaacttca ttttttaattt aaaaggatct aggtgaagat cctttttgat   4140
aatctcatga ccaaaatccc ttaacgtgag ttttcgttcc actgagcgtc agaccccgta   4200
gaaaagatca aaggatcttc ttgagatcct ttttttctgc gcgtaatctg ctgcttgcaa   4260
acaaaaaaac caccgctacc agcggtggtt tgtttgccgg atcaagagct accaactctt   4320
tttccgaagg taactggctt cagcagagcg cagataccaa atactgtcct tctagtgtag   4380
ccgtagttag gccaccactt caagaactct gtagcaccgc ctacatacct cgctctgcta   4440
atcctgttac cagtggctgc tgccagtggc gataagtcgt gtcttaccgg gttggactca   4500
agacgatagt taccggataa ggcgcagcgg tcgggctgaa cggggggttc gtgcacacag   4560
cccagcttgg agcgaacgac ctacaccgaa ctgagatacc tacagcgtga gctatgagaa   4620
agcgccacgc ttcccgaagg gagaaaggcg gacaggtatc cggtaagcgg cagggtcgga   4680
acaggagagc gcacgaggga gcttccaggg ggaaacgcct ggtatcttta tagtcctgtc   4740
gggtttcgcc acctctgact tgagcgtcga ttttgtgat gctcgtcagg ggggcggagc   4800
ctatggaaaa acgccagcaa cgcggccttt ttacggttcc tggccttttg ctggccttt   4860
gctcacatgt tctttcctgc gttatcccct gattctgtgg ataaccgtat taccgccttt   4920
gagtgagctg ataccgctcg ccgcagccga acgaccgagc gcagcgagtc agtgagcgag   4980
gaagcggaag agcgcccaat acgcaaaccg cctctccccg cgcgttggcc gattcattaa   5040
tgcagctggc acgacaggtt tcccgactgg aaagcgggca gtgagcgcaa cgcaattaat   5100
gtgagttagc tcactcatta ggcaccccag gctttacact ttatgcttcc ggctcgtatg   5160
```

```
ttgtgtggaa ttgtgagcgg ataacaattt cacacaggaa acagctatga ccatgattac    5220
gccaagctgc ttgggctgca gattattgac tagttattaa tagtaatcaa ttacgggtc     5280 attagttcat agcccatata tggagttccg cgttacataa cttacggtaa atggcccgcc    5340
tggctgaccg cccaacgacc cccgcccatt gacgtcaata atgacgtatg ttcccatagt    5400
aacgccaata gggactttcc attgacgtca atgggtggag tatttacggt aaactgccca    5460
cttggcagta catcaagtgt atcatatgcc aagtacgccc cctattgacg tcaatgacgg    5520
taaatggccc gcctggcatt atgcccagta catgacctta tgggactttc ctacttggca    5580
gtacatctac gtattagtca tcgctattac catgcatggt gatgcggttt tggcagtaca    5640
tcaatgggcg tggatagcgg tttgactcac ggggatttcc aagtctccac cccattgacg    5700 tcaatggag tttgttttgc aaaatcaacg gactttcca aatgtcgta acaactccgc       5760 cccattgacg caaatgggcg gtaggcgtgt acggtgggag gtctatataa gcagaggtcg    5820
acgcaccatg caactttttc acctctgcct aatcatctct tgttcatgtc ctactgttca    5880
agcctccaag ctgtgccttg ggtggctttg ggc                                 5914
```

<210> SEQ ID NO 7
<211> LENGTH: 284
<212> TYPE: PRT
<213> ORGANISM: Artificial
<220> FEATURE:
<223> OTHER INFORMATION: CreC

<400> SEQUENCE: 7

```
Asn Arg Lys Trp Phe Pro Ala Glu Pro Glu Asp Val Arg Asp Tyr Leu
1               5                   10                  15

Leu Tyr Leu Gln Ala Arg Gly Leu Ala Val Lys Thr Ile Gln Gln His
            20                  25                  30

Leu Gly Gln Leu Asn Met Leu His Arg Arg Ser Gly Leu Pro Arg Pro
        35                  40                  45

Ser Asp Ser Asn Ala Val Ser Leu Val Met Arg Arg Ile Arg Lys Glu
    50                  55                  60

Asn Val Asp Ala Gly Glu Arg Ala Lys Gln Ala Leu Ala Phe Glu Arg
65                  70                  75                  80

Thr Asp Phe Asp Gln Val Arg Ser Leu Met Glu Asn Ser Asp Arg Cys
                85                  90                  95

Gln Asp Ile Arg Asn Leu Ala Phe Leu Gly Ile Ala Tyr Asn Thr Leu
            100                 105                 110

Leu Arg Ile Ala Glu Ile Ala Arg Ile Arg Val Lys Asp Ile Ser Arg
        115                 120                 125

Thr Asp Gly Gly Arg Met Leu Ile His Ile Gly Arg Thr Lys Thr Leu
    130                 135                 140

Val Ser Thr Ala Gly Val Glu Lys Ala Leu Ser Leu Gly Val Thr Lys
145                 150                 155                 160

Leu Val Glu Arg Trp Ile Ser Val Ser Gly Val Ala Asp Asp Pro Asn
                165                 170                 175

Asn Tyr Leu Phe Cys Arg Val Arg Lys Asn Gly Val Ala Ala Pro Ser
            180                 185                 190

Ala Thr Ser Gln Leu Ser Thr Arg Ala Leu Glu Gly Ile Phe Glu Ala
        195                 200                 205

Thr His Arg Leu Ile Tyr Gly Ala Lys Asp Asp Ser Gly Gln Arg Tyr
    210                 215                 220
```

```
Leu Ala Trp Ser Gly His Ser Ala Arg Val Gly Ala Ala Arg Asp Met
225                 230                 235                 240

Ala Arg Ala Gly Val Ser Ile Pro Glu Ile Met Gln Ala Gly Gly Trp
                245                 250                 255

Thr Asn Val Asn Ile Val Met Asn Tyr Ile Arg Asn Leu Asp Ser Glu
            260                 265                 270

Thr Gly Ala Met Val Arg Leu Leu Glu Asp Gly Asp
        275                 280

<210> SEQ ID NO 8
<211> LENGTH: 37
<212> TYPE: PRT
<213> ORGANISM: Artificial
<220> FEATURE:
<223> OTHER INFORMATION: C-gp40

<400> SEQUENCE: 8

Met Leu Lys Lys Ile Leu Lys Ile Glu Glu Leu Asp Glu Arg Glu Leu
1               5                   10                  15

Ile Asp Ile Glu Val Ser Gly Asn His Leu Phe Tyr Ala Asn Asp Ile
            20                  25                  30

Leu Thr His Asn Ser
        35

<210> SEQ ID NO 9
<211> LENGTH: 9779
<212> TYPE: DNA
<213> ORGANISM: Artificial
<220> FEATURE:
<223> OTHER INFORMATION: Reporter cell plasmid

<400> SEQUENCE: 9
gtcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtcgagg tgagccccac gttctgcttc actctcccca     420
tctccccccc ctccccaccc ccaattttgt atttatttat tttttaatta ttttgtgcag     480
cgatgggggc gggggggggg ggggggcgcg cgccaggcgg ggcggggcgg ggcgagggc      540 ggggcgggc gaggcggaga ggtgcggcgg cagccaatca gagcggcgcg ctccgaaagt     600
ttccttttat ggcgaggcgg cggcggcggc ggccctataa aaagcgaagc gcgcggcggg     660
cgggagtcgc tgcgttgcct tcgccccgtg cccgctccg cgccgcctcg cgccgcccgc      720
cccggctctg actgaccgcg ttactcccac aggtgagcgg gcgggacggc ccttctcctc     780
cgggctgtaa ttagcgcttg gtttaatgac ggctcgtttc ttttctgtgg ctgcgtgaaa     840
gccttaaagg gctccgggag ggcccctttgt gcgggggga gcggctcggg gggtgcgtgc     900
gtgtgtgtgt gcgtggggag cgccgcgtgc ggcccgcgct gcccggcggc tgtgagcgct     960 gcggcgcgg cgcggggctt tgtgcgctcc gcgtgtgcgc gaggggagcg cggccggggg     1020
cggtgccccg cggtgcgggg gggctgcgag gggaacaaag gctgcgtgcg gggtgtgtgc    1080
gtgggggggt gagcaggggg tgtgggcgcg gcggtcgggc tgtaacccc ccctgcaccc     1140
```

```
ccctccccga gttgctgagc acggcccggc ttcgggtgcg gggctccgtg cggggcgtgg    1200 cgcgggctc gccgtgccgg gcggggggtg gcggcaggtg ggggtgccgg gcggggcggg     1260
gccgcctcgg gccggggagg gctcggggga ggggcgcggc ggccccggag cgccggcggc    1320
tgtcgaggcg cggcgagccg cagccattgc cttttatggt aatcgtgcga gagggcgcag    1380
ggacttcctt tgtcccaaat ctggcggagc cgaaatctgg gaggcgccgc cgcacccccct   1440 ctagcgggcg cgggcgaagc ggtgcggcgc cggcaggaag gaaatgggcg gggagggcct    1500
tcgtgcgtcg ccgcgccgcc gtccccttct ccatctccag cctcgggggct gccgcagggg   1560 gacggctgcc ttcggggggg acggggcagg gcggggttcg gcttctgcgc gtgtgaccggc   1620 ggctctagag cctctgctaa ccatgttcat gccttcttct ttttcctaca gatccttaat    1680
taataatacg actcactata gggggtcgac ccgccaccat gatgctgaag aagatcctga    1740
agatcgagga gctggacgag agagagctga tcgacatcga ggtgagcggc aaccacctgt    1800
tctacgccaa cgacatcctg acccacaaca gcaacaggaa atggttccct gctgaacctg    1860
aggatgtgag ggactacctc ctgtacctgc aagccagagg cctggctgtg aagaccatcc    1920
aacagcacct gggccagctc aacatgctgc acaggagatc tggcctgcct cgcccttctg    1980
actccaatgc tgtgtccctg gtgatgagga gaatcagaaa ggagaatgtg gatgctgggg    2040
agagagccaa gcaggccctg gcctttgaac gcactgactt tgaccaagtc agatccctga    2100
tggagaactc tgacagatgc caggacatca ggaacctggc cttcctgggc attgcctaca    2160
acaccctgct gcgcattgcc gaaattgcca gaatcagagt gaaggacatc tcccgcaccg    2220
atggtgggag aatgctgatc cacattggca ggaccaagac cctggtgtcc acagctggtg    2280
tggagaaggc cctgtccctg ggggttacca agctggtgga gagatggatc tctgtgtctg    2340
gtgtggctga tgaccccaac aactacctgt tctgccgggt cagaaagaat ggtgtggctg    2400 cccttctgc cacctcccaa ctgtccaccc gggccctgga agggatcttt gaggccaccc    2460
accgcctgat ctatggtgcc aaggatgact ctgggcagag ataccctggcc tggtctggcc    2520 actctgccag agtgggtgct gccagggaca tggccagggc tggtgtgtcc atccctgaaa    2580
tcatgcaggc tggtggctgg accaatgtga acattgtgat gaactacatc agaaacctgg    2640
actctgagac tggggccatg gtgaggctgc tcgaggatgg ggaccccaag aagaagagga    2700
aggtgtaggt cagagctcgc tgatcagcct cgactgtgcc ttctagttgc cagccatctg    2760
ttgtttgccc ctccccgtg ccttccttga ccctggaagg tgccactccc actgtccttt     2820
cctaataaaa tgaggaaatt gcatcgcatt gtctgagtag gtgtcattct attctggggg    2880
gtggggtggg gcaggacagc aagggggagg attgggaaga caatagcagg catgctgggg    2940
atgcggtggg ctctatggct tctgaggcgg aaagaaccag ctggggctcg agatccacta    3000
gttattaata gtaatcaatt acgggtcat tagttcatag cccatatatg gagttccgcg    3060
ttacataact tacggtaaat ggcccgcctg gctgaccgcc caacgacccc cgcccattga    3120
cgtcaataat gacgtatgtt cccatagtaa cgccaatagg gactttccat tgacgtcaat    3180
gggtggacta tttacggtaa actgcccact tggcagtaca tcaagtgtat catatgccaa    3240
gtacgccccc tattgacgtc aatgacggta aatggcccgc ctggcattat gcccagtaca    3300
tgaccttatg ggactttcct acttggcagt acatctacgt attagtcatc gctattacca    3360
tgggtcgagg tgagccccac gttctgcttc actctcccca tctcccccc ctccccaccc     3420 ccaatttgt atttatttat ttttaatta ttttgtgcag cgatggggc ggggggggg       3480 ggggcgcgcg ccaggcgggg cggggcgggg cgaggggcgg ggcggggcga ggcggagagg    3540
```

```
tgcggcggca gccaatcaga gcggcgcgct ccgaaagttt cctttttatgg cgaggcggcg    3600 gcggcggcgg ccctataaaa agcgaagcgc gcggcgggcg ggagtcgctg cgttgccttc    3660
gccccgtgcc ccgctccgcg ccgcctcgcg ccgcccgccc cggctctgac tgaccgcgtt    3720
actcccacag gtgagcgggc gggacggccc ttctcctccg ggctgtaatt agcgcttggt    3780
ttaatgacgg ctcgtttctt ttctgtggct gcgtgaaagc cttaaagggc tccgggaggg    3840
ccctttgtgc gggggggagc ggctcggggg gtgcgtgcgt gtgtgtgtgc gtggggagcg    3900
ccgcgtgcgg cccgcgctgc ccggcggctg tgagcgctgc gggcgcggcg cggggctttg    3960
tgcgctccgc gtgtgcgcga ggggagcgcg gccggggggcg gtgccccgcg gtgcgggggg    4020
gctgcgaggg gaacaaaggc tgcgtgcggg gtgtgtgcgt gggggggtga gcaggggtg     4080 tgggcgcggg ggtcgggctg taaccccccc ctgcaccccc ctccccgagt tgctgagcac    4140
ggcccggctt cgggtgcggg gctccgtgcg gggcgtggcg cggggctcgc cgtgccgggc    4200 gggggggtggc ggcaggtggg ggtgccggc ggggcggggc cgcctcgggc cggggagggc    4260 tcggggagg ggcgcggcgg ccccggagcg ccggcggctg tcgaggcgcg gcgagccgca     4320
gccattgcct tttatggtaa tcgtgcgaga gggcgcaggg acttcctttg tcccaaatct    4380
ggcggagccg aaatctggga ggcgccgccg cacccctct agcgggcgcg ggcgaagcgg     4440
tgcggcgccg gcaggaagga aatgggcggg gagggccttc gtgcgtcgcc gcgccgccgt    4500
ccccttctcc atctccagcc tcggggctgc cgcagggga cggctgcctt cgggggggac     4560
ggggcagggc ggggttcggc ttctggcgtg tgaccggcgg ctctagagcc tctgctaacc    4620
atgttcatgc cttcttcttt ttcctacagc tcctgggcaa cgtgctggtt attgtgctgt    4680
ctcatcattt tggcaaagaa ttgattaatt cgagcgaacg cgtataactt cgtatagcat    4740
acattatacg aagttatctc gagtcggatt tgatctgatc aagagacagg atgaggatcg    4800
tttcgcatga ttaacaaga tggattgcac gcaggttctc cggccgcttg ggtggagagg      4860
ctattcggct atgactgggc acaacagaca atcggctgct ctgatgccgc cgtgttccgg    4920
ctgtcagcgc aggggcgccc ggttctttttt gtcaagaccg acctgtccgg tgccctgaat    4980
gaactgcagg acgaggcagc gcggctatcg tggctggcca cgacgggcgt tccttgcgca    5040
gctgtgctcg acgttgtcac tgaagcggga agggactggc tgctattggg cgaagtgccg    5100
gggcaggatc tcctgtcatc tcaccttgct cctgccgaga agtatccat catggctgat     5160 gcaatgcggc ggctgcatac gcttgatccg gctacctgcc cattcgacca ccaagcgaaa    5220
catcgcatcg agcgagcacg tactcggatg gaagccggtc ttgtcgatca ggatgatctg    5280
gacgaagagc atcaggggct cgcgccagcc gaactgttcg ccaggctcaa ggcgcgcatg    5340
cccgacggcg aggatctcgt cgtgacccat ggcgatgcct gcttgccgaa tatcatggtg    5400
gaaaatggcc gcttttctgg attcatcgac tgtggccggc tgggtgtggc ggaccgctat    5460
caggacatag cgttggctac ccgtgatatt gctgaagagc ttggcggcga atgggctgac    5520
cgcttcctcg tgctttacgg tatcgccgct cccgattcgc agcgcatcgc cttctatcgc    5580
cttcttgacg agttcttctg agcgggactc tggggttcga atgaccgac caagcgacgc    5640 ccaacctgcc atcacgagat ttcgattcca ccgccgcctt ctatgaaagg ttgggcttcg    5700
gaatcgtttt ccgggacgcc ggctggatga tcctccagcg cggggatctc atgctggagt    5760
tcttcgccca ccccatcgat aacttgttta ttgcagctta taatggttac aaataaagca    5820
atagcatcac aaatttcaca aataaagcat ttttttcact gcattctagt tgtggtttgt    5880
```

```
ccaaactcat caatgtatct tatcatgtct ggatcaaatc cgaacgcgta taacttcgta    5940
tagcatacat tatacgaagt tatctcgagt cgctcggtac gatttaaatt gaattctgca    6000
gtcgacggta ccgcgggccc gggatccacc ggtcgccacc atggcctcct ccgagaacgt    6060
catcaccgag ttcatgcgct tcaaggtgcg catggagggc accgtgaacg ccacgagtt     6120 cgagatcgag ggcgagggcg agggccgccc ctacgagggc acaacaccg tgaagctgaa     6180 ggtgaccaag ggcggccccc tgcccttcgc ctgggacatc ctgtccccc agttccagta     6240 cggctccaag gtgtacgtga agcaccccgc cgacatcccc gactacaaga agctgtcctt    6300
ccccgagggc ttcaagtggg agcgcgtgat gaacttcgag gacggcggcg tggcgaccgt    6360
gacccaggac tcctccctgc aggacggctg cttcatctac aaggtgaagt tcatcggcgt    6420
gaacttcccc tccgacgcc ccgtgatgca gaagaagacc atgggctggg aggcctccac     6480
cgagcgcctg taccccgcg acggcgtgct gaagggcgag acccacaagg ccctgaagct     6540
gaaggacggc ggccactacc tggtggagtt caagtccatc tacatggcca agaagcccgt    6600
gcagctgccc ggctactact acgtggacgc caagctggac atcacctccc acaacgagga    6660
ctacaccatc gtggagcagt acgagcgcac cgagggccgc caccacctgt cctgtagcg     6720 gccgcactcc tcaggtgcag gctgcctatc agaaggtggt ggctggtgtg ccaatgccc     6780 tggctcacaa ataccactga gatctttttc cctctgccaa aaattatggg gacatcatga    6840 agcccttga gcatctgact tctggctaat aaaggaaatt tattttcatt gcaatagtgt     6900
gttggaattt tttgtgtctc tcactcggaa ggacatatgg gagggcaaat catttaaaac    6960
atcagaatga gtatttggtt tagagtttgg caacatatgc catatgctgg ctgccatgaa    7020
caaaggtggc tataaagagg tcatcagtat atgaaacagc ccctgctgt ccattcctta     7080 ttccatagaa aagccttgac ttgaggttag attttttta tttttgttt tgtgttattt       7140 ttttctttaa catccctaaa attttcctta catgtttac tagccagatt tttcctcctc      7200
tcctgactac tcccagtcat agctgtccct cttctcttat gaagatccct cgacctgcag    7260
cccaagcttg gcgtaatcat ggtcatagct gtttcctgtg tgaaattgtt atccgctcac    7320
aattccacac aacatacgag ccggaagcat aaagtgtaaa gcctggggtg cctaatgagt    7380
gagctaactc acattaattg cgttgcgctc actgcccgct ttccagtcgg gaaacctgtc    7440
gtgccagcgg atccgcatct caattagtca gcaaccatag tcccgcccct aactccgccc    7500
atcccgcccc taactccgcc cagttccgcc cattctccgc cccatggctg actaattttt    7560
tttatttatg cagaggccga ggccgcctcg gcctctgagc tattccagaa gtagtgagga    7620
ggcttttttg gaggcctagg cttttgcaaa aagctaactt gtttattgca gcttataatg    7680
gttacaaata aagcaatagc atcacaaatt tcacaaataa agcatttttt tcactgcatt    7740
ctagttgtgg tttgtccaaa ctcatcaatg tatcttatca tgtctggatc cgctgcatta    7800
atgaatcggc caacgcgcgg ggagaggcgg tttgcgtatt gggcgctctt ccgcttcctc    7860
gctcactgac tcgctgcgct cggtcgttcg ctgcggcga cggtatcag ctcactcaaa      7920 ggcggtaata cggttatcca cagaatcagg ggataacgca ggaaagaaca tgtgagcaaa    7980
aggccagcaa aaggccagga accgtaaaaa ggccgcgttg ctggcgtttt tccataggct    8040
ccgcccccct gacgagcatc acaaaaatcg acgctcaagt caggaggtggc gaaacccgac   8100 aggactataa agataccagg cgtttccccc tggaagctcc ctcgtgcgct ctcctgttcc    8160
gaccctgccg cttaccggat acctgtccgc ctttctccct tcgggaagcg tggcgctttc    8220
tcaatgctca cgctgtaggt atctcagttc ggtgtaggtc gttcgctcca agctgggctg    8280
```

```
tgtgcacgaa ccccccgttc agcccgaccg ctgcgcctta tccggtaact atcgtcttga    8340
gtccaacccg gtaagacacg acttatcgcc actggcagca gccactggta acaggattag    8400
cagagcgagg tatgtaggcg gtgctacaga gttcttgaag tggtggccta actacggcta    8460
cactagaagg acagtatttg gtatctgcgc tctgctgaag ccagttacct tcggaaaaag    8520
agttggtagc tcttgatccg gcaaacaaac caccgctggt agcggtggtt ttttttgtttg   8580 caagcagcag attacgcgca gaaaaaaagg atctcaagaa gatcctttga tcttttctac    8640
ggggtctgac gctcagtgga acgaaaactc acgttaaggg attttggtca tgagattatc    8700
aaaaaggatc ttcacctaga tccttttaaa ttaaaaatga agttttaaat caatctaaag    8760
tatatatgag taaacttggt ctgacagtta ccaatgctta atcagtgagg cacctatctc    8820
agcgatctgt ctatttcgtt catccatagt tgcctgactc cccgtcgtgt agataactac    8880
gatacgggag ggcttaccat ctggccccag tgctgcaatg ataccgcgag acccacgctc    8940
accggctcca gatttatcag caataaacca gccagccgga agggccgagc gcagaagtgg    9000
tcctgcaact ttatccgcct ccatccagtc tattaattgt tgccgggaag ctagagtaag    9060
tagttcgcca gttaatagtt tgcgcaacgt tgttgccatt gctacaggca tcgtggtgtc    9120
acgctcgtcg tttggtatgg cttcattcag ctccggttcc caacgatcaa ggcgagttac    9180
atgatccccc atgttgtgca aaaaagcggt tagctccttc ggtcctccga tcgttgtcag    9240
aagtaagttg gccgcagtgt tatcactcat ggttatggca gcactgcata attctcttac    9300
tgtcatgcca tccgtaagat gcttttctgt gactggtgag tactcaacca agtcattctg    9360
agaatagtgt atgcggcgac cgagttgctc ttgcccggcg tcaatacggg ataataccgc    9420
gccacatagc agaactttaa aagtgctcat cattggaaaa cgttcttcgg ggcgaaaact    9480
ctcaaggatc ttaccgctgt tgagatccag ttcgatgtaa cccactcgtg cacccaactg    9540
atcttcagca tcttttactt tcaccagcgt ttctgggtga gcaaaaacag gaaggcaaaa    9600
tgccgcaaaa aagggaataa gggcgacacg gaaatgttga atactcatac tcttcctttt    9660
tcaatattat tgaagcattt atcagggtta ttgtctcatg agcggataca tatttgaatg    9720
tatttagaaa aataaacaaa taggggttcc gcgcacattt ccccgaaaag tgccacctg    9779
```

<210> SEQ ID NO 10
<211> LENGTH: 34
<212> TYPE: DNA
<213> ORGANISM: Artificial
<220> FEATURE:
<223> OTHER INFORMATION: loxP

<400> SEQUENCE: 10
ataacttcgt atagcataca ttatacgaag ttat                                 34

<210> SEQ ID NO 11
<211> LENGTH: 34
<212> TYPE: DNA
<213> ORGANISM: Artificial
<220> FEATURE:
<223> OTHER INFORMATION: loxP

<400> SEQUENCE: 11
ataacttcgt ataatgtata ctatacgaag ttat                                 34

<210> SEQ ID NO 12
<211> LENGTH: 34
<212> TYPE: DNA

```
<213> ORGANISM: Artificial
<220> FEATURE:
<223> OTHER INFORMATION: loxP

<400> SEQUENCE: 12
ataacttcgt ataatgtgta ctatacgaag ttat                                34

<210> SEQ ID NO 13
<211> LENGTH: 34
<212> TYPE: DNA
<213> ORGANISM: Artificial
<220> FEATURE:
<223> OTHER INFORMATION: loxP

<400> SEQUENCE: 13
ataacttcgt ataaagtatc ctatacgaag ttat                                34

<210> SEQ ID NO 14
<211> LENGTH: 34
<212> TYPE: DNA
<213> ORGANISM: Artificial
<220> FEATURE:
<223> OTHER INFORMATION: loxP

<400> SEQUENCE: 14
ataacttcgt ataagaaacc atatacgaag ttat                                34

<210> SEQ ID NO 15
<211> LENGTH: 34
<212> TYPE: DNA
<213> ORGANISM: Artificial
<220> FEATURE:
<223> OTHER INFORMATION: loxP

<400> SEQUENCE: 15
ataacttcgt atataatacc atatacgaag ttat                                34

<210> SEQ ID NO 16
<211> LENGTH: 34
<212> TYPE: DNA
<213> ORGANISM: Artificial
<220> FEATURE:
<223> OTHER INFORMATION: loxP

<400> SEQUENCE: 16
ataacttcgt ataagataga atatacgaag ttat                                34

<210> SEQ ID NO 17
<211> LENGTH: 34
<212> TYPE: DNA
<213> ORGANISM: Artificial
<220> FEATURE:
<223> OTHER INFORMATION: loxP

<400> SEQUENCE: 17
ataacttcgt atacgatacc atatacgaag ttat                                34

<210> SEQ ID NO 18
<211> LENGTH: 34
<212> TYPE: DNA
<213> ORGANISM: Artificial
<220> FEATURE:
<223> OTHER INFORMATION: loxP

<400> SEQUENCE: 18
taccgttcgt ataatgtatg ctatacgaag ttat                                34
```

```
<210> SEQ ID NO 19
<211> LENGTH: 34
<212> TYPE: DNA
<213> ORGANISM: Artificial
<220> FEATURE:
<223> OTHER INFORMATION: loxP

<400> SEQUENCE: 19
ataacttcgt ataatgtatg ctatacgaac ggta                               34

<210> SEQ ID NO 20
<211> LENGTH: 155
<212> TYPE: DNA
<213> ORGANISM: Artificial
<220> FEATURE:
<223> OTHER INFORMATION: SV40 polyA Terminator

<400> SEQUENCE: 20
aacttgttta ttgcagctta taatggttac aaataaagca atagcatcac aaatttcaca    60
aataaagcat ttttttcact gcattctagt tgtggtttgt ccaaactcat caatgtatct   120
tatcatgtct ggatcgtggt ttgtccaaac tcatc                             155

<210> SEQ ID NO 21
<211> LENGTH: 123
<212> TYPE: DNA
<213> ORGANISM: artificial sequence
<220> FEATURE:
<223> OTHER INFORMATION: N-terminal fragment of Cre recombinase

<400> SEQUENCE: 21
acctctgatg aagtcaggaa gaacctgatg gacatgttca gggacaggca ggccttctct    60
gaacacacct ggaagatgct cctgtctgtg tgcagatcct gggctgcctg gtgcaagctg   120
aac                                                                 123

<210> SEQ ID NO 22
<211> LENGTH: 852
<212> TYPE: DNA
<213> ORGANISM: Artificial Sequence
<220> FEATURE:
<223> OTHER INFORMATION: C-terminal fragment of Cre recombinase

<400> SEQUENCE: 22
aacaggaaat ggttccctgc tgaacctgag gatgtgaggg actacctcct gtacctgcaa    60
gccagaggcc tggctgtgaa gaccatccaa cagcacctgg ccagctcaa catgctgcac   120 aggagatctg gcctgcctcg cccttctgac tccaatgctg tgtccctggt gatgaggaga   180
atcagaaagg agaatgtgga tgctggggag agagccaagc aggccctggc ctttgaacgc   240
actgactttg accaagtcag atccctgatg gagaactctg acagatgcca ggacatcagg   300
aacctggcct tcctgggcat tgcctacaac accctgctgc gcattgccga aattgccaga   360
atcagagtga aggacatctc ccgcaccgat ggtgggagaa tgctgatcca cattggcagg   420
accaagaccc tggtgtccac agctggtgtg gagaaggccc tgtccctggg ggttaccaag   480
ctggtggaga gatggatctc tgtgtctggt gtggctgatg accccaacaa ctacctgttc   540
tgccgggtca gaaagaatgg tgtggctgcc ccttctgcca cctcccaact gtccacccgg   600
gccctggaag ggatctttga ggccaccac cgcctgatct atggtgccaa ggatgactct   660
gggcagagat acctggcctg gtctggccac tctgccagag tgggtgctgc cagggacatg   720
```

```
gccagggctg gtgtgtccat ccctgaaatc atgcaggctg gtggctggac caatgtgaac    780
attgtgatga actacatcag aaacctggac tctgagactg gggccatggt gaggctgctc    840
gaggatgggg ac                                                         852

<210> SEQ ID NO 23
<211> LENGTH: 18
<212> TYPE: DNA
<213> ORGANISM: Artificial
<220> FEATURE:
<223> OTHER INFORMATION: HBV core-specific primer

<400> SEQUENCE: 23
ttcaggcaac tcttgtgg                                                   18

<210> SEQ ID NO 24
<211> LENGTH: 18
<212> TYPE: DNA
<213> ORGANISM: Artificial
<220> FEATURE:
<223> OTHER INFORMATION: HBV core-specific primer

<400> SEQUENCE: 24
tgaggcgcta tgtgttgt                                                   18

<210> SEQ ID NO 25
<211> LENGTH: 20
<212> TYPE: DNA
<213> ORGANISM: Artificial
<220> FEATURE:
<223> OTHER INFORMATION: HBV x-specific primer

<400> SEQUENCE: 25
atggctgcta ggctgtgctg                                                 20

<210> SEQ ID NO 26
<211> LENGTH: 20
<212> TYPE: DNA
<213> ORGANISM: Artificial
<220> FEATURE:
<223> OTHER INFORMATION: HBV x-specific primer

<400> SEQUENCE: 26
tggtgcgcag accaatttat                                                 20

<210> SEQ ID NO 27
<211> LENGTH: 22
<212> TYPE: DNA
<213> ORGANISM: Artificial
<220> FEATURE:
<223> OTHER INFORMATION: HBV-specific DNA probe

<400> SEQUENCE: 27
ttctagatac cgcctcagct ct                                              22

<210> SEQ ID NO 28
<211> LENGTH: 20
<212> TYPE: DNA
<213> ORGANISM: Artificial
<220> FEATURE:
<223> OTHER INFORMATION: HBV-specific DNA probe

<400> SEQUENCE: 28
tggtgcgcag accaatttat                                                 20
```

```
<210> SEQ ID NO 29
<211> LENGTH: 20
<212> TYPE: DNA
<213> ORGANISM: Artificial
<220> FEATURE:
<223> OTHER INFORMATION: Neomycin fwd primer

<400> SEQUENCE: 29
caacgtgctg gttattgtgc                                               20

<210> SEQ ID NO 30
<211> LENGTH: 19
<212> TYPE: DNA
<213> ORGANISM: Artificial
<220> FEATURE:
<223> OTHER INFORMATION: Neomycin rev primer

<400> SEQUENCE: 30
ggtaccgtcg actgcagat                                                19
```

RECOMBINANT HBV REPORTER SYSTEM

This application claims the benefit of priority of U.S. Provisional Application No. 62/719,393, filed Aug. 17, 2018, the entire contents of which is incorporated herein by reference.

This application incorporates by reference the sequence listing contained in the ASCII text file being submitted concurrently herewith and titled IPM0087US_Sequence Listing_ST25 created on Aug. 14, 2019 and having a size of 34 kilobytes and is incorporated herein by reference.

TECHNICAL FIELD

The present invention discloses a method for assessing the capacity of a substance to treat or prevent hepadnavirus infection. Accordingly, the present invention relates to a method of assessing the capacity of a substance to treat or prevent hepadnavirus infection, a hepadnavirus comprising a nucleic acid encoding a first fragment of a recombinase and a mammalian hepatocyte or hepatoma cell comprising a nucleic acid encoding a second fragment of a recombinase and a nucleic acid comprising a stop cassette flanked by two recombination sites fused to a reporter gene.

BACKGROUND

Hepatitis B virus (hereinafter referred to as HBV) is a liver-specific virus that causes hepatitis B in an infected person. More than 240 million people worldwide are infected with HBV. According to current estimates, more than 680,000 people die each year from hepatitis B or the consequences thereof. Despite an existing vaccination against HBV, these numbers illustrate the need for a new therapy. However, there this is no effective and reliable reporter system for following whether a new medicament or therapy could prevent infection of a cell by HBV.

Current available recombinant reporter HBV (rHBV) systems have several limitations and therefore hinder the usage of such system to perform studies or screenings. First, due to the compact organization of the HBV genome, the size of cargo is restricted. Moreover, introducing a foreign sequence into HBV vector might inhibit the replication of HBV. Second, the replication of recombinant HBV is inefficient. This results in lower yield of rHBV compared to that of wild-type HBV. As a consequence, achieving a high infection rate in order to have higher expression of reporter genes is challenging. Third, the expression of reporter genes is based on the stability of HBV cccDNA, which is known to be lost over time in cell culture models. The technical problem of the invention is therefore to overcome the issues outlined above.

SUMMARY

The technical problem is solved by the subject-matter as defined in the claims. The inventors surprisingly found that is possible to use a split recombinase reporter system in a recombinant HBV together with a reporter cell (see Examples). Here, a first fragment of a recombinase such as an N-terminal fragment of the Cre recombinase in integrated into the genome of the reporter virus such as HBV (see Example 1) and a second fragment of the recombinase is expressed in the reporter cell, e.g. a human hepatocyte (see Example 2). When the reporter cell is infected, the first fragment encoded by the genome of the reporter virus is expressed and the two fragments of the recombinase associate to form an active recombinase. The reporter cell comprises a stop cassette flanked by two recombination sites fused to a reporter gene, wherein the presence of the stop cassette suppresses expression of the reporter gene. The stop cassette is then excised by the recombinase to permanently enable the expression of the reporter gene (see Example 3).

Accordingly, the present invention relates to a method of assessing the capacity of a substance to treat or prevent hepadnavirus infection, to a hepadnavirus comprising a nucleic acid encoding a first fragment of a recombinase and to a hepatocyte or hepatoma cell comprising a nucleic acid encoding a second fragment of a recombinase and a nucleic acid comprising a stop cassette flanked by two recombination sites fused to a reporter gene, wherein the presence of the stop cassette suppresses expression of the reporter gene.

Preferably, the hepadnavirus and/or the reporter virus is a hepatitis B virus.

Preferably, the reporter virus comprises a genome comprising a gene encoding an N-terminal fragment of Cre recombinase.

Preferably, the reporter cell is an animal cell, preferably a mammalian cell.

Preferably, the reporter cell comprises a sodium taurocholate cotransporting polypeptide (NTCP).

Preferably, the reporter cell is a hepatocyte and/or a hepatoma cell.

Preferably, the recombinase is Cre recombinase.

Preferably, the first fragment of the recombinase is CreN.

Preferably, the first fragment of the recombinase has an amino acid sequence set forth in SEQ ID NO: 2.

Preferably, the second fragment of the recombinase is CreC.

Preferably, the second fragment of the recombinase has an amino acid sequence set forth in SEQ ID NO: 7.

Preferably, the recombination site is a loxP site.

Preferably, the stop cassette is a transcriptional or translational stop cassette.

Preferably, the reporter gene encodes a detectable gene product.

The present invention further relates to a hepadnavirus comprising a nucleic acid encoding a first fragment of a recombinase.

Preferably, the hepadnavirus is a hepatitis B virus.

Preferably, the first fragment of the recombinase is CreN.

In addition, the present invention relates to a mammalian hepatocyte or hepatoma cell comprising a nucleic acid encoding a second fragment of a recombinase and a nucleic acid comprising a stop cassette flanked by two recombination sites fused to a reporter gene, wherein the presence of the stop cassette suppresses expression of the reporter gene.

Preferably, the second fragment of the recombinase is CreC.

Preferably, the recombination site is a loxP site.

BRIEF DESCRIPTION OF THE DRAWINGS

The patent or application file contains at least one drawing executed in color. Copies of this patent or patent application with color drawing(s) will be provided by the Office upon request and payment of the necessary fee.

The invention will be better understood with reference to the detailed description when considered in conjunction with the non-limiting examples and the accompanying drawings, in which.

(A) The Co-InCreN was placed in the rHBV vector, whereas the Co-InCreC together with the Cre-induced DsRed cassette was integrated into the genome of HepG2-NTCP cells. (B) The PreS/S region of the 1.1-fold HBV vector was replaced by the TTR promoter/enhancer and the Co-InCreN coding sequence.

Figure 2:
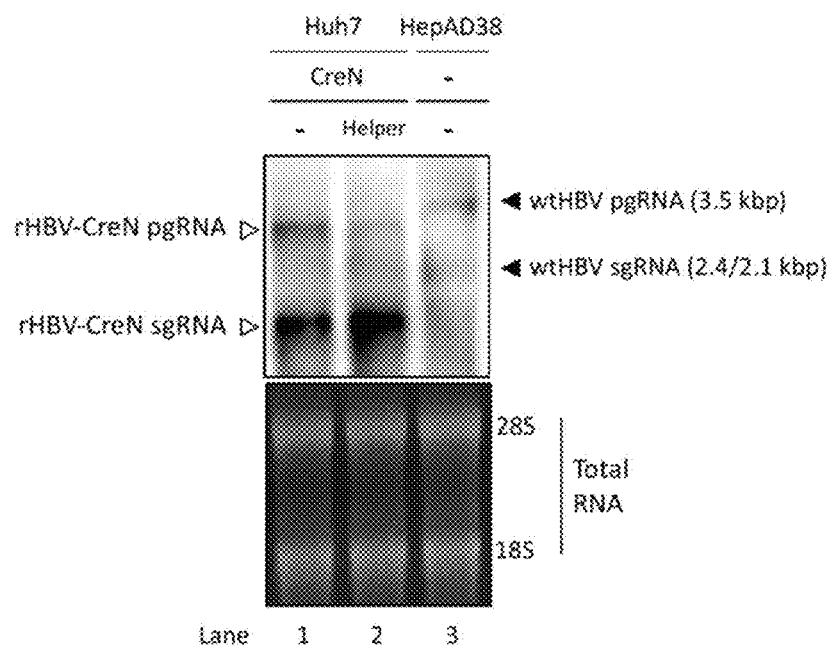

FIG. 2 shows the expression of rHBV-CreN vector and the HBV RNA. Huh7 cells were transfected with rHBV-CreN vector (CreN) and HBV helper plasmid (Helper). HepAD38 cells, a wtHBV replicating cell line, served as the positive control. RNA extracted from the cells was analyzed by Northern blot.

Figure 3:
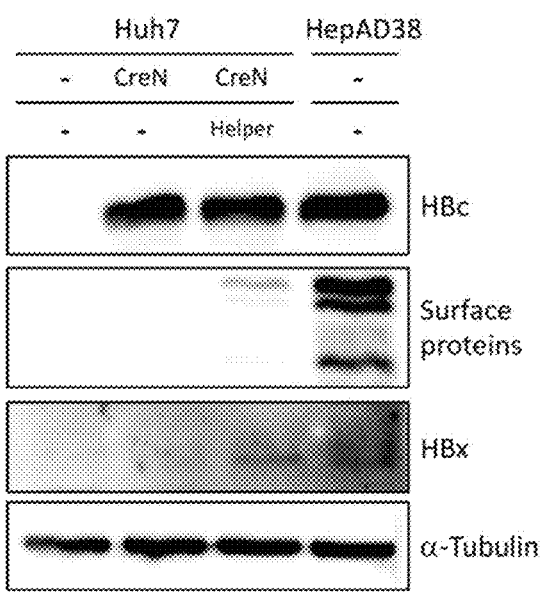

FIG. 3 shows the expression of HBV viral proteins derived from rHBV-CreN vector and the helper plasmid. Huh7 cells were transfected with rHBV-CreN vector (CreN) alone or together with an HBV helper plasmid (Helper). HepAD38 cells, an wtHBV-producing cell line was used as positive control. Protein lysates from the cells were analyzed by Western blot.

Figure 4:
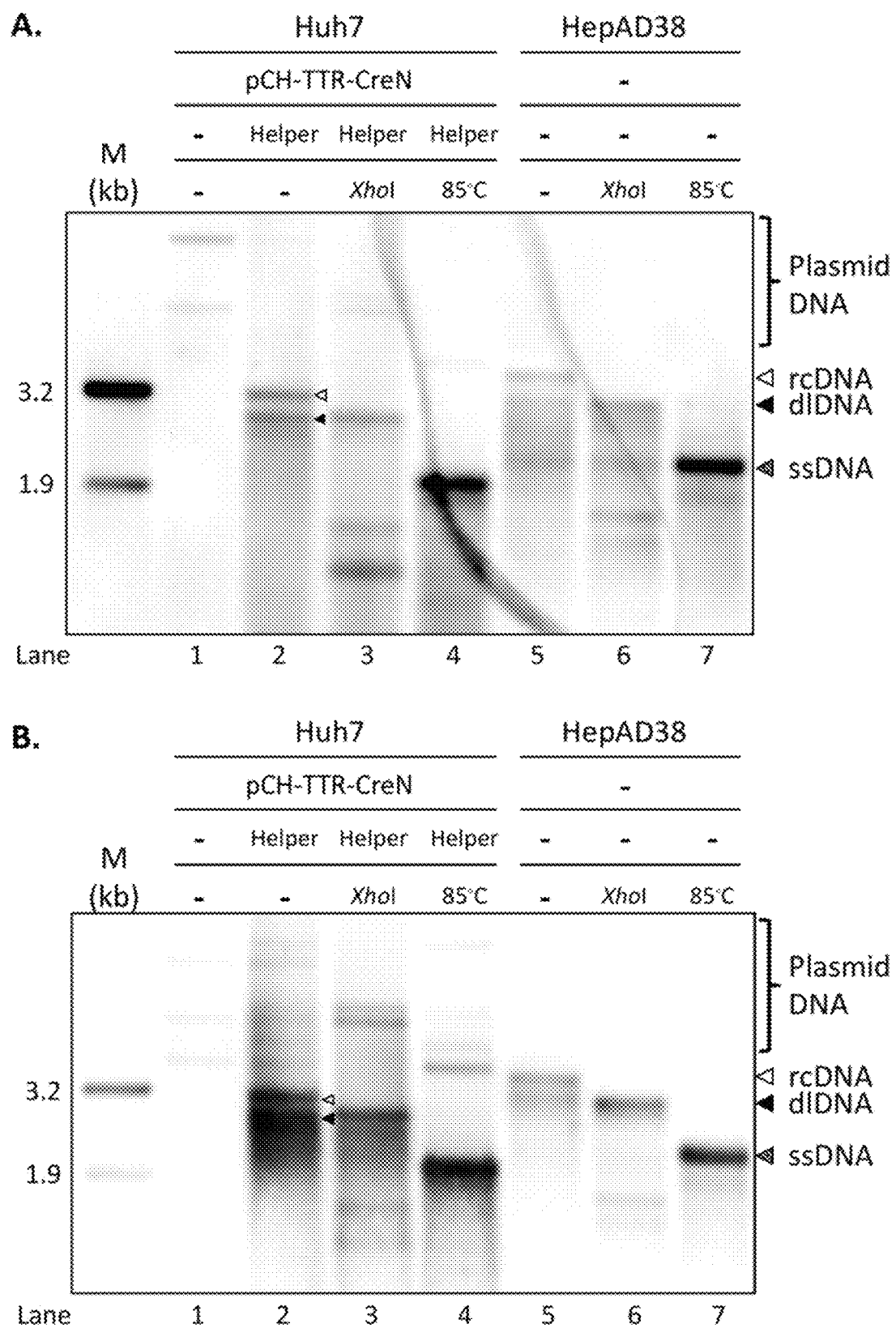

FIG. 4 shows genome structure of rHBV-CreN. Huh7 cells were transfected with rHBV-CreN vector (pCH-TTR-CreN) and HBV helper plasmid (Helper). HepAD38 cells, a wtHBV replicating cell line, was served as positive control. DNA extracted from capsids in the cells (A) and virus in the supernatant (B) was analyzed by Southern blot. The DNA species were further confirmed by digesting the DNA samples with XhoI or by heating the DNA samples to 85° C. Open arrows indicate the rc-form of HBV DNA. Open triangles indicate the rcDNA. Filled triangles indicate the dslDNA. Dotted triangles indicate the ssDNA.

Figure 5:
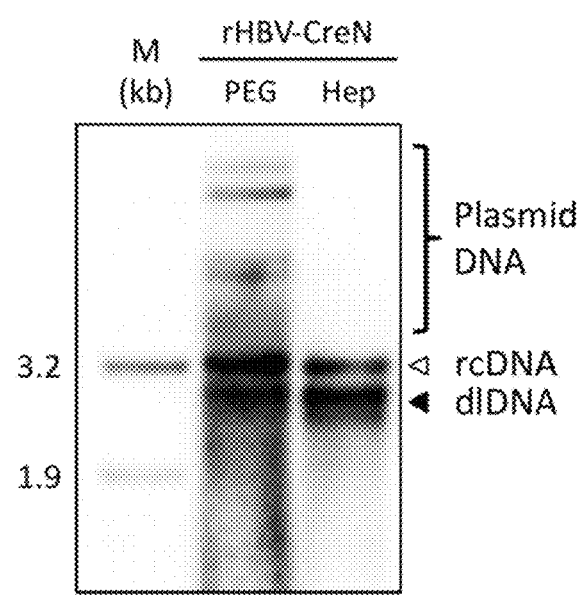

FIG. 5 shows the purification of rHBV-CreN. Huh7 cells were co-transfected with rHBV-CreN vector and HBV helper plasmid. The supernatant containing virus was either subjected to PEG precipitation (PEG) or purified by heparin affinity chromatography coupling with rDNase on-column digestion (Hep). DNA extracted from the purified viral stocks was analyzed by Southern blot.

Figure 6:
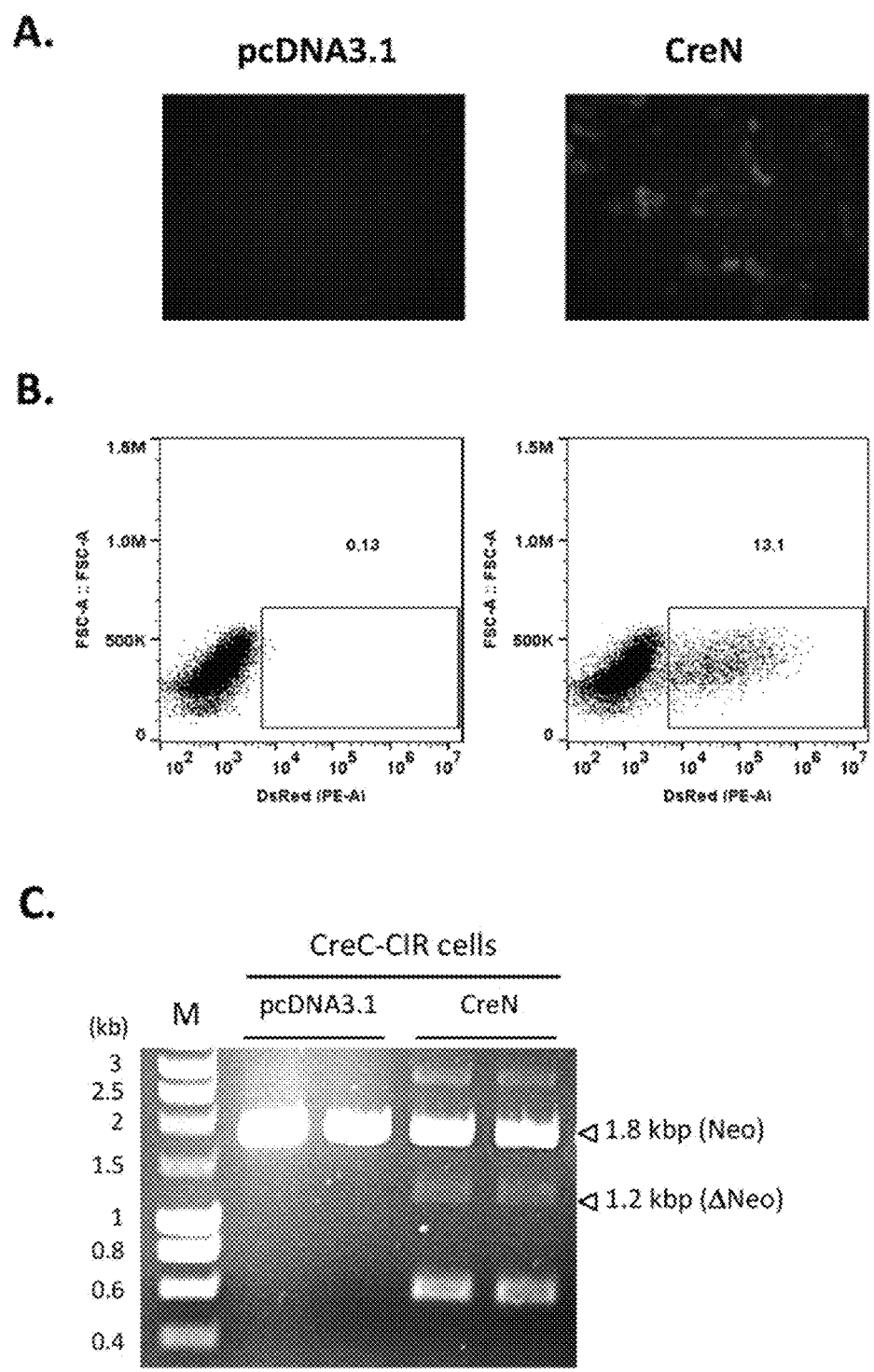

FIG. 6 shows the functional complementation of split Cre in HepG2-NTCP-CreC-CIR cells (CreC/CIR). CreC/CIR cells were transfected with either control plasmid (pcDNA3.1) or plasmid expressing N-terminal Cre (CreN). Red fluorescence was measured by fluorescence microscopy (A). The numbers of DsRed-positive cells were determined by flow cytometry (B). DNA extracted from the cells was amplified by PCR using primers binding to the loxP-Neo-pA-loxP cassette. The PCR products were then subjected to agarose gel electrophoresis (C). Neo indicates the PCR products containing the loxP-Neo-pA-loxP cassette. ΔNeo indicates the PCR products without the loxP-Neo-pA-loxP cassette.

Figure 7:
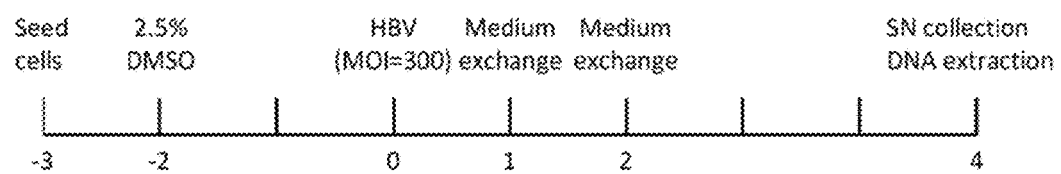
Figure 7:
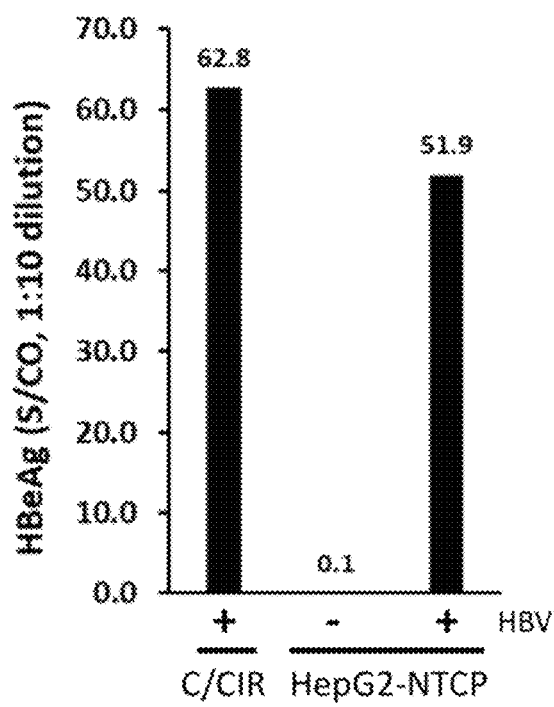
Figure 7:
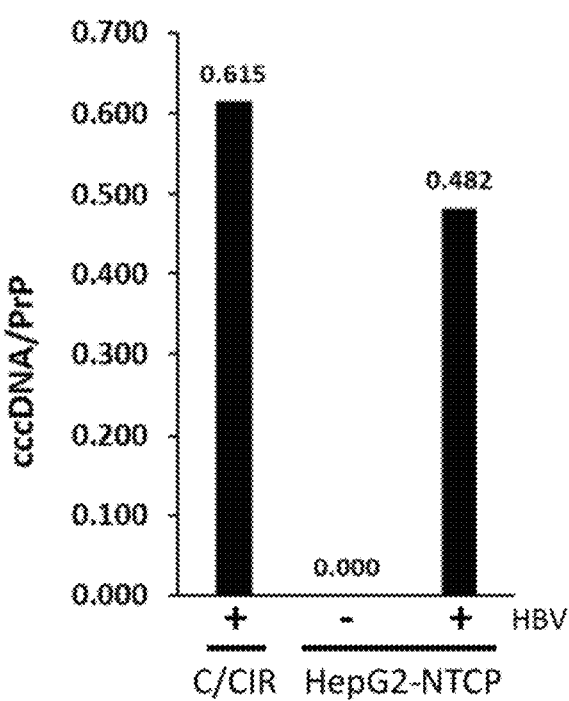

FIG. 7 shows the infectivity of wtHBV in CreC/CIR cells. The CreC/CIR cells were infected with wtHBV, the experiment was conducted according to the scheme (A). Supernatant was collected for measuring the HBeAg level by HBeAg ELISA (B). DNA was extracted from the cells and the level of cccDNA was determined by qPCR (C).

Figure 8:
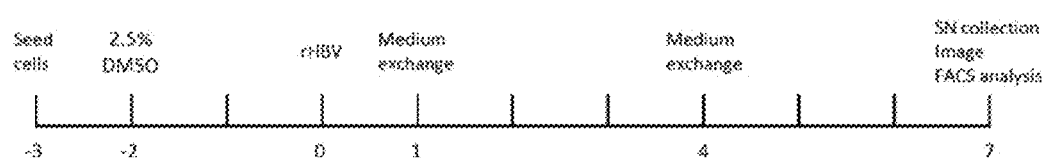
Figure 8:
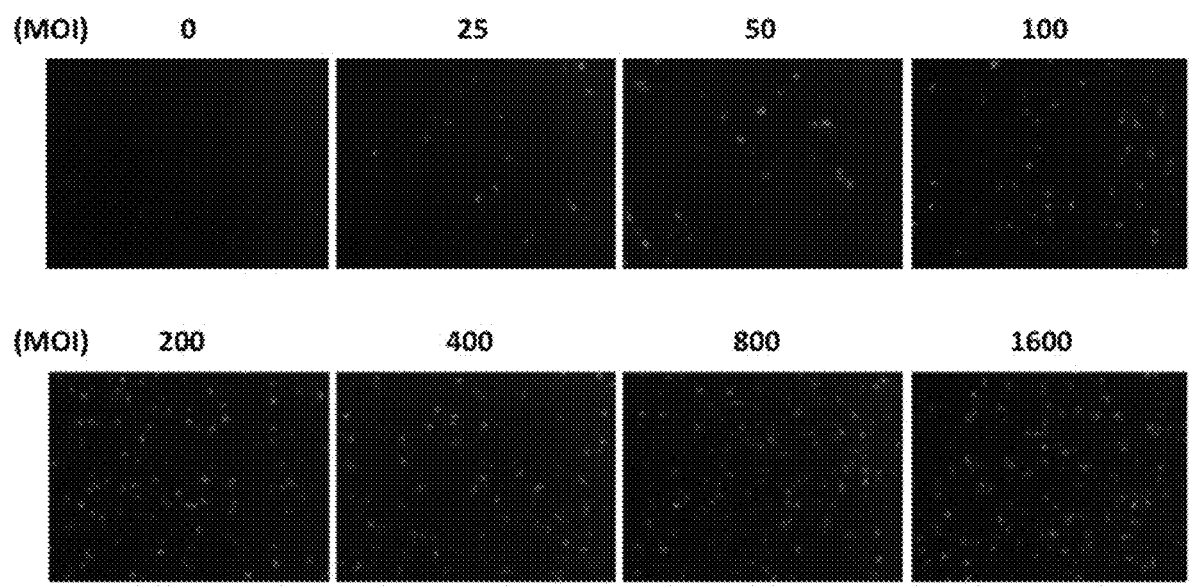
Figure 8:
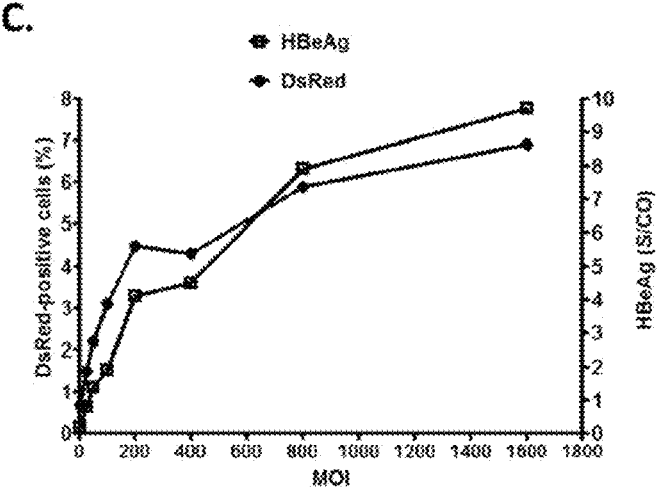

FIG. 8 shows the expression of DsRed upon rHBV-CreN infection in CreC/CIR cells. CreC/CIR cells were infected with rHBV-CreN using different MOI, the experiment was conducted according to the scheme (A). Fluorescent signal was detected by fluorescence microscopy (B). The number of DsRed-positive cells was determined by flow cytometry and the amount of HBeAg in the supernatant was analyzed by HBeAg ELISA (C).

Figure 9:
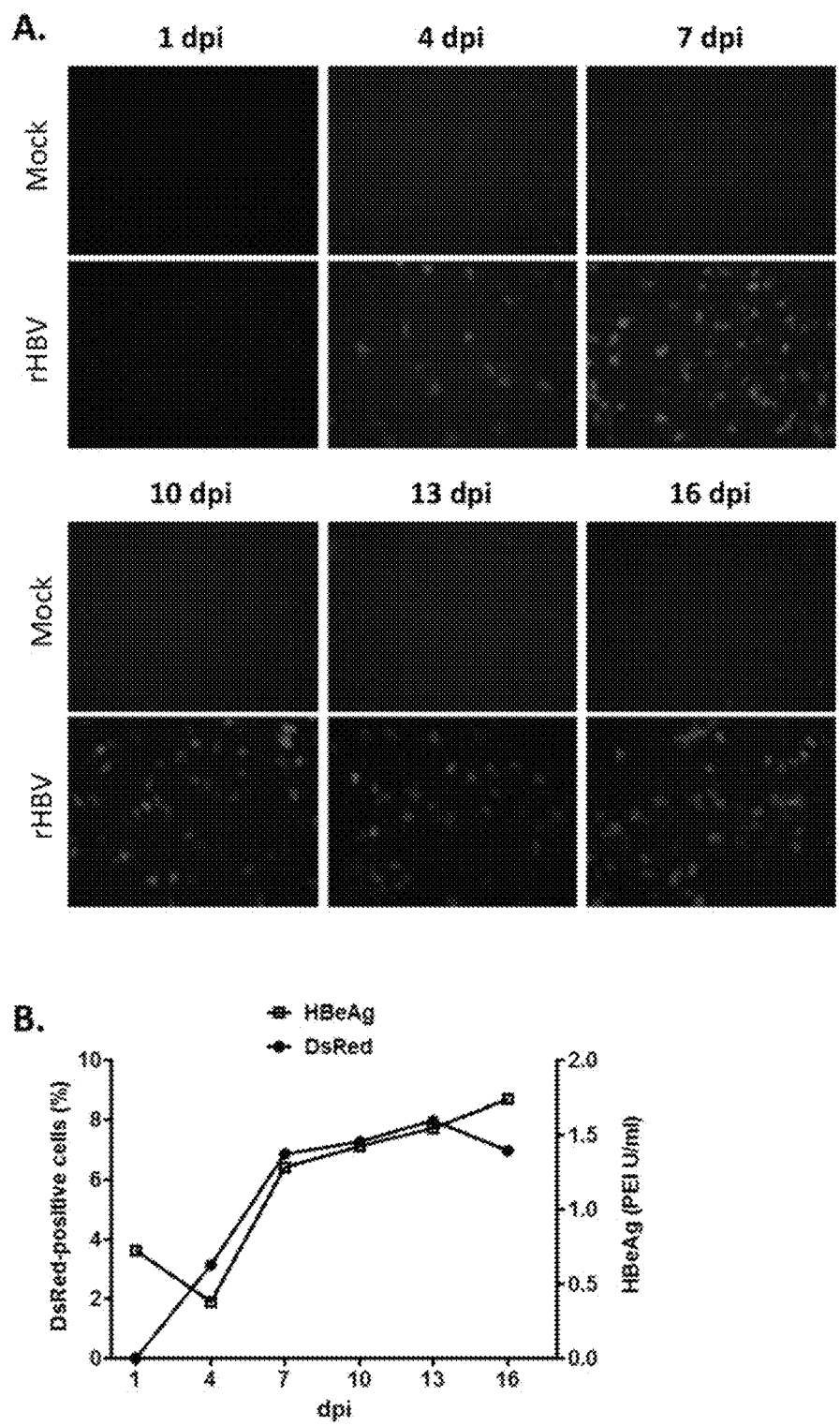

FIG. 9 shows the kinetic of rHBV-CreN infection in CreC/CIR cells. CreC/CIR cells were incubated with (rHBV-CreN) or without (Mock) the recombinant HBV for 24 hours. At the indicated time points, cells were imaged by fluorescence microscopy and analyzed by flow cytometry (A, B). Supernatants were collected at the same time and HBeAg levels were determined by HBeAg ELISA (B).

Figure 10:
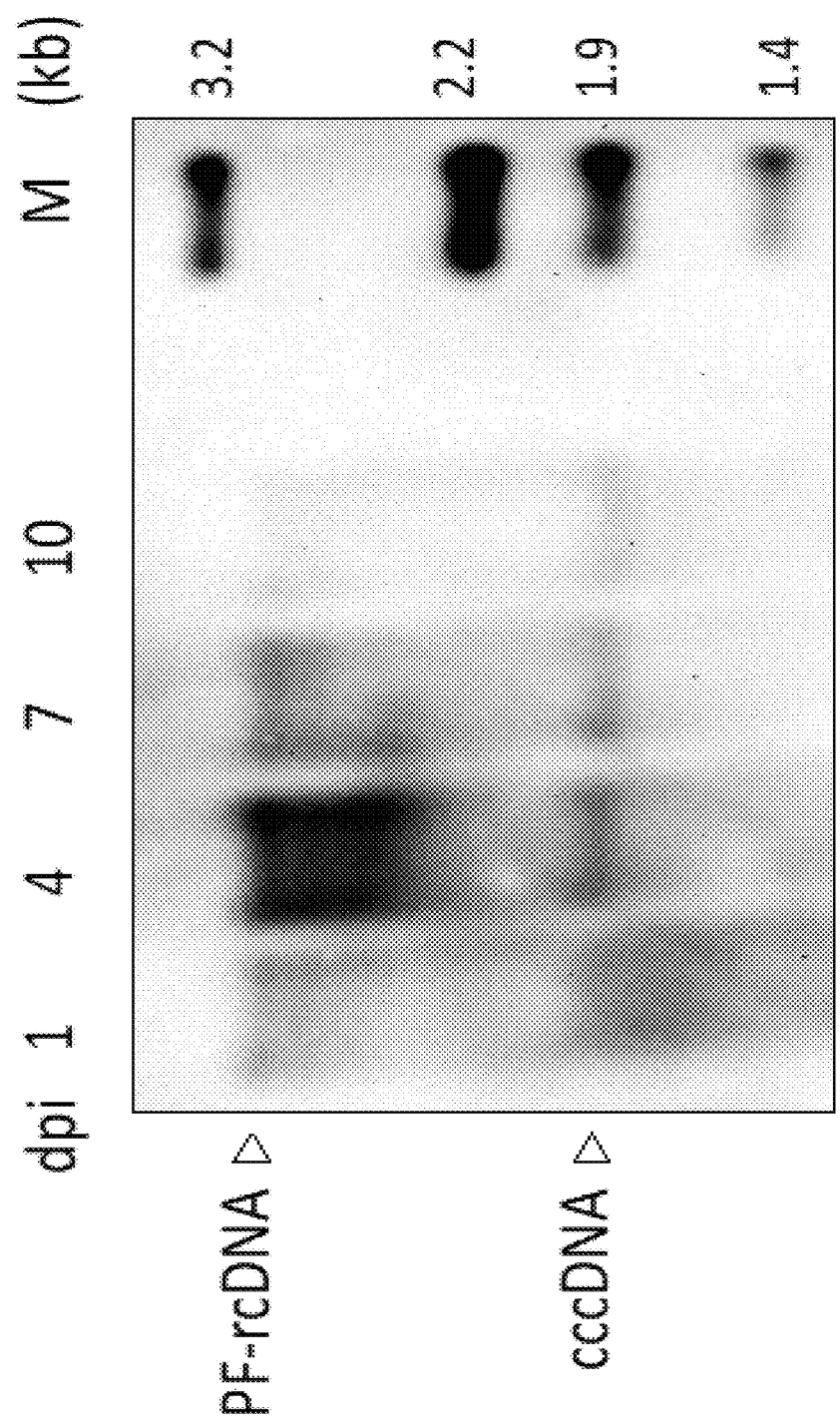

FIG. 10 shows the cccDNA formation in CreC/CIR cells infected with rHBV-CreN. CreC/CIR cells were infected with rHBV-CreN. The infected cells were harvested after infection on day 1, 4, 7, and 10. DNA was isolated by using Hirt method and subsequently analyzed by Southern blot.

Figure 11:
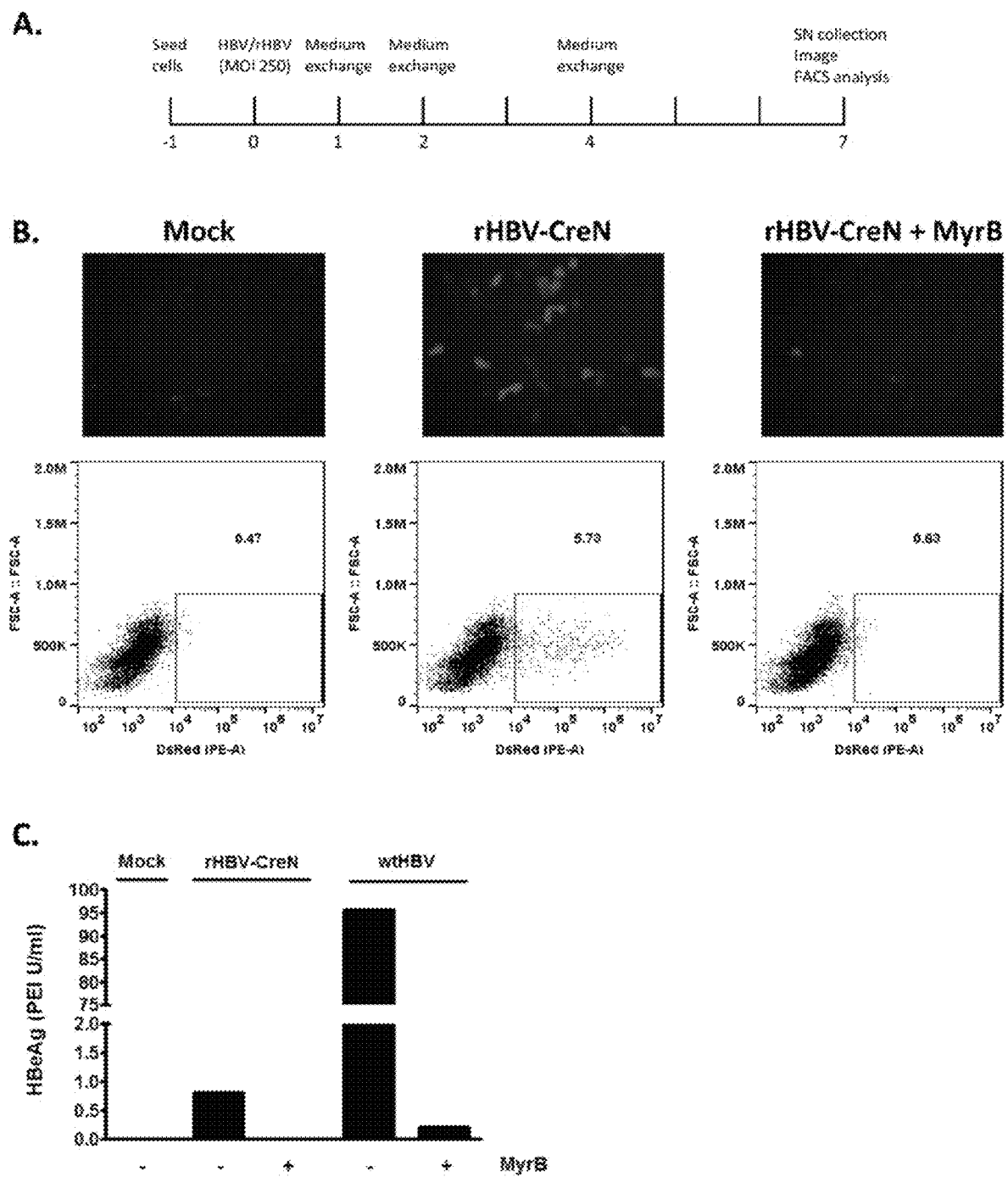

FIG. 11 shows the effect of MyrB on rHBV-CreN infection. CreC/CIR cells were infected either with rHBV-CreN or wtHBV. In addition, MyrB was added to the inoculums. Cells receiving PEG alone served as a control (mock). The experiment was conducted according to the scheme (A). After 7 days of infection, the fluorescent images of the cells were taken, and the cells were then analyzed by flow cytometry (B). The supernatant of the cells was analyzed by HBeAg ELISA (C).

Figure 12:
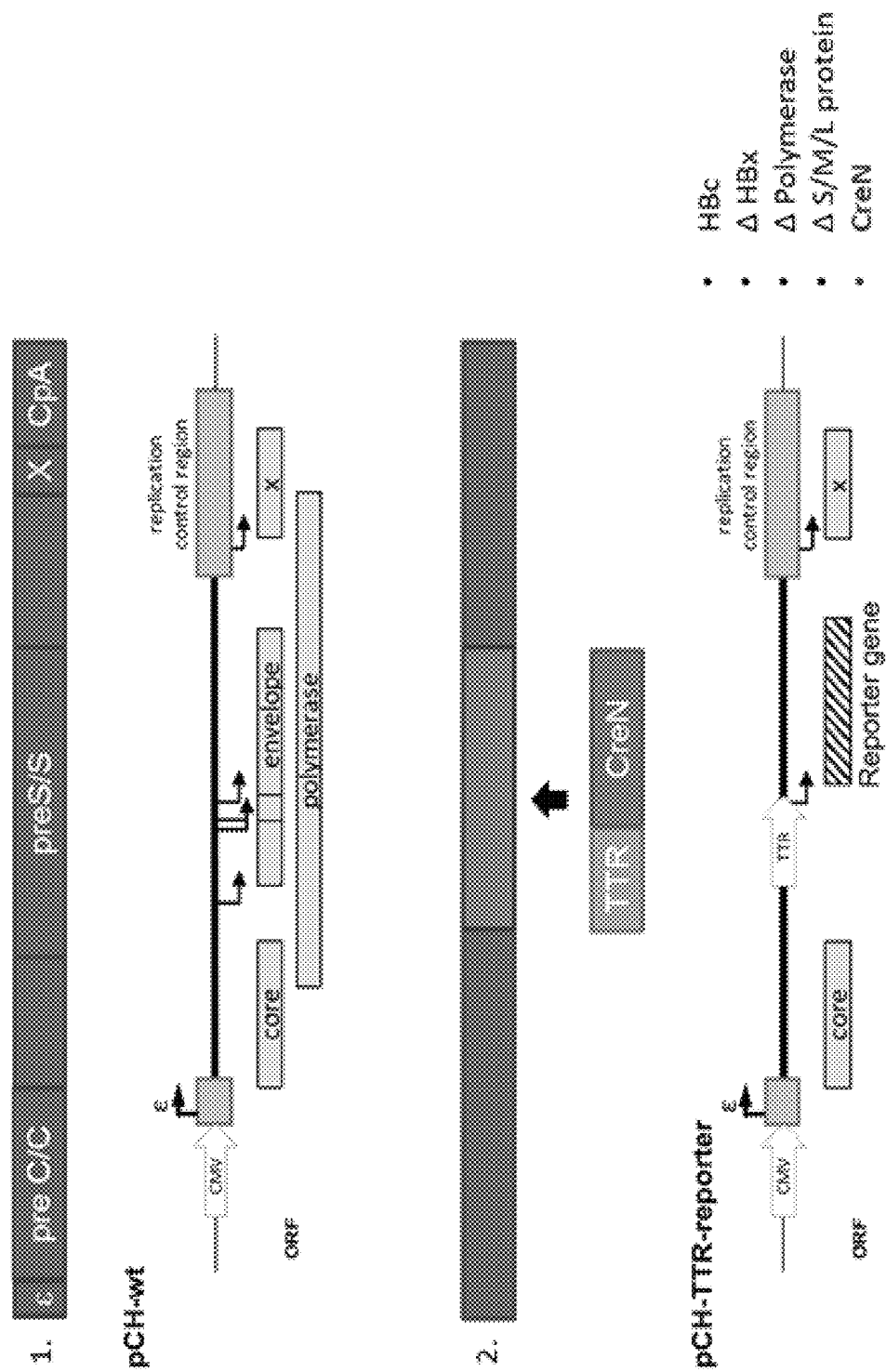

FIG. 12 shows the organization of the HBV genome of the wt and the recombinant HBV. In the recombinant reporter virus genome, the preS/S region has been replaced by a first fragment of the recombinase such as a CreN fragment under the control of a TTR promoter/enhancer.

Figure 13:
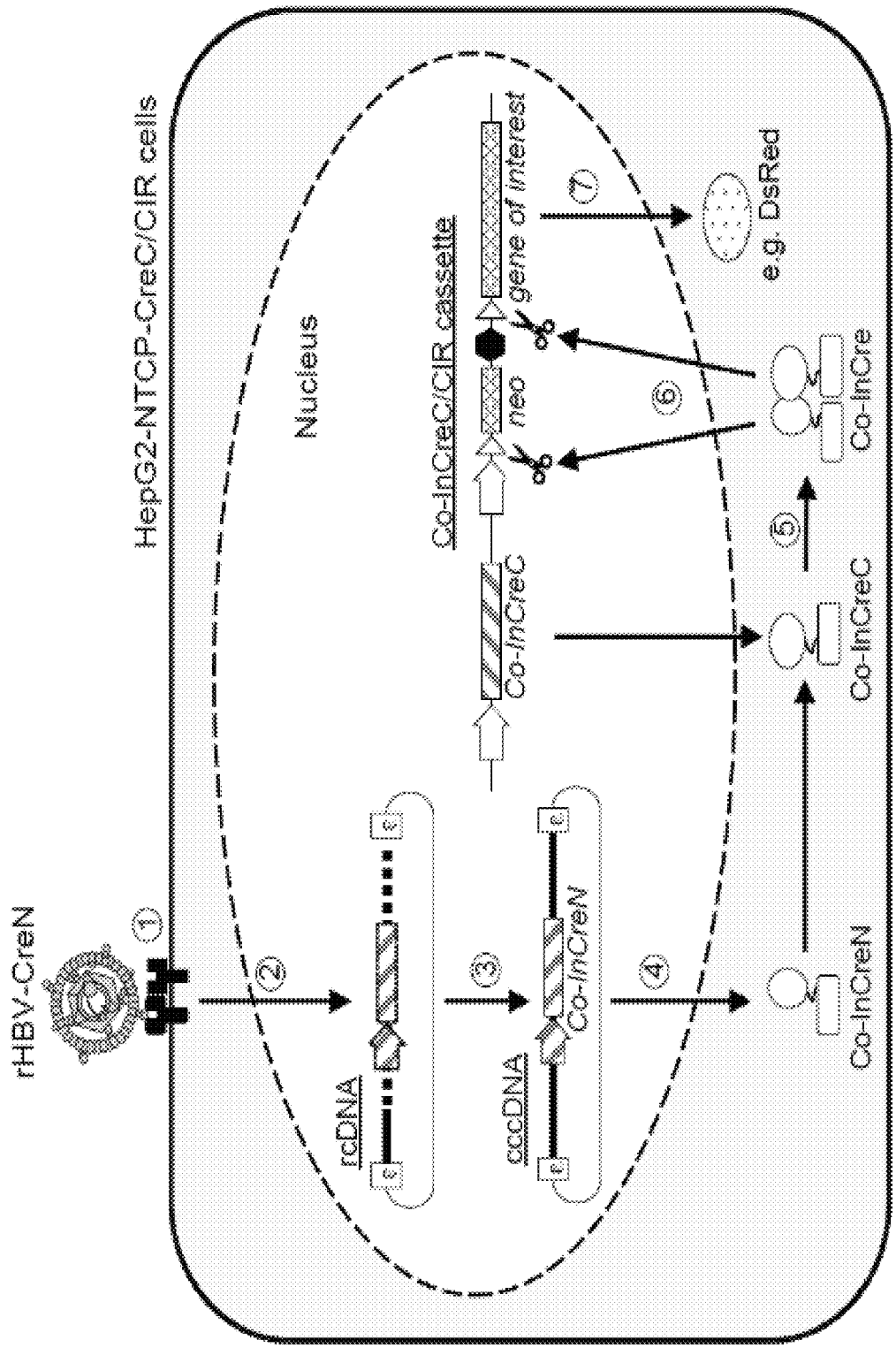

FIG. 13 shows the rHBV-CreN reporter system. Step 1: rHBV-CreN infects HepG2-NTCP-CreC/CIR cells via HBV receptors. Step 2: The rHBV genome is imported into the nucleus. Step 3: The relaxed circular (rcDNA) rHBV genome is converted into a cccDNA transcription template. Step 4: Co-InCreN is expressed using cccDNA as its transcription template. Step 5: Co-lnCre is reconstituted by association with Co-InCreC constantly expressed in HepG2-NTCP-CreC/CIR cells. Step 6: The floxed stop-codon together with the neomycin resistance gene cassette is removed by the reconstituted Cre recombinase. Step 7: Expression of reporter (e.g. DsRed) is activated, and cells become sensitive to Neomycin again.

Figure 14:
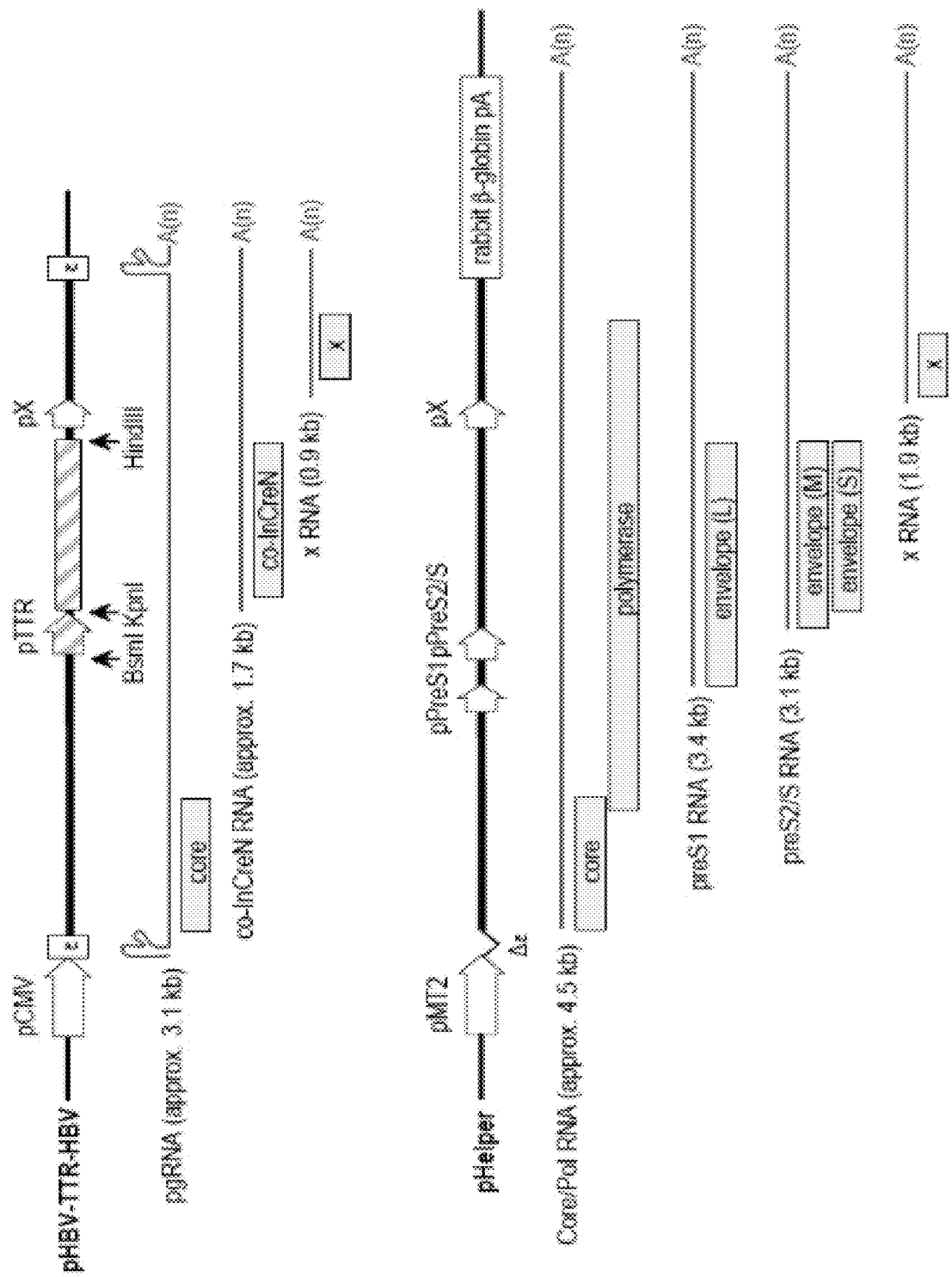

FIG. 14 shows the plasmid design for rHBV-CreN production. The rHBV-CreN transfer plasmid (pHBV-TTR-CreN) was generated by replacing the PreS/S-region of a 1.1-fold HBV genome (Nassal et al., 1990, Cell 63, 1357-1363) by a TTR promoter/enhancer (Diagonal stripes block arrow) and a Co-InCreN coding sequence (Diagonal stripes box). Thus, pHBV-TTR-CreN uses the original HBV polyA site to expresses (i) a HBV pgRNA carrying Co-InCreN sequence, which translated into HBV core protein and packed into newly forming capsid; and (ii) subgenomic RNAs expressing Co-InCreN as well as HBx. The HBV helper plasmid (pHelper) encodes all viral proteins (core, polymerase, L, M and S envelope proteins, and HBx) but is encapsidation deficient because the 5' epsilon (ε) sequence of HBV has been removed. To prevent reconstitution of a wildtype HBV genome by recombination between the two plasmids, we substituted the HBV polyA signal with that of rabbit □-globin. Block arrows indicate promoters or enhancers. Grey lines indicate transcripts. Grey boxes indicate open reading frames.

Figure 15:
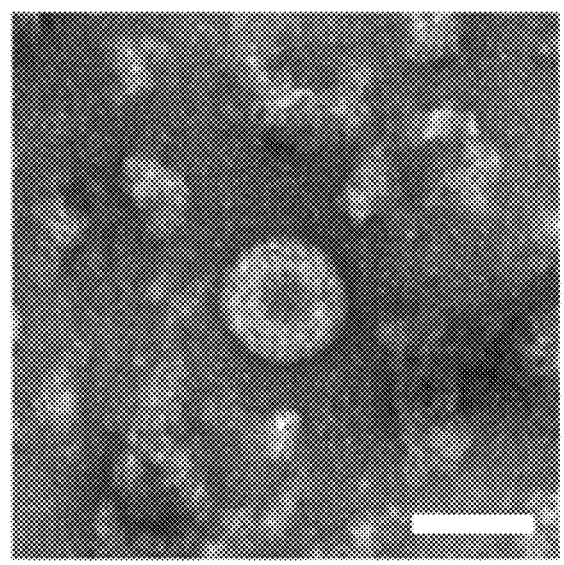

FIG. 15 shows electron microscopy of the purified virus particles. rHBV-CreN was purified by heparin affinity chromatography and subsequent sucrose density gradient centrifugation, fixed and examined by transmission electron microscopy using negative staining. Scale bar represents 50 nm.

Figure 16:
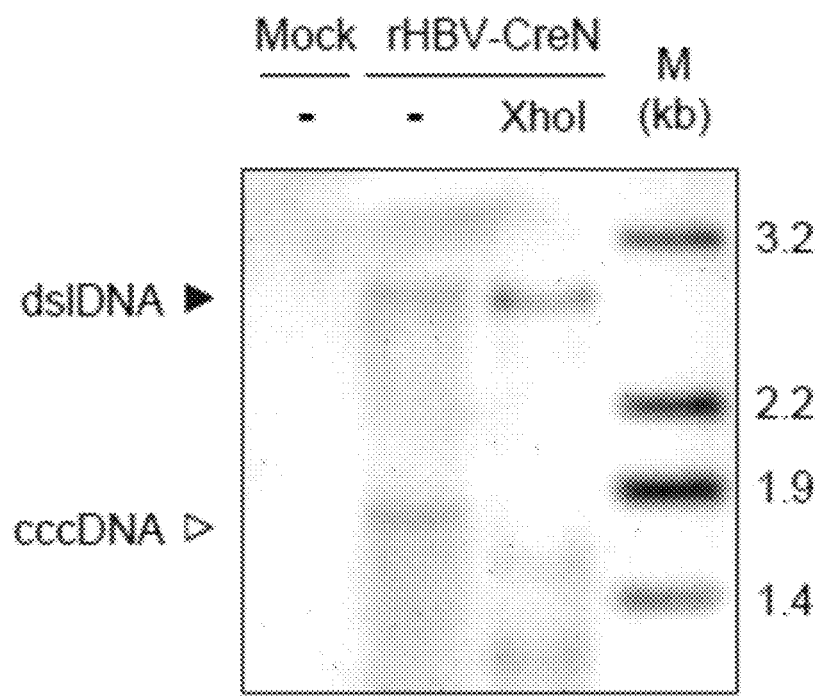

FIG. 16 shows a Southern Blot of HepG2-NTCP-CreC/CIR cells that were infected overnight with heparin-column purified rHBV-CreN (MOI=1000 virions/cell) in 4% PEG8000 containing medium. Mock samples were cultivated identical without addition of rHBV. Cells were harvested 4 days post infection. Protein-free DNA was isolated after Hirt extraction and analyzed by Southern blot with and without XhoI digestion. Open triangle indicates cccDNA. Filled triangle indicates dslDNA.

Figure 17:
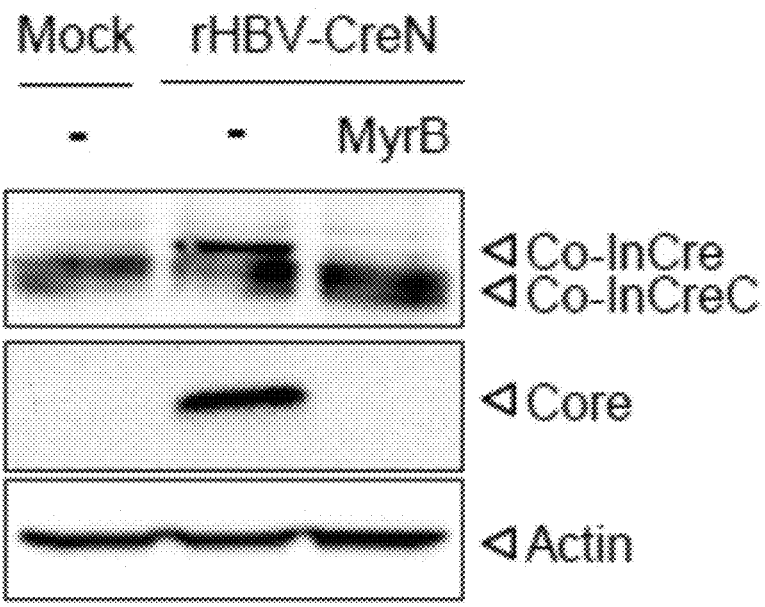

FIG. 17 shows a western blot in which the Co-InCre reconstitution was analyzed.

Figure 18:
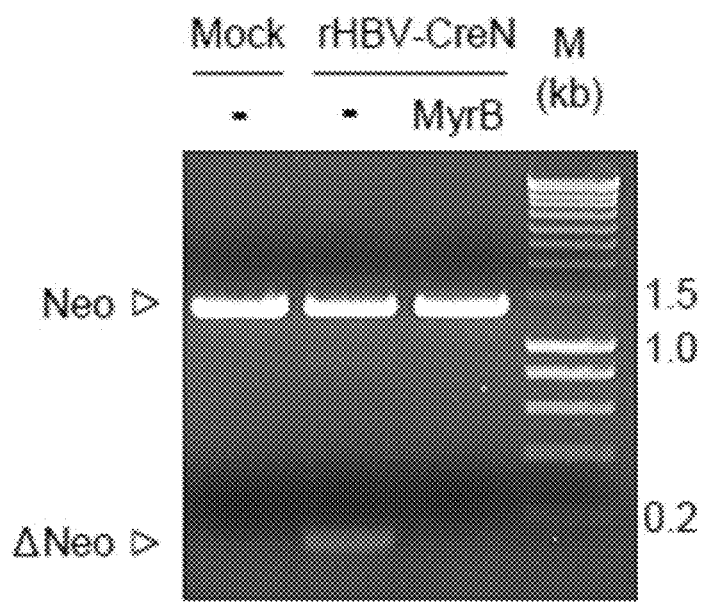

FIG. 18 shows total DNA isolated from rHBV-CreN infected HepG2-NTCP-CreC/CIR cells that were analyzed by PCR using primers flanking the loxp-Neo-Stop-loxp cassette. PCR products were subjected to agarose gel electrophoresis. Neo indicates the PCR product containing the neomycin sequence and the stop codon. ΔNeo indicates the shorter PCR product lacking the neomycin sequences.

Figure 19:
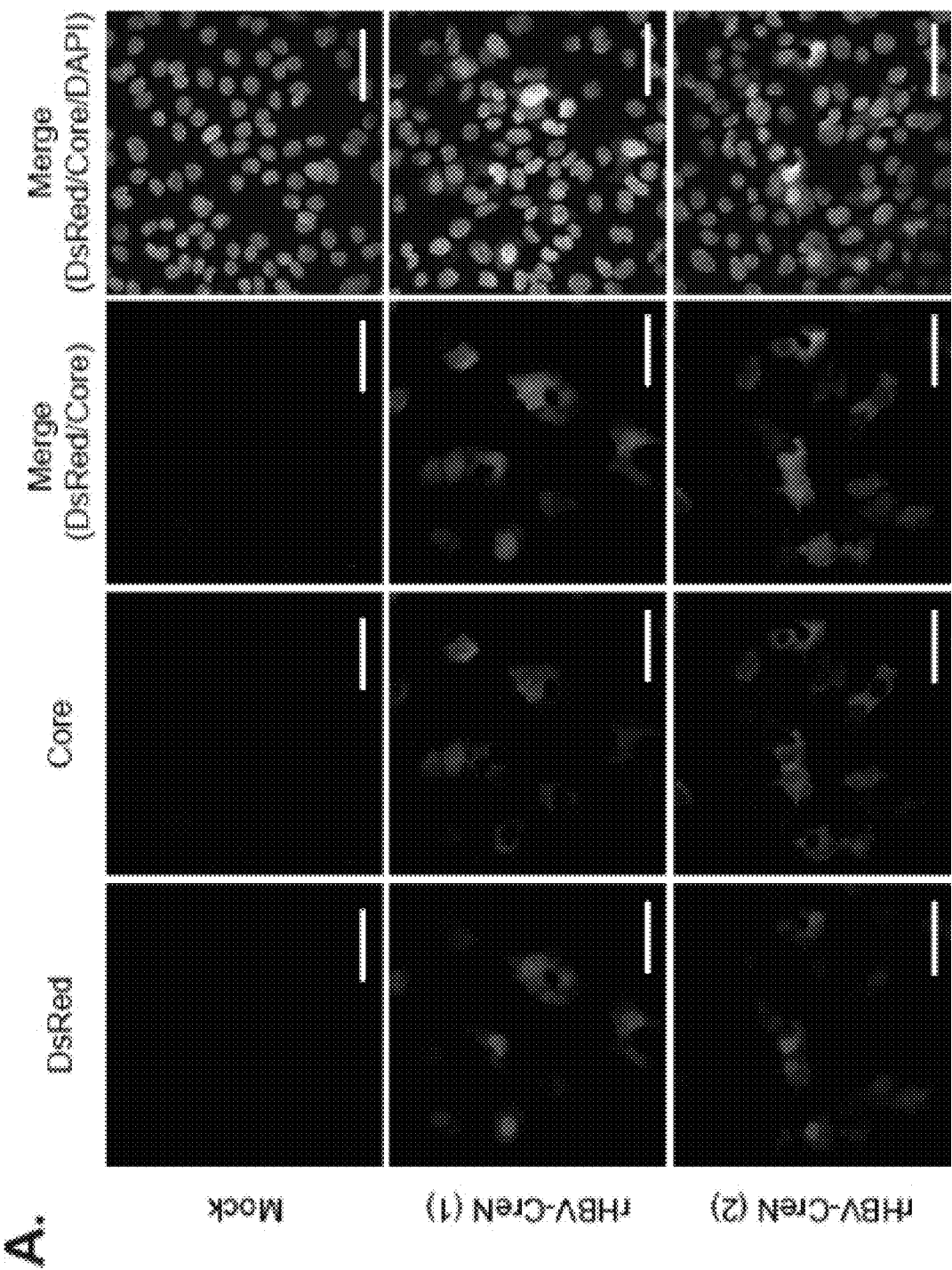
Figure 19:
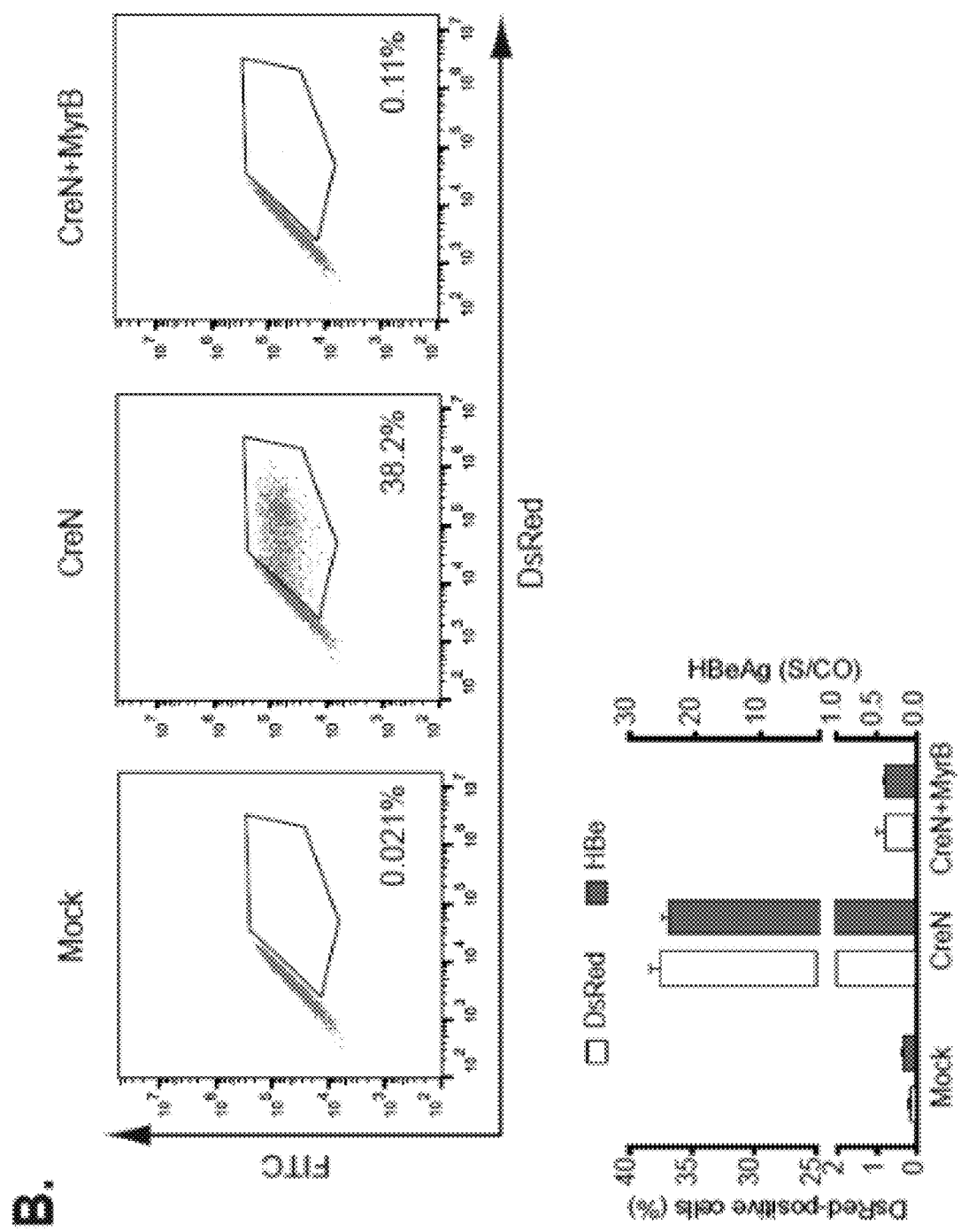
Figure 19:
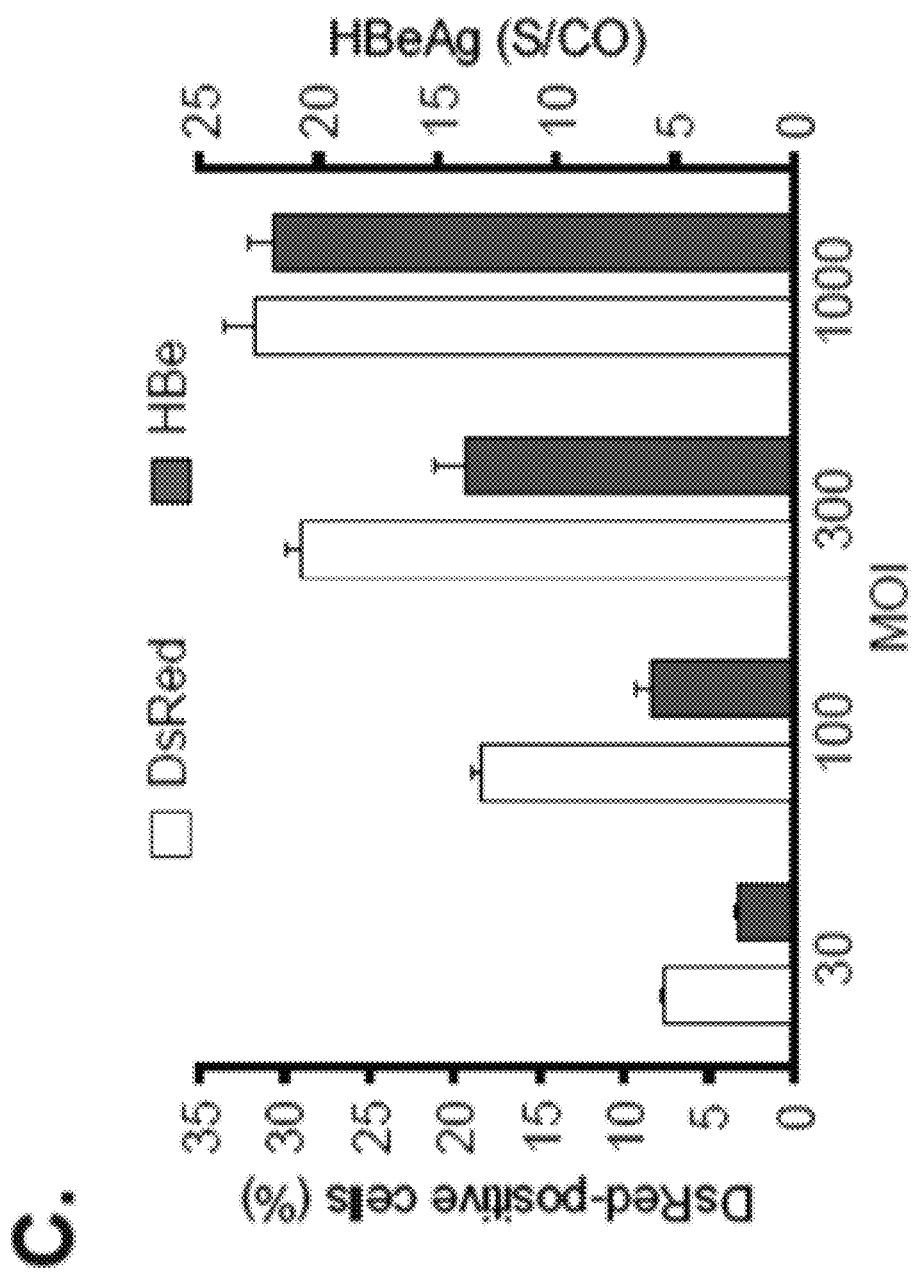
Figure 19:
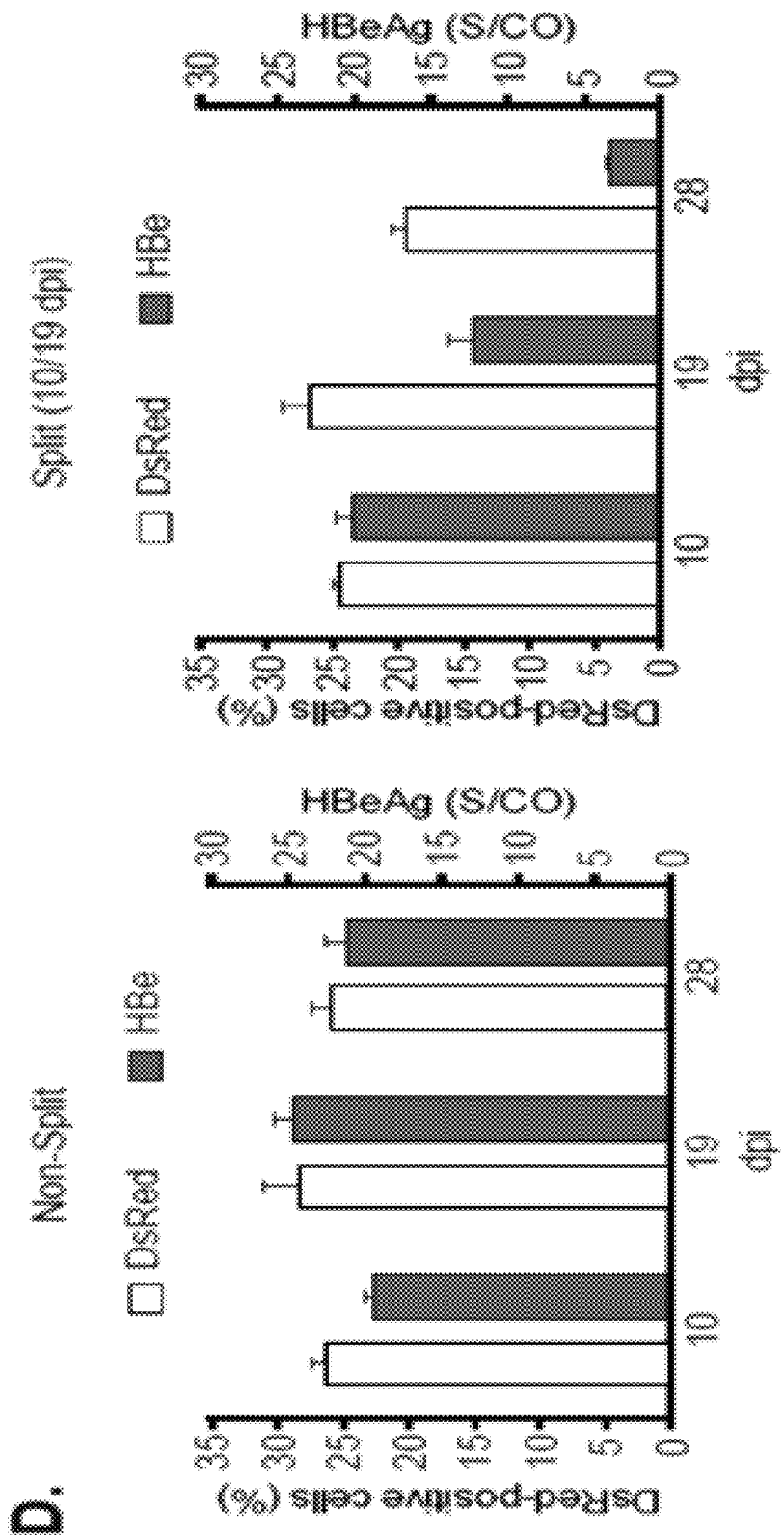
Figure 19:
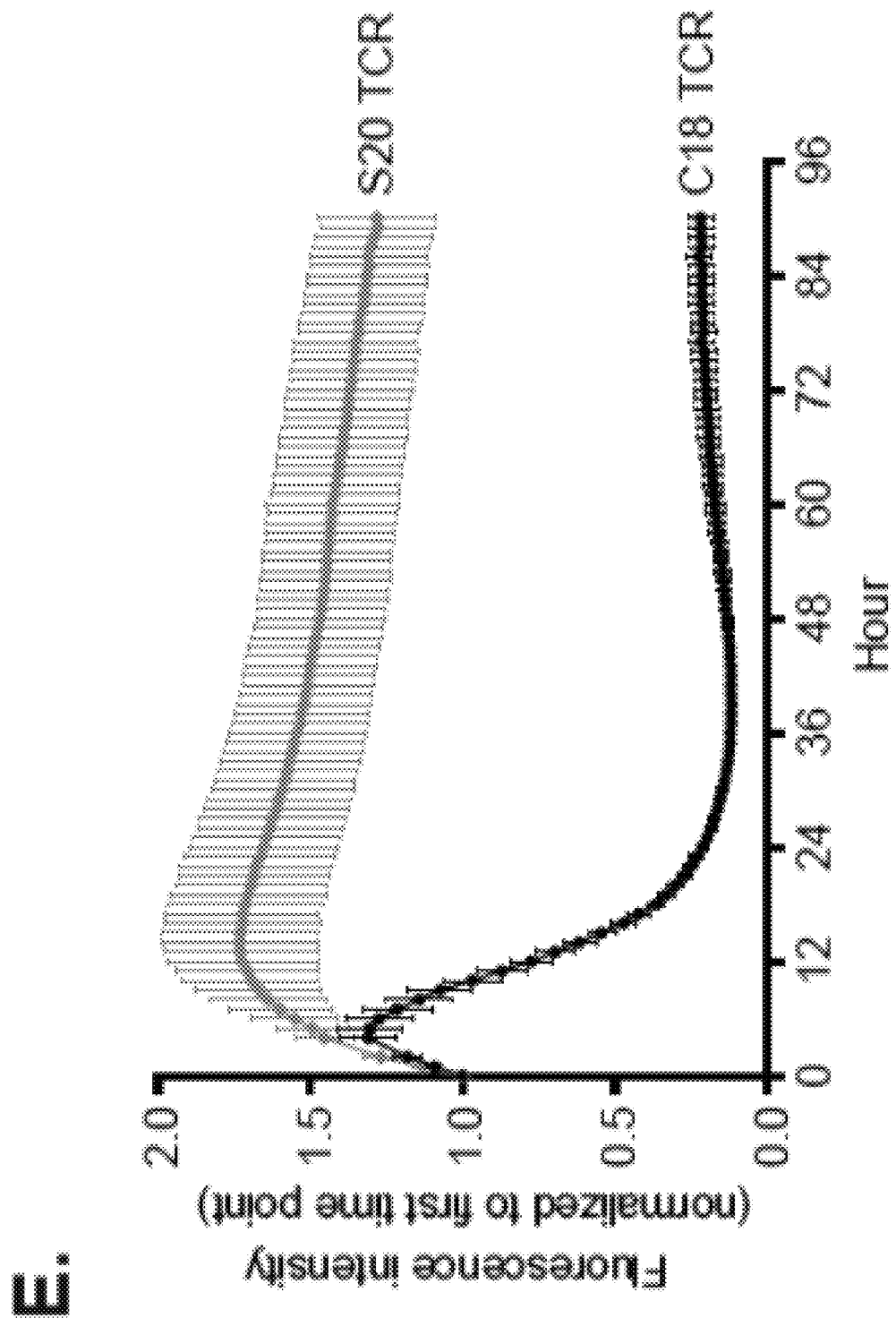
Figure 19:
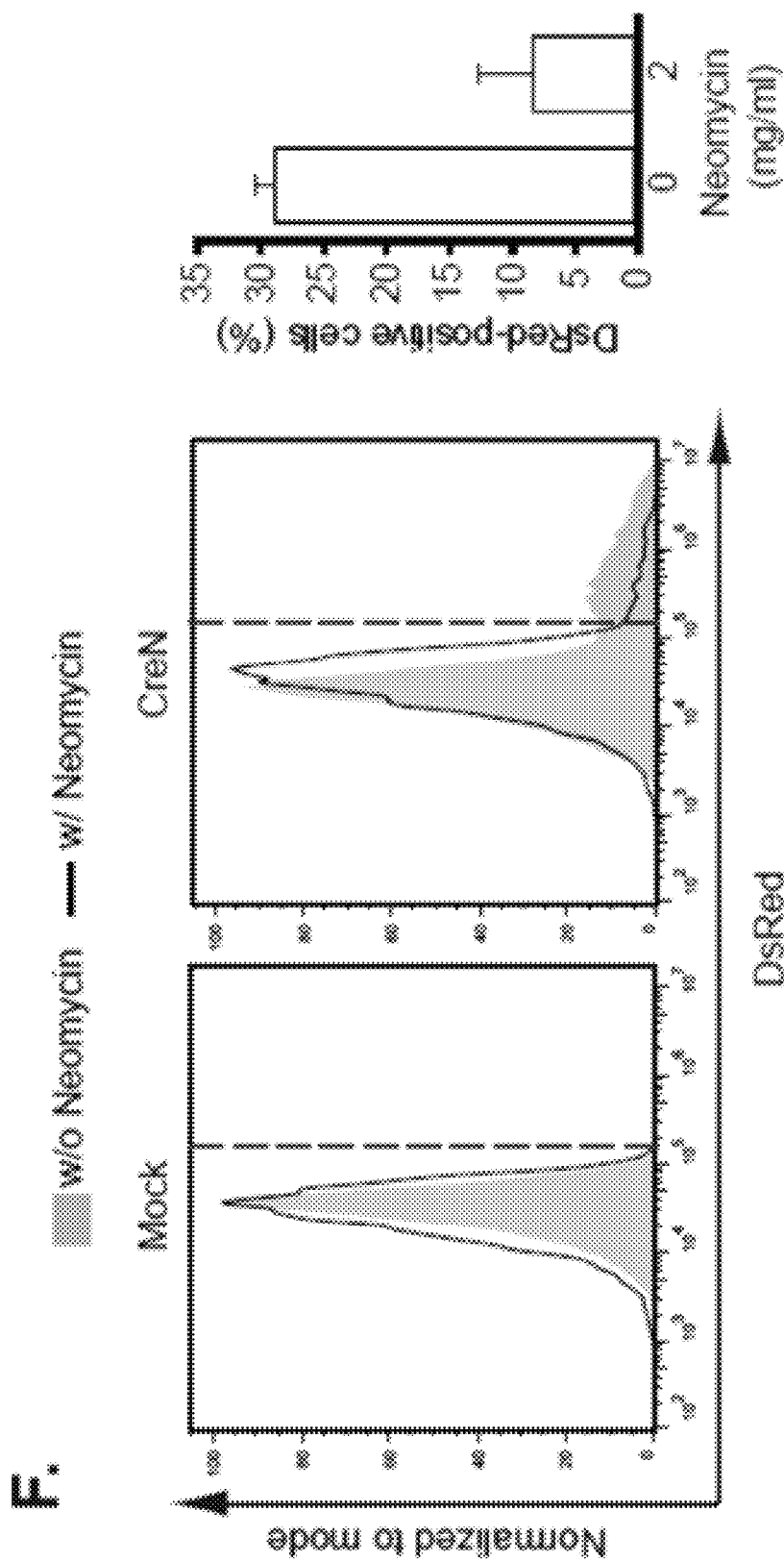

FIG. 19 shows an exemplary application of the rHBV-CreN reporter system (A) HepG2-NTCP-CreC/CIR cells were infected with rHBV-CreN (MOI=300 virions/cell). After 9 days of culture, cells were fixed, permeabilized, and stained for HBV core protein and DNA to indicated cell nuclei (DAPI). The DsRed (red), core (green), and DAPI (blue) signals were analyzed by fluorescence confocal microscopy with a 60× objective. Scale bars represent 50 µm. (B) HepG2-NTCP-CreC/CIR cells were infected with rHBV-CreN (MOI=300 virions/cell) with or without HBV entry inhibition (Myrcludex B, 200 µM). Cells were collected on 10 days post infection from triplicate samples. The percentage of DsRed-positive cells was determined by flow cytometry after setting a gate (indicated on each plot) on the basis of the fluorescence intensity of the mock samples. Flow cytometry results are presented as values of mean±SD together with HBeAg determined by ELISA. HBeAg is reported as sample to cut-off ratio (S/CO), and samples with a ratio greater than one were considered positive. (C) HepG2-NTCP-CreC/CIR cells were infected with rHBV-CreN using different MOIs (30, 100, 300, and 1000 virions/cell) in triplicate. Cells were collected on day 10 post infection and analyzed according to (B). (D) HepG2-NTCP-CreC/CIR cells were infected with rHBV-CreN (MOI=300 virions/cell). One set of the infected cells was collected on 10, 19, and 28 days post infection (Non-Split). The other set was split at a dilution ratio of ½ on day 10 and 19 (Split d10/d19) and collected in parallel. Triplicate samples were analyzed according to (B). All results are presented as values of means±SD. (E) HBV core- (black line) or S-specific T cells (grey line) were co-cultured with rHBV-CreN infected cells at an effector:target ratio of 1:1 on day 10 post infection. In quadruplet samples of each treatment, DsRed fluorescence intensity was monitored for 90 hours using an IncuCyte® S3 Live-Cell Analysis System. The average fluorescence intensity of five images per sample was acquired. The fold changes of the integrated fluorescence intensity relative to the starting point of the co-culture is given as means±SD. (F) The infected cells were cultured with an indicated concentration of Neomycin (0 or 2 mg/ml) for 30 days. The percentage of DsRed-positive cells was determined by flow cytometry in triplicate samples. Grey-shaded histograms indicate the cells without Neomycin treatment, black lines indicate the cells after Neomycin treatment. Areas to the right of the dashed line indicate DsRed-positive populations. The flow cytometry results of the infected cells are presented as values of mean±SD.

DETAILED DESCRIPTION

The present invention is described in detail in the following and will also be further illustrated by the appended examples and figures.

Current studies or drug screenings are done with wild-type HBV. However, this procedure is costly and labor-intensive. More advanced approaches in prior art aimed at integrating a reporter gene into a recombinant HBV. By using a fluorescent reporter gene, infected cells can be counted by, e.g., a flow cytometer. However, the successfully infected cells will only transiently express the reporter genes for about 2 weeks until the cccDNA is lost due to the cell division. HBV dslDNA rarely integrates into the host genome and the HBV cccDNA (converted from HBV rcDNA) will not duplicate while the host cells are dividing. Cell proliferation often results in loss of cccDNA. The reporter gene carried by a recombinant reporter HBV is transcribed from the cccDNA structure. Its expression relies on the number and the stability of the cccDNA. In other words, the expression of the reporter gene will cease when the infected cells start to divide. Bai et al. 2016, Viruses, 8:125, provide an overview of different strategies to transport a "cargo" into a host cell. However, none of these approaches solve the problem of a permanent overexpression of a reporter gene.

Figure 1:
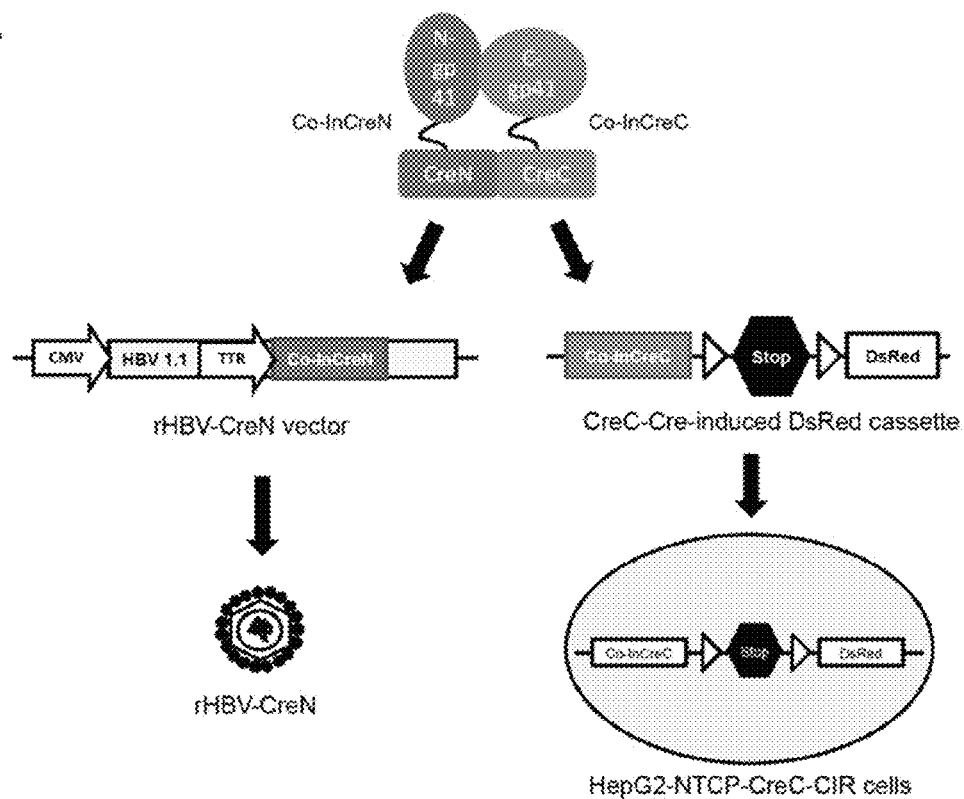
FIG. 1 shows the Co-InCre system and the rHBV-CreN vector as exemplary and not-limiting embodiment of two fragments of a recombinase that form an active recombinase.
Figure 1:
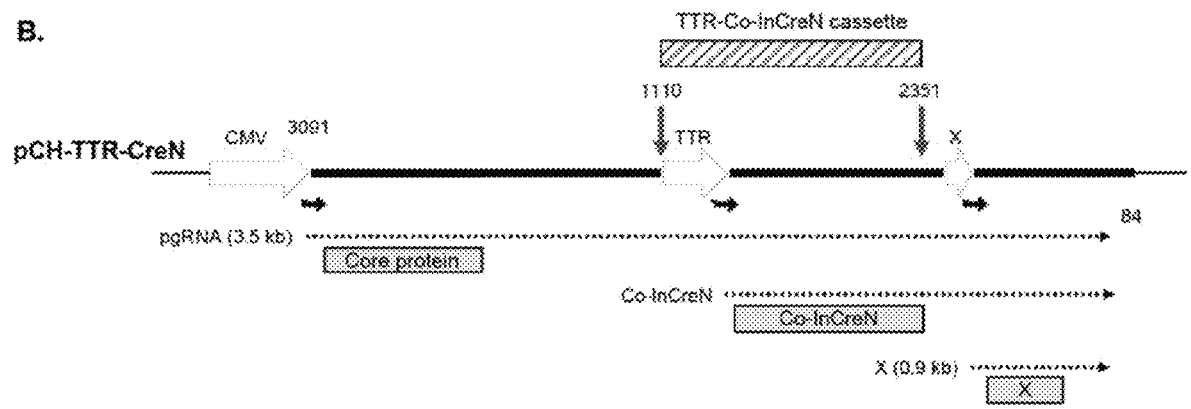

The inventors surprisingly found that a "split" recombinase system such as the Co-InCre system described in Hermann et al. 2014, Nucleic Acids Research, 42(6):3804-3907 is functional within the context of a hepadnaviral infection. In the exemplary embodiment outlined in the Examples section, see also FIG. 1 or FIG. 13, the Cre recombinase is split into two fragments. The first fragment of the Cre recombinase is integrated into the genome of an HBV (reporter virus) and will expressed in a host cell after infection (see Example 1). The second fragment of the Cre recombinase is integrated into a HepG2 cell (reporter cell), which overexpresses NTCP to be susceptible for an infection with HBV. This HepG2 cell overexpresses the second fragment of Cre recombinase (see Example 2). After infection with the recombinant HBV (reporter virus), the first fragment of the Cre recombinase encoded by the viral genome is expressed as well. Both fragments associate and form an active recombinase. The HepG2 cell (reporter cell) further comprises in its genome a DsRed gene (reporter gene). However, the expression of DsRed is blocked by a transcriptional stop cassette. This stop cassette is flanked by two loxP sites and is removed by the Cre recombinase, enabling a permanent expression of DsRed. HepG2 cells, which have been successfully infected, can be analyzed by fluorimetric methods such as fluorescence microscopy or flow cytometry (see Example 3). Example 3 further provides evidence that the method of the invention is useful in assessing the capacity of a substance to treat or prevent hepadnavirus infection as shown by the reduction of fluorescence when the reporter virus is administered to the reporter cell after myrcludex B treatment, which inhibits viral entry of HBV. Example 4 and 5 provide further applications of the method of the invention.

Accordingly, the present invention relates to a method of assessing the capacity of a substance to treat or prevent hepadnavirus infection comprising: (a) Contacting a reporter cell with a reporter virus; and (b) Contacting the reporter cell with the substance, wherein the reporter virus comprises a nucleic acid encoding a first fragment of a recombinase; wherein the reporter cell comprises a nucleic acid encoding a second fragment of the recombinase; wherein the first fragment of the recombinase and the second fragment of the recombinase are capable of forming a functional recombinase; wherein the reporter cell comprises a nucleic acid comprising a stop cassette flanked by two recombination sites fused to a reporter gene, wherein the presence of the stop cassette suppresses expression of the reporter gene. The method may comprise detecting the presence or absence of a gene product of the reporter gene.

In general, the method of the invention can be carried out by first contacting the reporter cell with the substance and second contacting the reporter cell with the reporter virus or by first contacting the reporter cell with the reporter virus and then adding the substance to the reporter cell. However, also other sequences of the steps are envisioned. Accordingly, in one embodiment, the reporter cell is contacted with the substance before the reporter cell is contacted with the reporter virus. In another embodiment, the reporter cell is first contacted with the reporter virus and then contacted with the substance.

The method of the invention may further comprise a step of assessing the capacity of a substance to treat or prevent hepadnavirus infection. This step may include the analysis of reporter gene expression or a gene expression product by the reporter cell, e.g. by comparing the reporter gene expression or a gene expression product of untreated or mock-treated reporter cells with cells that have been contacted with the substance. An increased reporter gene expression or a gene expression product indicates a higher infection rate, i.e. that the substance might not have the capacity to treat or prevent hepadnavirus infection. Vice versa, a decreased reporter gene expression or a gene expression product indicates a lower infection rate, i.e. that the substance might have the capacity to treat or prevent hepadnavirus infection.

"Treatment" or "treating" of a hepadnavirus infection encompasses an alleviation of at least one symptom of the disease, a reduction in the severity of the disease, or the delay or prevention of disease progression to more serious symptoms that may, in some cases, accompany the disease or lead to at least one other disease. Treatment need not mean that the disease is totally cured. A useful therapeutic agent needs only to reduce the severity of a disease, reduce the severity of one or more symptoms associated with the disease or its treatment, or delay the onset of more serious symptoms or a more serious disease that can occur with some frequency following the treated condition.

"Prevention" or "preventing" of a hepadnavirus infection encompasses measures such as the administration of a substance taken for disease prevention, as opposed to disease treatment. Thus, prevention does not aim at treating an hepadnavirus infection but rather to reduce the infection rate to 50% or less, 40% or less, 30% or less, 20% or less, 10% or less, 5% or less or 1% or less, e.g. when a substance is given to prevent a hepadnavirus infection.

Examples for "substances" that can be tested include proteins, peptides and small molecules but also cells. The method of the present invention is most suitable for analysis of viral infections. Accordingly, the substance preferably prevents and/or inhibits the infection of the reporter cell. Such a substance is also useful in the treatment of a hepadnavirus infection because subsequent new infection of further cells of the host is prevented.

The substance can e.g. be an "antibody molecule". An "antibody molecule" as used herein can be a full length antibody, a recombinant antibody molecule, or a fully human antibody molecule. A full length antibody is any naturally occurring antibody. The term "antibody" also includes immunoglobulins (Ig's) of different classes (i.e. IgA, IgG, IgM, IgD and IgE) and subclasses (such as IgG1, IgG2 etc.). Such full length antibodies can be isolated from different animals such as e.g. different mammalian species. A "recombinant antibody molecule" refers to an antibody molecule the genes of which has been cloned, and that is produced recombinantly in a host cell or organism, using well-known methodologies of genetic engineering. Typically, a recombinant antibody molecule has been genetically altered to comprise an amino acid sequence, which is not found in nature. Thus, a recombinant antibody molecule can be a chimeric antibody molecule or a humanized antibody molecule. Preferably, the antibody prevents the attachment of the hepadnavirus to a molecule that is needed for viral entry, such as NTCP for HBV.

The substance can also be an "antibody fragment". Such antibody fragments comprise at least those parts of an antibody, that form the (antigen) binding site. Illustrative examples of such an antibody fragment are single chain variable fragments (scFv), Fv fragments, single domain antibodies, such as e.g. VHH (camelid) antibodies, di-scFvs, fragment antigen binding regions (Fab), F(ab')$_2$ fragments, Fab' fragments, diabodies, domain antibodies, (Holt L J, Herring C, Jespers L S, Woolven B P, Tomlinson IM. Domain antibodies: proteins for therapy. *Trends Biotechnol.* 2003 November; 21(11):484-90), or bispecific "Fabsc"-antibody molecules as described in International patent application WO 2013/092001 comprising a single chain Fv fragment which is connected to an Fab fragment via a CH2 domain to name only a few. Preferably, the antibody fragment prevents the attachment of the hepadnavirus to a molecule that is needed for viral entry, such as NTCP for HBV.

The substance can also be a proteinaceous binding molecule with antibody-like binding properties. Illustrative examples of proteinaceous binding molecules with antibody-like binding properties that can be used as binding proteins include, but are not limited to, an aptamer, a mutein based on a polypeptide of the lipocalin family (exemplary lipocalin muteins that are also known under their trademark name "Anticalin®" are, for example, described in PCT applications WO 99/16873, WO 00/75308, WO 03/029471, WO 03/029462, WO 03/029463, WO 2005/019254, WO 2005/019255, WO 2005/019256, WO 2006/56464 or WO 2008/015239, or the review article of Skerra, A. (2001) *Rev. Mol. Biotechnol.* 74, 257-275), a glubody, a protein based on the ankyrin scaffold, a protein based on the crystalline scaffold, an adnectin, an avimer, a EGF-like domain, a Kringle-domain, a fibronectin type I domain, a fibronectin type II domain, a fibronectin type III domain, a PAN domain, a G1a domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain (complement control protein (CCP) modules), a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill CR1, Gonzales J N, Houtz E K, Ludwig J R, Melcher E D, Hale J E, Pourmand R, Keivens V M, Myers L, Beidler K, Stuart P, Cheng S, Radhakrishnan R. Design and construction of a hybrid immunoglobulin domain with properties of both heavy and light chain variable regions. Protein Eng. 1997 August; 10(8):949-57) "Minibodies" (Martin F1, Toniatti C, Salvati A L, Venturini S, Ciliberto G, Cortese R, Sollazzo M. The affinity-selection of a minibody polypeptide inhibitor of human interleukin-6. EMBO J. 1994 Nov. 15; 13(22):5303-9), "Janusins" (Traunecker A, Lanzavecchia A, Karjalainen K. Bispecific single chain molecules (Janusins) target cytotoxic lymphocytes on HIV infected cells. EMBO J. 1991 December; 10(12):3655-9 and Traunecker A, Lanzavecchia A, Karjalainen K. Janusin: new molecular design for bispecific reagents. Int J Cancer Suppl. 1992; 7:51-2), a nanobody, an adnectin, a tetranectin, a microbody, an affilin, an affibody or an ankyrin, a crystallin, a knottin, ubiquitin, a zinc-finger protein, an autofluorescent protein, an ankyrin or ankyrin repeat protein or a leucine-rich repeat protein, an avimer (Silverman J1, Liu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P. Multivalent avimer proteins evolved by exon shuffling of a family of human receptor domains. Nat Biotechnol. 2005 December; 23(12):1556-61. Epub 2005 Nov. 20); as well as multivalent avimer proteins evolved by exon shuffling of a family of human receptor domains as also described in Silverman et al. (Silverman J, Liu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P. Multivalent avimer proteins evolved by exon shuffling of a family of human receptor domains. *Nat Biotechnol.* 2005 December; 23(12):1556-61. Epub 2005 Nov. 20). Preferably, the proteinaceous binding molecule prevents the attachment of the hepadnavirus to a molecule that is needed for viral entry, such as NTCP for HBV.

Further, the substance can also make use of RNA interference. RNA interference (RNAi) is a biological process in which RNA molecules inhibit gene expression or translation, by neutralizing targeted mRNA molecules. Two types of small ribonucleic acid (RNA) molecules—microRNA (miRNA) and small interfering RNA (siRNA)—are central to RNA interference. The RNAi pathway is found in many eukaryotes, including animals, and is initiated by the enzyme Dicer, which cleaves long double-stranded RNA (dsRNA) molecules into short double-stranded fragments of ~21 nucleotide siRNAs. Each siRNA is unwound into two single-stranded RNAs (ssRNAs), the passenger strand and the guide strand. The passenger strand is degraded and the guide strand is incorporated into the RNA-induced silencing complex (RISC). The well-studied outcome is post-transcriptional gene silencing, which occurs when the guide strand pairs with a complementary sequence in a messenger RNA molecule and induces cleavage by Argonaute 2 (Ago2), the catalytic component of the RISC. In some organisms, this process spreads systemically, despite the initially limited molar concentrations of siRNA. Accordingly, the substance can be a miRNA or a siRNA. For example, such an RNA interfering molecule could inhibit the expression of a molecule that is needed for viral entry, such as NTCP for HBV infections.

The substance may also be or comprise a small molecule. Examples include nucleosides or derivatives thereof, nucleotides or derivatives thereof. Further, the substance could be an immune-modulatory or immune-stimulating substance such as an interferon or a derivative thereof.

The substance may also be a cell, such as an immune cell, such as a cytotoxic cell. Such a cell may mediate the killing of infected cells. Thus, the substance may be a cell that mediates the killing of a cell infected with HBV. Exemplary cells include a T cell, a CAR-T cell, an NK cell, or a CAR-NK cell, which may have the capacity to mediate the killing of a HBV-infected cell. Exemplary T cells and uses thereof are disclosed in Krebs et al. 2013, Gastroenterology, 145:456-465 or Wisskirchen et al. 2017, PLoS ONE, 12(8): e0182936. Alternatively, the substance may be an antibody that targets a cytotoxic cell, such as a T cell or NK cell to a (reporter) cell that has been infected with HBV and thereby initiates cell-mediated killing of the infected cell. Such an antibody may have a modified Fc region with increased interaction with Fc receptors, which may result in an increased antibody-dependent cell-mediated cytotoxicity (ADCC). Such an antibody may be a bispecific antibody, which may be specific for an HBV antigen and an (activating) T cell or NK cell receptor. Exemplary bispecific antibodies have been shown in US 2018/0079798 and US 2016/0200798.

The substances may have different modes of actions. Exemplary modes of actions that a substance may have include inhibitors of viral processes and/or inhibitors of processes of the host cell or the animal, which are essential for viral replication. Inhibition of viral processes may relate to inhibitors of viral entry, inhibitors of viral replication, inhibitors of virus assembly and/or inhibitors of viral release/budding. HBV relies on NTCP for viral entry. E.g., a substance that prevents binding to NTCP is an inhibitor of viral entry. Preferably, the substance prevents viral entry. The substance may also target a cell such as a cytotoxic T cell to a cell infected with the virus.

The reporter virus induces the expression the first fragment of the recombinase in the reporter cell, which expresses the second fragment of the recombinase. The method of the invention is particularly suited for studying hepadnavirus. Accordingly, the reporter virus is preferably a hepadnavirus or is a member of the hepadnaviridae. Hepadnaviridae are a family of related viruses. Humans, monkeys, and birds may serve as natural hosts. There are currently seven species in this family, divided among 2 genera. Its best-known member is the (human) Hepatitis B virus. Diseases associated with this family include: liver infections, such as hepatitis, hepatocellular carcinomas (chronic infections), and (liver) cirrhosis. The hepadnavirus may be a member of the avihepadnaviridae. The hepadnavirus may be an orthohepadnavirus. Preferably, the hepadnavirus is selected from the group consisting of (human) Hepatitis B virus, ground squirrel hepatitis virus, long-fingered bat hepatitis B virus, Pomona bat hepatitis B virus, round leaf bat hepatitis B virus, tent-making bat hepatitis B virus, woodchuck hepatitis virus, woolly monkey hepatitis B virus. Preferably, the hepadnavirus is (human) hepatitis B virus. The reporter virus preferably is derived from the hepadnavirus for which a substance to treat or prevent hepadnavirus is searched. Accordingly, the reporter virus may be a hepatitis B virus.

Hepadnaviruses have very small genomes of partially double-stranded (pds), partially single stranded circular DNA. The genome consists of two strands, a longer negative-sense strand and a shorter and positive-sense strand of variable length. In the virion these strands are arranged such that the two ends of the long strand meet but are not covalently bonded together. The shorter strand overlaps this divide and is connected to the longer strand on either side of the split through a direct repeat (DR) segment that pairs the two strands together. In replication, this pds genome is converted in the host cell nucleus to covalently-closed-circular DNA (cccDNA) by the viral polymerase. As it is a group 7 virus, replication involves an RNA intermediate. Four main open reading frames are encoded (ORFs) and the virus has four known genes which encode seven proteins: the core capsid protein, the viral polymerase, surface antigens—preS1, preS2, and S, the X protein and HBeAg. The X protein is thought to be non-structural. Its function and significance are poorly understood but it is suspected to be associated with host gene expression modulation. Hepadnaviridae encode their own polymerase, rather than co-opting host machinery as some other viruses do. This enzyme is unique among viral polymerases in that it has reverse transcriptase activity to convert RNA into DNA to replicate the genome (the only other human-pathogenic virus family encoding a polymerase with this capability is Retroviridae), RNAse activity (used when the DNA genome is synthesized from pgRNA that was packaged in virions for replication to destroy the RNA template and produce the pdsDNA genome), and DNA-dependent-DNA-polymerase activity (used to create cccDNA from pdsDNA in the first step of the replication cycle). The hepatitis envelope proteins are composed of subunits made from the viral preS1, preS2, and S genes. The L (for "large") envelope protein contains all three subunits. The M (for "medium") protein contains only preS2 and S. The S (for "small") protein contains only S. The genome portions encoding these envelope protein subunits share both the same frame and the same stop codon (generating nested transcripts on a single open reading frame. The pre-S1 is encoded first (closest to the 5' end), followed directly by the pre-S2 and the S. When a transcript is made from the beginning of the pre-S1 region, all three genes are included in the transcript and the L protein is produced. When the transcript starts after the pro-S1 at the beginning of the pre-S2 the final protein contains the pre-S2 and S subunits only and therefore is an M protein. The smallest envelope protein containing just the S subunit is made most because it is encoded closest to the 3' end and comes from the shortest transcript. These envelope proteins can assemble independently of the viral capsid and genome into non-infectious virus-like particles that give the virus a pleomorphic appearance and promote a strong immune response in hosts.

The reporter virus comprises a nucleic acid encoding the first fragment of the recombinase. Because of the limited size of the HBV genome, it might be necessary to replace a part of the viral genome by the cargo, i.e. the first fragment of the recombinase. Within the context of the method of the invention, it is not necessary that the reporter virus is replication competent, however it must be able to infect the reporter cell and the first fragment of the recombinase must be translated in the reporter cell. Thus, the preS/S may be replaced by the first fragment of the recombinase. FIG. 12 shows the organization of the HBV genome of the wt and the recombinant HBV. Here, the preS/S region has been replaced by a first fragment of the recombinase such as a CreN fragment under the control of a TTR promoter/enhancer. Further, the genome may not comprise a gene encoding for hepatitis B virus X protein, HBV envelope protein or HBV polymerase.

As the reporter virus might not be replication competent, it may be necessary to produce the reporter virus in connection with a helper plasmid, which encodes the proteins that are needed for the formation of the hepadnavirus virion (see also Example 1). As a minimum requirement the epsilon sequence can be seen, which targets the viral genome into the capsid. Thus, the genome of the reporter virus preferably comprises an epsilon sequence. However, the reporter virus preferably is capable of infecting the cell.

The reporter virus preferably comprises a genome comprising a gene encoding a HBV core protein or a hepatitis virus core protein. In one embodiment, the gene encoding a HBV core protein or a HBV core protein is operatively linked to a promoter. Preferably, the HBV core protein is under the control of a cytomegalovirus promoter.

In this context, the present invention also relates to a hepadnavirus comprising a nucleic acid encoding a first fragment of a recombinase. Thus, hepadnavirus and reporter virus may be used synonymously and all explanations herein, which relate to the reporter virus, may also apply to the hepadnavirus of the invention.

A reporter cell is the second component needed for assessing the capacity of a substance to treat or prevent hepadnavirus infection. While the reporter virus provides the first fragment of a recombinase, the reporter cell provides the second fragment of the recombinase. The reporter cell further comprises a reporter gene. The expression of the reporter gene is prevented by a stop cassette. This stop cassette is flanked by two recombination sites. When both, the first and the second fragment of the recombinase, the recombinase may excise the stop cassette located between the two recombination sites and therefore permanently enable the expression of the reporter gene. This process is only possible, when the reporter cell has been successfully infected by the reporter virus.

The reporter cell may be any cell that can be infected by the reporter virus and enable the expression of the first fragment of the recombinase after infection by the reporter virus. The reporter cell preferably is an animal cell, more preferably a mammalian cell. Examples of mammals include, but are not limited to, a mouse, a rat, a cow, a goat, a sheep, a pig, a dog, a cat, a horse, a guinea pig, a canine, a hamster, a mink, a seal, a whale, a camel, a chimpanzee, a rhesus monkey, a cynomolgus monkey, and a human, with a human being preferred. In one embodiment, the reporter cell may be a bird. Examples of suitable birds include, but are not limited to, a turkey, a chicken, a goose, a duck, a teal, a mallard, a starling, a Northern pintail, a gull, a swan, Guinea fowl or water fowl to name a few. In one embodiment, the reporter cell is a human cell. For the method of the invention, it is necessary that the reporter cell can be infected by the reporter virus. In some embodiments, HBV needs sodium taurocholate cotransporting polypeptide (NTCP) to enter a target or host cell. Thus, the reporter cell preferably comprises NTCP on the cell surface.

Many hepadnaviridae infect the liver, preferably hepatocytes. Thus, the reporter cell preferably is a hepatocyte. However, the invention is not limited to hepatocytes, if the reporter cell is susceptible to an infection with the reporter virus. In one embodiment, the reporter cell is a hepatoma cell.

The present invention also relates to a mammalian hepatocyte or hepatoma cell comprising a nucleic acid encoding a second fragment of a recombinase and a nucleic acid comprising a stop cassette flanked by two recombination sites fused to a reporter gene, wherein the presence of the stop cassette suppresses expression of the reporter gene. The term "a mammalian hepatocyte or hepatoma cell comprising a nucleic acid encoding a second fragment of a recombinase and a nucleic acid comprising a stop cassette flanked by two recombination sites fused to a reporter gene, wherein the presence of the stop cassette suppresses expression of the reporter gene" is used interchangeably with "reporter cell" herein, thus all explanations herein that relate to the reporter cell may also apply to the mammalian hepatocyte or hepatoma cell.

As outlined herein, the reporter virus provides a first fragment and the reporter cell a second fragment of a recombinase. The recombinase may be any enzyme that is capable of specifically recognizing recombination sites and performing a recombination by excising the stop cassette that is flanked by two recombination sites. A recombinase may also be described as (DNA) transposase, which use a limited repertoire of structurally and mechanistically distinct nuclease domains to catalyze the DNA strand breaking and rejoining reactions that comprise DNA transposition. The recombinase may be any of the 4 known types: (1) RNase H-like transposases (also known as DD(E/D) enzymes); (2) HUH single-stranded DNA transposases; (3) serine transposases; and (4) tyrosine transposases. Accordingly, the recombinase may be selected from the group consisting of Tpase, Tn5, MuA, Mos1, Hermes, HIV integrase, PFV integrase, Piv, TnpA, Helitrons, CTnDOT, Tn916, Flp, Cre, XerC/D, IS607, TnpX, Bxb1, ΦC31 integrase, Hin, Sin and γδ resolvase. The recombinase may also be a Sleeping beauty recombinase, a resurrected vertebrate transposase of the Tc1/mariner family. These recombinases are reviewed in Hickman and Dyda, 2015, Microbiol Spectrum 3(2): MDNA3-0034-2014, which is incorporated herein by reference. Preferably, the recombinase is a Cre recombinase. The recombinase preferably is capable of effecting recombination at the two recombination sites flanking the stop cassette. The recombination at the two recombination sites preferably results in excision of the stop cassette. The recombinase preferably has an amino acid sequence as set forth in SEQ ID NO: 1. Further Cre recombinases are disclosed in van Duyne 2015, Microbiol Spectrum, 3(1)MDNA3-0014-2014, which is incorporated by reference. The first fragment and the second fragment of a recombinase preferably are capable of forming a functional recombinase. A "functional recombinase" is a recombinase that exerts its activity of recombination. Within the context of the invention, a functional recombinase may be formed by two polypeptides. Here, the functional recombinase is formed by two fragments of the recombinase that form a dimer that is a functional recombinase.

As outlined herein, the reporter virus comprises the first fragment of a recombinase. In case, the recombinase is a Cre recombinase, the reporter virus preferably comprises genome comprising a gene encoding an N-terminal fragment of Cre recombinase. A preferred sequence for the N-terminal fragment is depicted in SEQ ID NO: 2, which corresponds to positions 19 to 59 of the wild type Cre recombinase. SEQ ID NO: 21 shows a preferred nucleic acid sequence of the N-terminal fragment of Cre recombinase. Preferably, the N-terminal fragment of Cre recombinase is under the control of a transthyretin promoter as shown in SEQ ID NO: 3. Preferably, the first fragment of the recombinase further comprises a nuclear localization signal (NLS), e.g. an SV40 NLS as shown in SEQ ID NO: 4. Additionally, the first fragment of a recombinase such as the CreN fragment of the Cre recombinase outlined herein, may be further fused to an N-terminal fragment of another protein, such as the N-terminal fragment of gp41 DNA helicase (N-gp41), e.g. as depicted in SEQ ID NO: 5. An exemplary vector that encodes a viral genome that can be incorporated into virions using a helper plasmid is shown in SEQ ID NO: 6. FIG. 12 shows an exemplary embodiment of the reporter virus genome ("rHBV-CreN vector").

For illustrative purposes, the production of a recombinant HBV (rHBV) is described in the following (see also Untergasser and Protzer 2004, Human Gene Therapy, 15:203-210, incorporated herein by reference): For the production of rHBV, human hepatoma cells (HuH7) may be used. HuH7 cells can be maintained in Dulbecco's modified Eagle's medium (DMEM) containing 50 mg streptomycin per milliliter, 50 IU penicillin per milliliter, 1 mM sodium pyruvate, nonessential amino acids, 2 mM L-glutamine, and 10% heat-inactivated fetal calf in 5% $CO_2$. Cells may be co-transfected at 30-40% confluence with 25 mg each of the respective transfer and helper constructs (exemplary constructs are shown in FIG. 14) per 150-mm dish using the calcium-phosphate method as described recently (Protzer et al. 1999, PNAS, 96:10818-10823, incorporated herein by reference). Alternatively, may be co-transfected with 3 mg each of the indicated transfer and helper constructs per 150-mm dish using 18 ml of Fugene 6 (Roche Molecular Biochemicals, Mannheim, Germany) according to the manufacturer's instructions. Cell culture medium containing recombinant virions can be collected from days 3-5 post transfection and cleaned from cell debris by centrifugation at 1250 g for 10 min. rHBV should be concentrated 50-fold by precipitation with 6.5% polyethylene glycol 6000 at 0° C. and stored in phosphate-buffered saline (PBS)/10% glycerol at −80° C. until further use as described (Protzer et al., 1999, supra).

An alternative exemplary method for the production of a recombinant HBV (rHBV) is the following procedure: Huh7 cells may be seeded on 9 cm dishes (6010 $mm^2$) and incubated until approx. 80% confluence is reached. Transfection may then be conducted by mixing 16 μg of DNA together with 0.8 ml of Opti-MEM™ (Gibco), and 48 μl of FuGene HD. After 15 minutes of incubation, the transfection mixture may be added to the cells, which should be changed to 9 ml of DMEM transfection medium (DMEM, high glucose, 2 mM Glutamine, 1 mM sodium pyruvate, 0.1 mM non-essential amino acids). The transfected cells may be first changed to the rHBV production medium I (0.5×DMEM, high glucose, 0.5× William's E medium, 5 FCS, 0.025% Glucose, 10 mM HEPES, pH 7.4, 2 mM Glutamine, 50,000 U Penicillin-Streptomycin, 3% DMSO, 20 mg of Gentamicin, 1.3 mg of hydrocortisone, and 6.4 IE of Insulin, 0.5 mM sodium pyruvate, 0.05 mM non-essential amino acids) the day after transfection. After 24 hours of incubation, cells may then be changed to the rHBV production medium II (William's E medium, 5 FCS, 0.05% Glucose, 20 mM HEPES, pH 7.4, 2 mM Glutamine, 50,000 U Penicillin-Streptomycin, 2% DMSO, 40 mg of Gentamicin, 2.6 mg of hydrocortisone, and 12.8 IE of Insulin). Thereafter, supernatant may be collected every 4 days in a total of 6 times. Cell debris may be removed from the supernatant by centrifugation at 1,500 g for 15 min. The virus-containing solution could be stored at 4° C. until the six collections are completed. All collections of virus-containing supernatant may then be pooled together and filtrated with a Stericup® filter unit to remove the cell debris and aggregates. Heparin affinity chromatography may be set up by placing the peristaltic tube on the peristaltic pump, and then the heparin column may be connected to the tube. The column may be first washed with the elution buffer (3.2 mM $KH_2PO_4$, 466 mM NaCl, and 8.9 mM $Na_2HPO_4$) and then equilibrated with the binding buffer (0.8 mM $KH_2PO_4$, 116.4 mM NaCl, and 2.2 mM $Na_2HPO_4$). The virus solution may then be loaded onto a heparin column with a speed of 5 ml per minute, and then the column may be washed with 5 column volumes of the binding buffer. The column may be removed from the peristaltic system and 6 ml of rDNase solution (20 mM Tris, pH7.5, 10 mM $MgCl_2$, 5 mM $CaCl_2$, and 200 U rDNase) may be applied to the column with syringe. The column may be incubated at room temperature for 1 hour, and then may be washed with 5 column volumes of the binding buffer. Virus may be eluted with 4 column volumes of the elution buffer with a speed of 2 ml/minute. Ultrafiltration tubes may then be used to dilute the salt out and reduce the total volume of the virus stock. The virus stock can be stored at −80° C.

The present invention also relates to an rHBV-CreN virus-producing cell line. This cell line is directed to produce the HBV comprising the gene for CreN at a high titer. To generate such a cell line, the Co InCreN cassette may be cloned into a piggyback-based rHBV vector. This plasmid will then be transfected together with a plasmid expressing transposase into the helper cell line (HepG2-LMS-Poly-X). By puromycin selection, successfully modified clones can be selected. After expansion in 12-well plates, the clones will be evaluated and the clone showing the highest production rate of rHBV-CreN will be selected.

As outlined herein, the reporter cell comprises the second plasmid of a recombinase. In case, the recombinase is a Cre recombinase, the reporter cell preferably comprises a nucleic acid encoding a C-terminal fragment of Cre recombinase. A preferred sequence for the CreC is depicted in SEQ ID NO: 7, which corresponds to sequence positions 60 to 299 of wild type Cre. SEQ ID NO: 22 shows a preferred nucleic acid sequence of the C-terminal fragment of the Cre recombinase. Preferably, the first fragment of the recombinase further comprises a nuclear localization signal, e.g. as shown in SEQ ID NO: 4. Additionally, the second fragment of a recombinase such as the CreC fragment of the Cre recombinase described herein, may be further fused to a C-terminal fragment of another protein, such as the C-terminal fragment of gp41 DNA helicase (C-gp41), e.g. as depicted in SEQ ID NO: 8. An exemplary vector that can be used as plasmid to generate a reporter cell is shown in SEQ ID NO: 9. FIG. 15 shows an exemplary embodiment of the second plasmid of a recombinase.

In an alternative embodiment, the reporter virus comprises a nucleic acid encoding for CreC and the reporter cell comprises a nucleic acid encoding CreN.

The recombinase requires recombination sites for its functions. The recombination sites define the position at which the site-specific recombination takes place. The Cre recombinase recognizes loxP sequences. The Hin recombinase recognizes a hixL and a hixR sequence (see e.g. Glasgow et al. 1989, JBC, 264(17):10072-10082). The Flp recombinase (also known as flippase) binds to FRT sequences and recombines them. Preferred loxP sequences are shown in SEQ ID NOs: 10 to 19. Particularly preferred loxP sequence is SEQ ID NO: 10. For the Cre recombinase, the orientation of the loxP sequence is determining for the action of the Cre recombinase. If the two loxP recombination sites are in the same orientation, the DNA between the two loxP sites is excised. This can be used to remove the stop cassette that prevents the expression of the reporter gene. Accordingly, the recombination sites are preferably in the same orientation. Two identical recombination sites may increase the efficiency of the recombinase. Accordingly, the two recombination sites preferably are identical.

The reporter gene may be any detectable gene product regardless whether it is directly or indirectly detected. Preferably, the reporter gene is a detectable gene product. Examples include, but are not limited to, optically detectable gene products such as fluorescent proteins or enzymes that catalyze a color reaction. E.g., the fluorescent protein may be GFP, eGFP, YFP, RFP, mCherry, dsRed and the like. Also enzymes that catalyze a color reaction are well known to a person skilled in the art and can be applied in spectrophotometric assays. The reporter gene may also be an enzyme that catalyzes a bioluminescent reaction such as a luciferase. The method of the invention may further comprise detecting the presence or absence of a gene product of the reporter gene. In one embodiment, the detection of the reporter gene is performed using flow cytometry, e.g. when DsRed is detected by flow cytometry in a reporter cell that has been successfully infected with the reporter virus. The reporter gene may also encode a protein that is detectable on the cell surface. This protein may be detected by flow cytometry or magnetic beads (e.g. in a MACS®-based assay). In one embodiment, the reporter gene is a gene that provides resistance to an antibiotic such as G418 (geneticin), neomycin, blasticidin, bleomycin, zeocin (phleomycin) or hygromycin. The presence or absence of a gene product of the reporter gene may be indicative whether a substance has a capacity to treat or prevent hepadnavirus infections. E.g., a substance that prevents a successful infection of the reporter cell by the reporter virus, there will be no or at least less of the gene product of the reporter gene detectable. Thus, the method may comprise assessing the capacity of the substance to treat or prevent hepadnavirus infection based on the presence or absence of a gene product of the reporter gene.

A stop cassette prevents the expression of the reporter gene or the gene product of a reporter gene. Within the context of the invention, the stop cassette may be excised by a functional recombinase. The stop cassette may be a transcriptional or translational stop cassette. A transcriptional stop cassette prevents transcription of the respective gene while a translational stop cassette prevents the translation of a mRNA into a protein. Preferably, the stop cassette is a SV40 PolyA Terminator such as the sequence as set forth in SEQ ID NO: 20. The combination of a stop cassette flanked by two loxP sites is also known as Lox-Stop-Lox and many other examples are known to a person skilled in the art.

The present invention further relates to a system comprising the hepadnavirus and/or reporter virus of the invention and the mammalian hepatocyte or hepatoma cell of the invention and/or the reporter cell of the invention.

The invention further relates to the use of the virus of the invention, the mammalian hepatocyte or hepatoma cell of the invention, the reporter cell of the invention or the system of the invention for assessing the capacity of a substance to treat or prevent hepadnavirus infection.

The present invention also relates to the following items:

1. A method of assessing the capacity of a substance to treat or prevent hepadnavirus infection comprising:
(a) Contacting a reporter cell with a reporter virus; and
(b) Contacting the reporter cell with the substance
wherein the reporter virus comprises a nucleic acid encoding a first fragment of a recombinase;
wherein the reporter cell comprises a nucleic acid encoding a second fragment of the recombinase;
wherein the first fragment of the recombinase and the second fragment of the recombinase are capable of forming a functional recombinase;
wherein the reporter cell comprises a nucleic acid comprising a stop cassette flanked by two recombination sites fused to a reporter gene, wherein the presence of the stop cassette suppresses expression of the reporter gene.

2. The method of item 1, wherein the hepadnavirus is a hepatitis B virus.

3. The method of item 1 or 2, wherein the reporter virus is a hepatitis B virus.

4. The method of any one of the preceding items, wherein the reporter virus comprises a genome comprising a gene encoding a hepatitis B virus core protein.

5. The method of item 4, wherein the gene encoding a hepatitis B virus core protein is under the control of a cytomegalovirus promoter.

6. The method of any one of the preceding items, wherein the reporter virus comprises a genome comprising a gene encoding an N-terminal fragment of Cre recombinase.

7. The method of item 6, wherein the gene encoding an N-terminal fragment of Cre recombinase is and the control of a transthyretin promoter.

8. The method of any one of the preceding items, wherein the reporter virus comprises a genome not comprising a gene encoding for hepatitis B virus X protein, hepatitis B virus envelope protein or hepatitis B virus polymerase.

9. The method of any one of the preceding items, wherein the reporter virus is capable of infecting the reporter cell.

10. The method of any one of the preceding items, wherein the reporter cell is an animal cell.

11. The method of any one of the preceding items, wherein the reporter cell is a mammalian cell.

12. The method of any one of the preceding items, wherein the reporter cell comprises a sodium taurocholate cotransporting polypeptide (NTCP).

13. The method of any one of the preceding items, wherein the reporter cell is a hepatocyte.

14. The method of any one of the preceding items, wherein the reporter cell is a hepatoma cell.

15. The method of any one of the preceding items, wherein the recombinase is capable of effecting recombination at the two recombination sites flanking the stop cassette.

16. The method of any one of the preceding items, wherein recombination at the two recombination sites results in excision of the stop cassette.

17. The method of any one of the preceding items, wherein the recombinase is Cre recombinase.

18. The method of any one of the preceding items, wherein the recombinase has an amino acid sequence set forth in SEQ ID NO: 1.

19. The method of any one of the preceding items, wherein the first fragment of the recombinase or the second fragment of the recombinase or both the first and the second fragment of the recombinase has no recombinase activity in absence of another fragment of the recombinase.

20. The method of any one of the preceding items, wherein the first fragment of the recombinase is CreN.

21. The method of any one of the preceding items, wherein the first fragment of the recombinase has an amino acid sequence set forth in SEQ ID NO: 2.

22. The method of any one of the preceding items, wherein the second fragment of the recombinase is CreC.

23. The method of any one of the preceding items, wherein the second fragment of the recombinase has an amino acid sequence set forth in SEQ ID NO: 7.

24. The method of any one of the preceding items, wherein the recombination site is a loxP site.

25. The method of any one of the preceding items, wherein the recombination site has a sequence set forth in SEQ ID NOs: 10-19.

26. The method of any one of the preceding items, wherein the recombination sites are in the same orientation.

27. The method of any one of the preceding items, wherein the stop cassette is a transcriptional or translational stop cassette.

28. The method of any one of the preceding items, wherein the stop cassette has a sequence set forth in SEQ ID NO: 20.

29. The method of any one of the preceding items, wherein the reporter gene encodes a detectable gene product.

30. The method of any one of the preceding items, wherein the reporter gene encodes an optically detectable gene product.

31. The method of any one of the preceding items, wherein the reporter gene encodes a fluorescent protein.

32. The method of any one of the preceding items, wherein the method comprises detecting the presence or absence of a gene product of the reporter gene.

33. The method of any one of the preceding items, wherein detection is performed using flow cytometry.

34. The method of any one of the preceding items, wherein the method comprises assessing the capacity of the substance to treat or prevent hepadnavirus infection based on the presence or absence of a gene product of the reporter gene.

35. The method of any one of the preceding items, wherein the method comprises providing information about the capacity of the substance to treat or prevent hepadnavirus infection.

36. A hepadnavirus comprising a nucleic acid encoding a first fragment of a recombinase.

37. The hepadnavirus of item 36, wherein the hepadnavirus is a hepatitis B virus.

38. The hepadnavirus of item 36 or 37, wherein the recombinase is Cre recombinase.

39. The hepadnavirus of any one items 36 to 38, wherein the first fragment of the recombinase is CreN.

40. The hepadnavirus of any one items 36 to 39, wherein the hepadnavirus comprises a genome comprising a gene encoding a hepatitis B virus core protein.

41. The hepadnavirus of any one items 36 to 40, wherein the gene encoding a hepatitis B virus core protein is under the control of a cytomegalovirus promoter.

42. The hepadnavirus of any one items 36 to 41, wherein the hepadnavirus comprises a genome comprising a gene encoding an N-terminal fragment of Cre recombinase.

43. The hepadnavirus of any one items 36 to 42, wherein the gene encoding a hepatitis B virus core protein is under the control of a transthyretin promoter.

44. The hepadnavirus of any one items 36 to 43, wherein the hepadnavirus comprises a genome not comprising a gene encoding for hepatitis B virus X protein, hepatitis B virus envelope protein or hepatitis B virus polymerase.

45. A mammalian hepatocyte or hepatoma cell comprising a nucleic acid encoding a second fragment of a recombinase and a nucleic acid comprising a stop cassette flanked by two recombination sites fused to a reporter gene, wherein the presence of the stop cassette suppresses expression of the reporter gene.

46. The mammalian hepatocyte or hepatoma cell of item 45, wherein the second fragment of the recombinase is CreC.

47. The mammalian hepatocyte or hepatoma cell of item 45 or 46, wherein the recombination site is a loxP site.

48. The mammalian hepatocyte or hepatoma cell of any one of items 45 to 47, wherein the recombination sites are in the same orientation.

49. The mammalian hepatocyte or hepatoma cell of any one of items 45 to 48, wherein the stop cassette is a transcriptional or translational stop cassette.

50. The mammalian hepatocyte or hepatoma cell of any one of items 45 to 49, wherein the reporter gene encodes a detectable gene product.

51. The mammalian hepatocyte or hepatoma cell of any one of items 45 to 50, wherein the reporter gene encodes a fluorescent protein.

52. The mammalian hepatocyte or hepatoma cell of any one of items 45 to 51, wherein the cell has been infected by the hepadnavirus of any one of items 36 to 44.

53. The mammalian hepatocyte or hepatoma cell of item 52, wherein the stop cassette has been excised from the nucleic acid comprising the reporter gene.

54. A system comprising the hepadnavirus of any one of items 36 to 44 and a mammalian hepatocyte or hepatoma cell of any one of items 45 to 53.

55. Use of the virus of any one of items 36 to 44, the mammalian hepatocyte or hepatoma cell of any one of items 45 to 53, or the system of item 54 for assessing the capacity of a substance to treat or prevent hepadnavirus infection.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "more than" does not include the concrete number.

For example, less than 20 means less than the number indicated. Similarly, more than or greater than means more than or greater than the indicated number, e.g. more than 80% means more than or greater than the indicated number of 80%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

EXAMPLES

An even better understanding of the present invention and of its advantages will be evident from the following examples, offered for illustrative purposes only. The examples are not intended to limit the scope of the present invention in any way.

Materials and Methods

Unless stated otherwise, the following materials and methods were used in the examples of this disclosure.

Plasmid Constructs

Plasmids containing Co-InCreN or Co-InCreC sequences were a gift from Pawel Pelczar (Addgene plasmid #51267 and #51268). The rHBV transfer vector was constructed by replacing the PreS/S promoter of a 1.1-fold HBV genome (genome type D) with the mouse transthyretin (TTR) promoter (Nassal et al., 1990, Cell 63, 1357-1363; Untergasser and Protzer, 2004, Human gene therapy 15, 203-210). To clone Co-InCreN sequence into the rHBV transfer vector, KpnI and HindIII restriction sites were introduced to the 5' and 3' of Co-InCreN sequence by polymerase chain reaction (PCR) using Phusion® Hot Start Flex DNA Polymerase (New England Biolabs, M0535S). The PCR-amplified fragment was inserted into a blunt-end vector—pJET1.2 using CloneJET PCR Cloning Kit (Thermo Scientific, K1231), and subsequently cloned into the rHBV transfer vector (FIG. 2A). The Co-InCreC sequence together with the chimeric CMV early enhancer/chicken β actin (CAG) promoter was cloned into PvuI and SpeI restriction sites of a Cre reporter plasmid (pCALNL-dsRed; a gift from Connie Cepko, Addgene plasmid #13769). And the resulting plasmid was termed pCAG-CreC-CANLNL-dsRed.

Cell Lines and Cell Culture

HepG2-NTCP-CreC/CIR cells was generated by transfecting the plasmid pCAG-CreC-CALNL-dsRed into HepG2-NTCP-K7 cells. Subsequent selection of neomycin-resistant clones was done by culturing the cells in the presence of geneticin (2 mg/ml, Gibco, 10131-027). HepG2-NTCP-CreC/CIR cells and Huh7 cells (Nakabayashi et al., 1982, Cancer research 42, 3858-3863) were maintained in Dulbecco's Modified Eagle Medium (DMEM; Gibco, 11960-044) supplemented with 10% fetal bovine serum (FBS; Gibco, 10500-064), 50,000 U Penicillin-Streptomycin (Gibco, 15140-122), 2 mM L-glutamine (Gibco, 25030-024), 1 mM sodium pyruvate (Gibco, 11360-039), 0.1 mM non-essential amino acids (Gibco, #11140-035). HepAD38 cells (Ladner et al., 1997, Antimicrob Agents Chemother 41, 1715-1720) were maintained in Dulbecco's Modified Eagle Medium: Nutrient Mixture F-12 (DMEM/F-12; Gibco, 11320-074) supplemented with 10% fetal bovine serum (Gibco, 10500-064), 50,000 U Penicillin-Streptomycin (Gibco, 15140-122).

Recombinant HBV Production

The production procedure was modified based on the previous publication by Protzer and colleagues (Protzer et al., 1999, Proc Natl Acad Sci USA 96, 10818-10823). Huh7 cells grown to 70% confluency were co-transfected with pHBV-TTR-CreN and pHelper at a 1:1 ratio. The transfection was performed using 80 μg of the plasmids and 480 μl of FuGENE HD transfection reagent (Promega, E2311) per 150 cm$^2$ cell culture flask (TPP Techno Plastic Products AG). After transfection, cells were cultured in DMEM/

William's E medium (Gibco, 22551-022) supplemented with 5% FBS, 0.025% Glucose (Gibco, A24940-01), 10 mM Hepes (pH 7.4; Gibco, 15630-056), 2 mM Glutamine, 50,000 U Penicillin-Streptomycin, 3% Dimethyl sulfoxide (DMSO; Sigma, D2650), 20 mg of Gentamicin (Ratiopharm), 1.3 mg of hydrocortisone (Pfizer), and 6.4 IE of Insulin (Sanofi Aventis), 0.5 mM sodium pyruvate and 0.05 mM non-essential amino acids for 24 hours. Subsequently, cells were maintained in William's E medium, 5% FBS, 0.05% Glucose, 20 mM Hepes (pH 7.4), 2 mM Glutamine, 50,000 U Penicillin-Streptomycin, 2% DMSO, 40 mg of Gentamicin, 2.6 mg of hydrocortisone, and 12.8 IE of Insulin. Thereafter, the virus-containing supernatant was collected every 4 days in total 6 times. Cell debris were removed from the supernatant by centrifugation at 1500×g for 15 minutes and the supernatant was stored at 4° C. until six collections were completed.

The virus was concentrated by polyethylene glycol (PEG) precipitation (Protzer et al., 1999, Proc Natl Acad Sci USA 96, 10818-10823) and stored in THE buffer (10 mM Tris-HCl, pH 7.5, 150 mM NaCl, and 1 mM EDTA). Alternatively, the virus was purified by heparin affinity chromatography using a HiTrap Heparin HP column (GE Healthcare, 17-0407-03) (Burwitz et al., 2017, Nat Commun 8, 2146; Seitz et al., 2016, Cell host & microbe 20, 25-35). To eliminate plasmid bound to the virus, an on-column DNase digestion step was included into the heparin purification procedure. Following the washing of the heparin column, 6 ml of DNase solution (20 mM Tris, pH 7.5, 10 mM $MgCl_2$, 5 mM $CaCl_2$, 240 µl rDNase; MACHEREY-NAGEL, 740963) was applied to the column for one hour at room temperature. For long-term storage of the heparin-purified virus, FBS was added to the virus stock at a 1:1 ratio.

Southern Blot Analysis of Viral DNA

Viral DNA was isolated from virus stocks using QIAamp® MinElute® Virus Spin Kit (Qiagen, 57704). The isolation was performed according to the manufacturer's instructions and the DNA was eluted in a volume of 25 µl. XhoI digestion and 85° C. treatment of the DNA samples were used as controls to define the identity of HBV DNA. Since HBV genome contains one XhoI site, the digested rcDNA linearizes whereas the digested dslDNA results in two shorter DNA fragments. Double-stranded DNA, including rcDNA and dslDNA, denatured at 85° C. become single-stranded DNA (ssDNA). Subsequently, the DNA samples were resolved on a 1 agarose gel at 100 volts for two hours.

Southern blot capillary transfer was performed according to previously published procedure (Cai et al., 2013, Methods Mol Biol 1030, 151-161). The UV cross-linked membrane was pre-incubated with hybridization buffer (1% BSA, 1 mM EDTA, 500 mM Sodium phosphates, 0.7% SDS) at 65° C. for 2 hours. Digoxigenin (DIG)-labeled HBV-specific DNA probes were generated using PCR DIG Labeling Mix (Roche, 11585550910). HBV core-specific probe was obtained with primers 5'-TTCAGGCAACTCTTGTGG-3' (SEQ ID NO: 23) and 5'-TGAGGCGCTATGTGTTGT-3' (SEQ ID NO: 24). HBV x-specific probe was obtained with primers 5'-ATGGCTGCTAGGCTGTGCTG-3' (SEQ ID NO: 25) and 5'-TGGTGCGCAGACCAATTTAT-3' (SEQ ID NO: 26). The membrane was incubated with the hybridization buffer containing the probes at 65° C. overnight. Following the washing step, the membrane was developed using DIG Luminescent Detection Kit (Roche, 1363514). Chemiluminescent signals were detected by Intas ECL ChemoCam (INTAS Science Imaging).

The band intensity of rcDNA and dslDNA was quantified by ImageJ software (National Institutes of Health, USA). The virus titer was determined by comparing the band intensity of rHBV-CreN to that of a known wtHBV stock.

Southern Blot Analysis of cccDNA

Hirt extraction was used to isolate cccDNA (Yan et al., 2012, eLife 1, e00049.). Phenol/chloroform/isoamyl alcohol solution (25:24:1; Roth, A156.2) was applied to further purify DNA from the Hirt extract. The separation of DNA and proteins was performed twice by centrifuge at 3,500 g for 10 minutes at 4° C. followed by an additional phenol extraction. To precipitate the DNA, equal volume of isopropanol and 20 µg of glycogen (Ambion, AM9510) were added to the sample and incubated at −20° C. for 16 hours. The DNA precipitate was collected by centrifuge at 14,000 g for 30 minutes at 4° C., and the pellet was washed once with 700 µl of 70% ethanol. The DNA was dissolved in 20 µl of $ddH_2O$ and resolved on a 1.3% agarose gel at 20 volts for 16-20 hours. Southern blot analysis was performed as previously described. DIG-labeled HBV-specific DNA probe generated with primers 5'-TTCTAGA-TACCGCCTCAGCTCT-3' (SEQ ID NO: 27) and 5'-TGGTGCGCAGACCAATTTAT-3' (SEQ ID NO: 28) and spanned 3002 bp (genome type D) was used for the hybridization step.

Electron Microscopy

The Dane particles in the heparin-purified virus solution were further enriched by ultracentrifugation using a discontinuous sucrose density gradient (15, 25, and 60%) (Seitz et al., 2016, Cell host & microbe 20, 25-35). The viral particles were inactivated with 2% paraformaldehyde (PFA). The inactive viral sample was absorbed onto a copper grid with a formvar/carbon film (400 mesh; Science Services, EFCF400-Cu-50) and negatively stained with 2% uranyl acetate. Images were examined using a Libra 120 transmission electron microscope (Zeiss) with a magnification of 40,000.

Infection of rHBV

HepG2-NTCP-CreC/CIR cells were seeded on collagen-coated plates with a density of $1.34 \times 10^3$ cells/$mm^2$ and cultured in DMEM containing 2.5% dimethylsulfoxide (DMSO) for 2 days prior to infection. The inoculum was prepared by diluting the virus in DMEM containing 2.5% DMSO and 4% PEG8000. For blocking rHBV entry, Myrcludex B (200 nM) was added to the rHBV inoculum (Li and Urban, 2016, Cancer research 42, 3858-3863). The cells were inoculated for 24 hours and maintained in DMEM containing 2.5% DMSO for indicated time according to the experimental set-ups.

Western Blot Analysis

Cellular proteins were isolated using RIPA buffer (Pierce, 89900) containing a protease inhibitor cocktail (Roche, 11836153001). The proteins were separated by 12% Sodium dodecyl sulphate-polyacrylamide gel electrophoresis (SDS-PAGE) and subsequently transferred onto a polyvinylidene difluoride (PVDF) membrane (Bio-Rad, 162-0177). The blotted membrane was blocked with 5% milk-TBST (20 mM Tris-HCl, pH7.4, 140 mM NaCl, 1% Tween 20). The antibodies were diluted in 1.5% milk-TBST. For core protein detection, an in-house hybridoma supernatant (8C9) was used in a 1:1 dilution. For Co-InCre detection, an anti-Cre antibody (Merck, 69050) was used in a 1:1000 dilution. □-Actin (1:5000; Sigma, A5441) was used as a reference protein. The membranes were incubated in primary antibody overnight at 4° C. and subsequently incubated with the secondary antibody (anti-mouse or anti-rabbit, 1:10000; Sigma, A0168 and A0545) for two hours at room temperature. Membranes were developed using Amersham ECL Prime Western Blotting Detection Reagent (GE Healthcare). The chemiluminescent signal was detected by Intas ECL ChemoCam.

Detection of Cre-Lox Recombination by PCR

Genomic DNA of the cells was isolated using NucleoSpin® Tissue Kit (Macherey-Nagel, 740952.250). The Cre-lox recombination was analyzed by PCR using primers flanking the neomycin sequence (forward, 5'-CAACGTGCTGGTTATTGTGC-3' (SEQ ID NO: 29) and reverse, 5'-GGTACCGTCGACTGCAGAT-3' (SEQ ID NO: 30)). The PCR was performed with 250 ng of genomic DNA and Phusion® Hot Start Flex DNA Polymerase (New England Biolabs, M0535S). The reaction required the following conditions: 1 cycle of denaturation at 98° C. for 30 seconds, 35 cycles of amplification (98° C. for 10 seconds, 61° C. for 30 seconds, 72° C. for 45 seconds), and 1 cycle of extension at 72° C. for 1 minute. The PCR products were examined by agarose gel electrophoresis.

Confocal Microscopy

The staining of rHBV-CreN infected cells was performed according to previous report (Ko et al., 2018, J Hepatol.). Rabbit anti-core sera (1:400 dilution; Ad48, provided by Prof. Michael Nassal, University Hospital Freiburg) and secondary Alexa488-conjugated goat anti-rabbit IgG (1:1000; Invitrogen, A11070) were used for detecting core protein. The fluorescence images were obtained using Fluoview FV10i confocal laser-scanning microscope (Olympus).

Flow Cytometry Analysis

Cells were collected from 24-well plates using trypsin-versene at a 1:1 ratio (Gibco, 15400-054 and 15040-033). Cell pellets were resuspended in 1 ml of FACS buffer (PBS containing 1% BSA and 0.5 mM EDTA) and incubated with LIVE/DEAD™ Fixable Near-Infrared dead cell stain kit (Invitrogen, L10119). The samples were subjected to CytoFLEX S (Beckman Coulter) and the obtained data was analyzed by FlowJo software (v10, FlowJo LLC.).

HBeAg ELISA

The amount of HBeAg in cell-derived supernatants was measured using a commercial qualitative immunoassay—Enzygnost HBe monoclonal (Siemens, OQDM11) and automated BEP III system (Siemens Healthcare).

Live-Cell Imaging

HepG2-NTCP-CreC/CIR cells were seeded in a 96-well plate and subsequently infected with rHBV-CreN. On 10 days post infection, human T cells transduced with HBV core-specific (C18) or S-specific (S20) TCRs (Wisskirchen et al., 2017, PLoS One 12, e0182936) were applied to the cells at a 1:1 ratio. The DsRed-positive cells were monitored for 4 days using an IncuCyte® S3 Live Cell Analysis System (Essen BioScience). Phase contrast and red channel (Ex: 565/05 nm; Em: 625/05 nm) images were captured every hour using a 10× objective. The images were processed by the IncuCyte software using the Top-Hat background subtraction (radius=30 µm, threshold=0.4 RCU). The integrated fluorescence intensity of five separated areas per well were combined. The data were presented as the averaged integrated fluorescence intensity of four replicates normalized to that of start time point.

Example 1: Production of rHBV-creN (Reporter Virus)

Split-cre complementation system is a system that the activity of Cre recombinase is controlled by a ligand-induced complementation of the inactive Cre fragments. The Co-InCre system consists of two components, Co-InCreN and Co-InCreC. Co-InCreN is a fusion of the N-terminal iCre (aa 19-59) (SEQ ID NO: 2) and the N-terminal gp41-1 (SEQ ID NO: 5), whereas Co-InCreC is a fusion of the C-terminal gp41-1 (SEQ ID NO: 8) and the C-terminal iCre (aa 60-343) (SEQ ID NO: 7). The Cre reconstitution is achieved by the intein-mediated trans-splicing reaction of the gp41-1 fragments. Since the size of Co-InCreN (414 bp) is much smaller than that of Co-InCreC (990 bp), the Co-InCreN cassette was cloned into the rHBV vector and the Co-InCreC cassette was integrated into the genome of the host cells (FIG. 1A). Because the insert is shorter than the excised HBV fragment, the resulting genome size of rHBV-CreN (2.8 kb) is smaller than that of wtHBV (3.2 kb).

The production of rHBV-CreN was done in a trans-complement manner (Protzer et al. 1999, PNAS, 96:10818-10823). In contrast to the wtHBV production method in which all viral components required for infectious virus production are derived from a single DNA template, two plasmids are required for the recombinant HBV production (see also FIG. 14). The first plasmid, the rHBV vector (here, SEQ ID NO: 6), is designed to express rHBV pgRNA and core protein. The second plasmid, an HBV helper plasmid, provides the essential genes for virus assembling. The polymerase plasmid encodes the polymerase and the surface proteins, whereas the helper plasmid encodes core protein and x protein additionally. The rHBV vector and the HBV helper plasmid were co-transfected into Huh7 cells. The cells and the supernatant were harvested 7 days later. The viral capsids in the cells and the viral particles in the supernatant were concentrated by polyethylene glycol (PEG) precipitation. Following the DNA extraction from the pellets, the viral genome was analyzed by Southern blot. A positive control was prepared by using the cell lysate and supernatant of Huh7 cells transfected with a 1.1-fold wtHBV vector (pCH-9/3091).

First step was to analyze the expression of rHBV-CreN pgRNA derived from rHBV-CreN vector. RNA was isolated from Huh7 cells transfected with rHBV-CreN vector together with or without the helper plasmid and analyzed by Northern blot. Additionally, RNA isolated from HepAD38 cells, a stable cell line constantly producing wtHBV, was included as positive control. It is known that the 3.5 kb HBV pre-genomic RNA (pgRNA) and 2.4/2.1 kb HBV sub-genomic RNA (sgRNA) are expressed in HepAD38 cells. As shown on the blot, two bands were detected in the HepAD 38 sample. They were presumably corresponding to wtHBV pgRNA and wtHBV sgRNA (FIG. 2, Lane 3). Two bands were observed in the sample transfected with CreN plasmid alone (FIG. 2, Lane 1), which were migrated faster than that of the HepaAD38 sample. Since the genome size of rHBV-CreN is smaller compare to the wtHBV, the pgRNA and the sub-genomic RNA are excepted to be shorter. Moreover, the expression of rHBV-CreN pgRNA and sgRNA was independent to the helper plasmid. Three bands represented rHBV-CreN pgRNA, wtHBV sgRNA, and rHBV-CreN sgRNA were detected in the sample co-transfected with CreN plasmid and the helper plasmid (FIG. 2, Lane 2). rHBV-CreN pgRNA and sgRNA were derived from the rHBV vector, whereas the wtHBV sgRNA was derived from the helper plasmid. Compare to the CreN sample, the level of rHBV-CreN pgRNA is lower in the co-transfection sample. No signal of wtHBV pgRNA were detected in the co-transfection sample, this indicates the helper plasmid is not able to generate the wtHB V pgRNA.

Next, the expression of viral proteins derived from rHBV-CreN vector as well as the helper plasmid was analyzed by Western blot. Cell lysate of HepaAD38 cells was included as positive control. No viral proteins were detected in Huh7 cells (FIG. 3, Lane 1). HBc protein was the only viral protein detected in cells transfected with rHBV-CreN vector alone (FIG. 3, Lane 2). As expected, no surface proteins were detected, this is because the coding sequence of surface proteins was replaced by Co-InCreN cassette. Although the X promoter and its coding sequence is remained in the rHBV-Cre vector, no HBx protein was detected. In the cells co-transfected with rHBV-CreN vector and the helper plasmid, HBc protein, surface proteins, and HBx protein were detected (FIG. 3, Lane 3). However, compared to the wtHBV-producing cell line (HepAD38 cells, FIG. 3, Lane 4), the level of the surface proteins expressed from the helper plasmid was much lower.

Lastly, HBV DNA in the capsid as well as in the viral particles was analyzed. Cell lysate and supernatant of the transfected Huh7 cells and HepAD38 cells (positive control) were subjected to PEG precipitation. Preparation and analysis of the DNA samples was done by Southern Blot (FIG. 4). Three bands corresponding to rcDNA, dslDNA, ssDNA were detected in the capsids derived from HepAD38 cells (FIG. 4A, Lane 5). Two bands corresponding to rHBV-CreN rcDNA and dslDNA were detected in the capsids derived from Huh7 cells co-transfected with rHBV-CreN vector and the helper plasmid (FIG. 4A, Lane 2). Since the rHBV-CreN pgRNA was shorter than that of the wtHBV, it was expected that the rHBV-CreN DNA, which is produced from pgRNA, is smaller than the wtHBV genome. The result indicates the Co-InCreN cassette doesn't interfere with the replication of rHBV-CreN. Different than the HBV DNA species observed in the capsids derived from HepAD38 cells, two bands refer to rcDNA and dslDNA were detected in the viral particles in the supernatant of HepAD 38 cells (FIG. 4B, Lane 5). The rc- and dsl-form of rHBV-CreN DNA were detected in the viral particle secreted from the co-transfected cells (FIG. 4B, Lane 2). This demonstrates that the production of rHBV-CreN via the trans-complement manner was successful. However, several bands above the 3.2 kb marker were detected in the supernatant of the rHBV-CreN producing cells (FIG. 4B, Lane 2). This indicates the plasmid DNA were co-precipitated with the rHBV-CreN.

As shown in the previous result (FIG. 4B), plasmid DNA is precipitated along with virus particles by using PEG to concentrate virus. In order to increase the purity and to scale up the virus production, heparin affinity chromatography together with recombinant DNase (rDNase) on-column digestion were utilized. HBV viral particles and sub-viral particles bind to the heparin column via the interaction between HBV surface proteins and heparan sulfate proteoglycans. Additional rDNase on-column digestion removes the plasmid DNA, which is likely being associated with viral particles. Extracellular media was collected from the Huh7 cells co-transfected with rHBV-CreN vector and the helper plasmid. The collection started on day 5 post-transfection and since the media was collected every 4 days for a total of 6 times. DNA samples isolated from PEG-precipitated virus stock and heparin column-purified virus stock were analyzed by Southern blot. The rHBV-CreN rcDNA and dslDNA were detected in the DNA samples of the rHBV-CreN precipitated by PEG or purified by the heparin column procedure (FIG. 5). This indicates that the stability of the viral particles was not affected by using the heparin affinity chromatography together with rDNase on-column digestion to purify virus. Moreover, the bands above the 3.2-kb marker were not detectable in the DNA sample from virus purified via the heparin column procedure. This indicates the purity of the virus stock was greatly improved because of the elimination of input plasmids. Furthermore, the inventors examined the viral morphology under electron microscopy. A Dane-like particle, which is approximately 42 nm in diameter, with an electron-dense core was observed (FIG. 15). This indicates rHBV-CreN displays the structural features identical to wtHBV (Dane et al., 1970, Nucleic acids research 37, 2560-2573).

In summary, the inventors surprisingly found that rHBV-CreN can be efficiently produced in a trans-complement manner. Purification of a large input reporter virus material can be achieved by using heparin affinity chromatography together with rDNase on-column digestion.

Example 2: Generation of a Cre Reporter Cell Line (Reporter Cell)

To monitor the cre activity via fluorescence in the cells, a Cre-induced DsRed plasmid (pCALNL-DsRed) was utilized. This plasmid (SEQ ID NO: 9) contains the following elements: the CAG promoter, a loxP-flanked neo-pA cassette and the DsRed coding sequence. The expression of neomycin phosphotransferase (neo) is driven by the CAG promoter. Due to the polyA site and the stop codon of neomycin phosphotransferase, the transcription and translation will be terminated at the loxP-flanked neo-pA cassette. The expression of DsRed will only be initiated upon the removal of the loxP-flanked neo-pA cassette mediated by the Cre-lox recombination. Since the rHBV-CreN only carries the N-terminal component of the Co-InCre system, the C-terminal component of the Co-InCre system, Co-InCreC, is required additionally for executing the recombinase function. To combine the Co-InCreC cassette and the Cre-induced DsRed cassette into one plasmid, the Co-InCreC cassette was inserted into pCALNL-DsRed (FIG. 1A). The newly generated plasmid was transfected into HepG2-NTCP-K7 cells, and the cells were selected with neomycin (2 mg/ml). The obtained cell line is designated HepG2-NTCP-CreC-CIR cells (CreC/CIR cells; CIR: Cre induced red). To verify the cell line, the functional complementation of the split Cre as well as the activation of the Cre reporter cassette (Cre-induce DsRed) in the cells was evaluated first. Plasmid containing Co-InCreN was transfected into CreC/CIR cells. DsRed expression was examined under fluorescence microscopy and by FACS analysis on day 4 post-transfection. Fluorescence microscopic images showed that no DsRed signal was observed in CreC/CIR cells transfected with control plasmid (pcDNA3.1) (FIG. 6A, left image). This indicates that the unspecific cre-lox recombination did not take place in CreC/CIR cells. In contrast, the CreC/CIR cells became DsRed positive was observed in the group administered with the plasmid containing Co-InCreN (FIG. 6A, right image). Moreover, FACS analysis showed that approximately 13% of the CreC/CIR cells transfected with CreN plasmid become DsRed-positive (FIG. 6B). This indicates the DsRed expression was activated in the presence of Co-InCreN and Co-InCreC. The activation is most likely mediated by the Cre-lox recombination. To confirm the genome-editing event took place upon the reassembling of Co-InCreN and Co-InCreC in the CreC/CIR cells was the next step. Genomic DNA was isolated from CreC/CIR cells transfected with or without plasmid containing CreN. In the DNA sample of the control group, a single PCR product, approximately 1800 bp, was detected using primers amplifying the loxP cassette. In the DNA samples isolated from CreN-transfected cells, an additional band in size of 1.2 kb appeared. This indicates that the DNA flanked by loxP sites was removed (FIG. 6C).

The last step was to check the ability to support HBV infection in the CreC/CIR cells was not lost during the clonal selection procedure. CreC/CIR cells and its parental cells, HepG2-NTCP-K7 cells, were infected with wtHBV, respectively. On day 4 post-infection, the supernatant was collected to analyze the HBeAg expression and the DNA was isolated from the cells to analyze the level of cccDNA. The level of HBeAg expression and the amount of cccDNA in the infected CreC/CIR cells are comparable to the infected HepG2-NTCP-K7 cells (FIG. 7).

Taken together, DsRed expression can be initiated via Cre-lox recombination in the CreC/CIR cells. Additionally, the cells retain the ability of being susceptible to wtHBV infection.

Example 3: Infection of rHBV-creN in the Cre Reporter Cells

Having characterized the reporter cells and purified successfully the reporter virus, the capability of monitoring the rHBV-Cre infection in the Cre/CIR cells was investigated. The characterization of rHBV-CreN infection began with determining the multiplicity of infection (MOI) for detecting the DsRed signal. On day 7 post-infection, cells were examined under fluorescence microscope and then subjected to FACS analysis. In addition, supernatant was collected for HBeAg ELISA (FIG. 8A). The number of DsRed-positive cells increased in proportion to the MOI of rHBV-CreN (FIG. 8B, C). It varied from 1.5% of DsRed-positive cells at MOI=25 to 7.6% at MOI=1600 as determined by FACS. Moreover, the tendency of DsRed expression closely correlated to the expression of HBeAg (FIG. 8C).

Next, the kinetics of DsRed expression and HBeAg secretion were analyzed. CreC/CIR cells were infected with rHBV-CreN at a MOI of 300 genome equivalents/cell and harvested at day 1, 4, 7, 10, 13 and 16 post-infection (dpi). DsRed expression of the infected cells was visible under the fluorescence microscopy from 4 dpi onwards. Moreover, the fluorescent signal lasted until day 16 post-infection (FIG. 9A). In contract, the DsRed signal of the uninfected CreC/CIR cells (mock) remained negligible throughout the culture period. Linear growth of the percentage of the DsRed-positive cells was observed between 1 to 7 dpi. The increase was modest from 7 to 13 dpi and then started to decrease (FIG. 9B). Additionally, the kinetic of DsRed expression from 4 dpi on matched that of the HBeAg expression. This suggests that the expression kinetic of DsRed reflects the expression kinetic the viral protein (HBeAg).

To verify the establishment of rHBV infection, the kinetic of the cccDNA formation was analyzed. CreC/CIR cells were infected with rHBV-CreN (MOI=1000) and harvested at 1, 4, 7 and 10 dpi. DNA was isolated by using Hirt extraction procedure, and the level of cccDNA and PF-rcDNA were analyzed by Southern blot. As shown FIG. 10, rHBV-CreN cccDNA was detected on day 4 post-infection and thereafter it gradually decreased. The kinetic of PF-rcDNA was similar to that of cccDNA, its amount peaked at 4 dpi and then declined. This indicates the HBV replication template, cccDNA, was established in the cells infected with rHBV-CreN.

Finally, the uptake of rHBV-CreN was examined. Myrcludex-B (MyrB) is a lipopeptide consisting of amino acid residues 2-48 of the preS1 region of HBV. MyrB competes with viral particles for binding to NTCP and thereby blocks HBV infection. CreC/CIR cells were infected with rHBV-CreN (MOI=250) together with the MyrB. DsRed expression in the cells and HBeAg in the supernatant and cells were analyzed on day 7 post-infection (FIG. 11A). Similar to previous result (FIG. 9), DsRed expression was observed in the CreC/CIR cells upon rHBV-CreN infection (FIG. 11B, middle), as shown by fluorescence imaging and FACS analysis. In the presence of MyrB, the number of DsRed-positive cells was reduced to less than 1%, which is comparable to the mock group (FIG. 11B). In addition, the HBeAg level of the MyrB-treated sample was comparable to that of the mock sample (FIG. 11C). However, the HBeAg level of the rHBV-infected sample was much lower than that of the wtHBV-infected sample. The results indicate rHBV-CreN infection was blocked by MyrB and suggests that rHBV-CreN virus enters the cells via the same pathway as wtHB V.

Altogether, the results have shown that rHBV-CreN induced DsRed expression in a dose-dependent manner. The signal of DsRed and cccDNA were detected 4 days after infection, thus proving the concept of the present invention. Moreover, the infection was prevented by MyrB treatment showing that the present invention may be used in methods for screening for new therapeutic strategies.

Example 4: Validation of the rHBV-CreN Reporter System

To prove the establishment of rHBV-CreN infection in the Cre reporter cells (CreC/CIR cells), cccDNA formation was analyzed by Southern blot analysis. Two bands—cccDNA and protein-free dslDNA—were detected in the DNA from the infected cells (FIG. 16). The XhoI digestion confirmed that the lower band as cccDNA and the upper band as dslDNA. This indicated the rHBV infection was established in the cells. Next, we analyzed the Co-InCre reconstitution by Western blot (FIG. 17). As expected, a constant expression of Co-InCreC was detected in CreC/CIR cells. A higher molecular size band (Co-InCre) was only detected in the infected sample indicating Co-InCre reconstitution takes place upon the infection. Core protein, which is derived from cccDNA, was detected using the same sample. These results implied that the split-Cre reconstitution could be a subsequent event of cccDNA formation. Co-InCre and core were not detected in infected sample treated with an HBV entry inhibitor—MyrcludexB (MyrB) (Li and Urban, 2016, Cancer research 42, 3858-3863). MyrB prevents rHBV-CreN infection suggesting that it enters the cells via the same pathway as wtHBV. Cre-lox recombination upon the Co-InCre reassembly in the infected cells was analyzed by PCR using primers amplifying the loxp-Neo-Stop-loxp cassette (FIG. 18). A 1.5-kb band (Neo) was detected for all samples. In addition, a 0.2-kb band (ΔNeo) was detected in the infected sample but was absent in the MyrB-treated sample. This result indicated the Neomycin sequence flanked by loxP sites was removed in infected cells. Altogether, these results showed that Cre-lox recombination takes place upon rHBV-CreN infection.

Example 5: Exemplary Application of the rHBV-CreN Reporter System

To monitor the Cre-lox recombination upon rHBV-CreN infection, the inventors examined the DsRed expression in the CreC/CIR cells. In these cells, DsRed expression is constantly deactivated by the loxp-Neo-stop-loxp cassette, and it can be turned on when the cassette is removed (Matsuda and Cepko, 2007, Proc Natl Acad Sci USA 104, 1027-1032). As expected, No DsRed signal was detected in the mock sample (FIG. 19A, upper panels). This indicated DsRed expression is halted by the stop sequence, and its expression is not interfered by the presence of Co-InCreC. In infected samples, DsRed-positive cells were observed (FIG. 19A, middle and lower panels) indicating DsRed expression being activated upon rHBV-CreN infection. To confirm viral infection, cells were co-stained for core protein using an anti-core antibody. Notably, the expression level of DsRed and core varied among these cells. Besides cells co-expressing DsRed and core, cells expressing either DsRed or core were observed in infected samples. The cells only expressing DsRed could derive from the infection with virions carrying dslDNA genome. And the cells only positive for core protein might arise from insufficient Cre-lox recombination in infected cells. The number of DsRed-positive cells was determined by flow cytometry (FIG. 19B). Approximately 38% of the cells were DsRed positive with a multiplicity of infection (MOI) of 300. In the presence of MyrB, the percentage of DsRed-positive cells reduced to less than 1%. This result verified the previous data (FIGS. 17 and 18), which showed the inhibition of rHBV-CreN infection by MyrB. The number of DsRed-positive cells from the depicted samples were positively associated to their respective HBV e antigen (HBeAg) level, which is a HBV replication marker that is correlated to cccDNA level (Ko et al., 2018, J Hepatol) (FIG. 19B, right graph). The correlation of DsRed and HBeAg expression was further confirmed by comparing their levels from cells infected with increasing MOI of rHBV-CreN (FIG. 19C). These results suggested that DsRed expression in infected cells can be used as an effective marker to detect viral infection.

In rHBV-CreN infected cells, HBeAg is expressed from the cccDNA, whereas DsRed is expressed from genome of the infected cells. Since the number of cccDNA is maintained independently of the cell genome, we wanted to investigate the kinetic of HBeAg and DsRed expression in the infected cells. The expression of HBeAg and DsRed remained stable for 28 days in our rHBV-CreN infection model (FIG. 19D, left panel). When we split the infected cells to promote cell proliferation, HBeAg level decreased more than four-folds (FIG. 19D, right panel). This suggests that the cccDNA pool in the infected cells was lost during cell division. The percentage of DsRed-positive cells remained at a similar level after splitting the cells once. A 20% reduction of DsRed-positive cell number was observed after the second split. Importantly, these results indicate the activated DsRed cassette can be passed on from the parental rHBV-infected cells to newly generated cells. Here, we showed that using a reporter derived from a host genome can serve as a stable marker for monitoring the infection.

To demonstrate that the fate of the rHBV-infected cells can be monitored in real-time by a live-cell analysis system, the inventors incubated these cells with HBV-specific T cells. HBV core-specific (C18) or S-specific (S20) T cells generated by retroviral transduction have been shown to efficiently eliminate wtHBV-infected cells (Wisskirchen et al., 2019, Journal of clinical investigation 130; Wisskirchen et al., 2017, PLoS One 12, e0182936). The fluorescence intensity remained constant when the rHBV-infected cells were co-cultured with S-specific T cells (FIG. 19E, grey line). This was expected since the envelope coding sequence is deleted in rHBV-CreN genome (see FIG. 14). To the contrary, when using core-specific T cells, the fluorescence intensity reduced to less than 12% within 43 hours (FIG. 19E, black line), which is consistent with the previous findings (Wisskirchen et al., 2019, Journal of clinical investigation 130). Interestingly, the fluorescence intensity of the cells co-cultured with core-specific T cells gradually increased again to 21% after 48 hours (FIG. 19E, black line). This suggested that the remaining DsRed-positive cells started to proliferate, and the daughter cells expressed DsRed. Taken together, the inventors showed that the rHBV-CreN reporter system can be used to assess therapeutic strategies targeting HBV infection. Moreover, unlike the conventional wtHBV infection model, our reporter system can support cell tracking at a single-cell level in real-time.

We showed in FIG. 18 that the neomycin sequence is removed in the rHBV-infected cells. Therefore, we proposed that these infected cells are sensitive to the antibiotic treatment. The number of DsRed-positive cells was reduced by 3.6-fold in the presence of Neomycin for 30 days as compared to untreated group (FIG. 19F). Hence, the inventors demonstrated the possibility to perform a negative selection by using our rHBV-CreN reporter system.

The invention claimed is:

1. An in vitro method of assessing the capacity of a substance to treat or prevent hepatitis B virus (HBV) infection comprising:
   (a) contacting a reporter cell with a recombinant HBV (rHBv);
   (b) contacting the reporter cell with the substance; and
   (c) analyzing a reporter gene expression by the reporter cell;
   wherein the recombinant HBV comprises a nucleic acid encoding a first fragment of a Cre recombinase;
   wherein the reporter cell comprises a nucleic acid encoding a second fragment of the recombinase;
   wherein the first fragment of the recombinase and the second fragment of the recombinase are capable of forming a functional recombinase;
   wherein the reporter cell comprises a nucleic acid comprising a stop cassette flanked by two recombination sites fused to a reporter gene, wherein the presence of the stop cassette suppresses expression of the reporter gene;
   wherein a decrease of the reporter gene expression in the reporter cell contacted with the substance relative to reporter gene expression in the same reporter cell being contacted with said rHBV but without being contacted with said substance, is indicative for the capacity of the substance to treat or prevent HBV infection;
   wherein the first fragment of the Cre recombinase is CreN and the second fragment of the Cre recombinase is CreC.

2. The method of claim 1, wherein the reporter cell is an animal cell, optionally a mammalian cell.

3. The method of claim 1, wherein the reporter cell comprises a sodium taurocholate cotransporting polypeptide (NTCP).

4. The method of claim 1, wherein the reporter cell is a hepatocyte and/or a hepatoma cell.

5. The method of claim 1, wherein the first fragment of the recombinase has the amino acid sequence set forth in SEQ ID NO: 2.

6. The method of claim 1, wherein the second fragment of the recombinase has the amino acid sequence set forth in SEQ ID NO: 7.

7. The method of claim 1, wherein the recombination site is a loxP site.

8. The method of claim 1, wherein the stop cassette is a transcriptional stop cassette or translational stop cassette.

9. The method of claim 1, wherein the reporter gene encodes a detectable gene product.

* * * * *